US012775008B2

(12) United States Patent
Tofaris et al.

(10) Patent No.: US 12,775,008 B2
(45) Date of Patent: Oct. 27, 2026

(54) BIOMARKERS FOR THE PREDICTION AND IDENTIFICATION OF PARKINSON'S DISEASE

(71) Applicant: Oxford University Innovation Limited, Oxford (GB)

(72) Inventors: George Tofaris, Oxford (GB); Jason Davis, Oxford (GB); Cheng Jiang, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 1025 days.

(21) Appl. No.: 17/775,605

(22) PCT Filed: Nov. 11, 2020

(86) PCT No.: PCT/GB2020/052872
§ 371 (c)(1),
(2) Date: May 10, 2022

(87) PCT Pub. No.: WO2021/094751
PCT Pub. Date: May 20, 2021

(65) Prior Publication Data

US 2022/0390470 A1 Dec. 8, 2022

(30) Foreign Application Priority Data

Nov. 11, 2019 (GB) ..................................... 1916388
Nov. 11, 2019 (GB) ..................................... 1916390
Feb. 19, 2020 (GB) ..................................... 2002289
Feb. 19, 2020 (GB) ..................................... 2002290

(51) Int. Cl.
*G01N 33/543* (2006.01)
*G01N 33/68* (2006.01)

(52) U.S. Cl.
CPC . *G01N 33/54333* (2013.01); *G01N 33/54306* (2013.01); *G01N 33/54393* (2013.01); *G01N 33/6896* (2013.01); *G01N 2333/4703* (2013.01); *G01N 2446/20* (2013.01); *G01N 2446/86* (2013.01); *G01N 2800/2835* (2013.01)

(58) Field of Classification Search
CPC ....... G01N 33/54333; G01N 33/54306; G01N 33/54393; G01N 33/6896; G01N 2333/4703; G01N 2446/20; G01N 2446/86; G01N 2800/2835
See application file for complete search history.

(56) References Cited

U.S. PATENT DOCUMENTS

2009/0258951 A1 10/2009 Hsu et al.
2014/0235803 A1 8/2014 Jiang et al.
2015/0119278 A1 4/2015 Goetzl
2016/0363599 A1 12/2016 Goetzl
2017/0102397 A1 4/2017 Zhang
2019/0011460 A1 1/2019 Goetzl

FOREIGN PATENT DOCUMENTS

CN 104884094 A 9/2015
DE 10 2007 024382 A1 11/2008
JP 2010-530955 A 9/2010
JP 2016-057106 A 4/2016
JP 2016-536598 A 11/2016
JP 2017-525976 A 9/2017
JP 2019-526671 A 9/2019
JP 2019-527353 A 9/2019
WO 2008/083390 A2 7/2008
WO 2014/059052 A1 4/2014
WO 2014/168230 A1 10/2014
WO 2016/044665 A1 3/2016
WO 2018/094120 A1 5/2018
WO 2018/218090 A1 11/2018
WO 2019/014486 A1 1/2019
WO 2019/171035 A1 9/2019

OTHER PUBLICATIONS

International Search Report and Written Opinion for WO 2021/094751 (PCT/GB2020/052872), dated Apr. 13, 2021, pp. 1-22.
UK Search Report for GB 1916390.6, dated May 11, 2020, pp. 1-4.
Mitsutaka Yoshida et al: "Preferential capture of EpCAM-expressing extracellular vesicles on solid surfaces coated with an aptamer-conjugated zwitterionic polymer", Biotechnology and Bio Engineering, vol. 115, No. 3, Nov. 22, 2017 (Nov. 22, 2017), pp. 536-544.
Gahee Kim et al: "Noble Polymeric Surface Conjugated with Zwitterionic Moieties and Antibodies for the Isolation of Exosomes from Human Serum", Bioconjugate Chemistry, vol. 23, No. 10, Oct. 17, 2012 (Oct. 17, 2012), pp. 2114-2120.
Alexopoulou et al., Proc Natl Acad Sci U S A. 2016;113:E4688-4697.
Alvarez-Erviti et al., Neurobiol Dis. 2011;42:360-367.
Behari et al., Ann Indian Acad Neurol. Jul. 2011; 14(Suppl1): S2-S6.
Berg et al. Mov Disord. 2015;30:1600-1611.
Boot et al., Ann Neurol. 2012;71:49-56.
Braak et al. Neurobiol Aging. 2003;24:197-211.
Cerri et al., Front Cell Neurosci. 2018;12:125.
Dalrymple-Alford et al., Neurology. 2010;75:1717-1725.
Deng et al., 2013, Anal Chim Acta 771: 31-36.
Dong et al., J Colloid Interface Sci. 2014; 432: 135-143.
El-Agnaf et al., FASEB J. 2003; 17:1945-1947.
Eusebi et al., Mov Disord. 2017;32:1389-1400.

(Continued)

*Primary Examiner* — Olga N Chernyshev
(74) *Attorney, Agent, or Firm* — Thomas |Horstemeyer, LLP

(57) ABSTRACT

The invention relates to using serum exosomal proteins, α-synuclein and clusterin, as biomarkers in the prediction and identification of a subject having Parkinson's Disease, and provides methods for determining their levels. The biomarkers are also useful for monitoring, prevention and/or treatment of Parkinson's Disease and in differentiating Parkinson's disease from atypical parkinsonian syndromes including MSA.

11 Claims, 26 Drawing Sheets

(56) References Cited

OTHER PUBLICATIONS

Fairfoul et al., Annals of Clinical and Translational Neurology 2016; 3(10): 812-818.
Faure et al. Mol. Cell. Neurosci. 31, 642-648 (2006).
Fereshtenhnejad et al. Brain. 2019;142:2051-2067.
Fujiwara et al., Nat Cell Biol. 2002;4:160-164.
Fussi et al., Cell Death Dis. 2018;9:757.
Gelb et al., 1999, Arch Neurol, 56:33-39 (copy of reference not provided).
Gibb and Lees, 1988, J Neurol Neurosurg Psychiatry, 51:745-52.
Harold et al. Nat Genet. 2009;41:1088-1093.
Hasegawa et al., PLoS One. 2011;6:e29460.
Hely et al. Mov Disord. 2008;23:837-844.
Hopfner et al., Transl Neurodegener 2019, 8, 11.
Jiang et al., ACS Sensors. 2016;1:1432-1438.
Jiang et al., J Neurol Neurosurg Psychiatry. Jul. 2020;91(7):720-729.
Keefe et al., Nat. Chem., 2012, 4, 59-63.
Kitamura, Neuroscience 392 (2018) 121-128 .
Lachenal et al., Mol. Cell. Neurosci. 46, 409-418 (2011).
Lambert et al., Nat Genet. 2009;41:1094-1099.
Li et al., Biomaterials 2014; 35(36):9731-45.
Mahmud et al., Langmuir . Sep. 6, 2011; 27(17): 10800-10804.
Manfredi et al., J Neural Transm Suppl. 1995;45:1-9.
Minakaki et al., Autophagy. 2018;14:98-119.
Mollenhauer et al., Lancet Neurol. 2011; 10:230-240.
Parnetti et al., Lancet Neurol. 2019;18:573-586.
Postuma et al., 2015, Mov Disord, 30:1591-1601.
Postuma et al., Brain. 2009;132:3298-3307.
Postuma et al., Neurology. 2015;84:1104-1113.
Postuma, Nature reviews, Neurology, vol. 15, 2019.
Ratcliffe et al., Polym Chem 5: 3643-3655.
Robinson et al., Brain. 2018; 141:2181-2193.
Shi et al., Acta Neuropathol. 2014;128:639-650.
Shi et al., Neurosci Lett. 2010;480:78-82.
Slot et al., Neurobiol Aging. 2019;79:101-109.
Steudl et al., 2016, Brain, 139, 481-494.
Thambisetty et al., Arch Gen Psychiatry. 2010;67:739-748.
Tofaris and Spillantini Cell Mol Life Sci. 2007;64:2194-2201.
Tofaris et al., Proc Natl Acad Sci U S A. 2011;108:17004-17009.
Tofaris J Parkinsons Dis. 2017;7:569-576.
Tofaris Mov Disord. 2012;27:1364-1369.
Tomlinson et al., Ann Clin Transl Neurol. 2015;2:353-361.
Vaisocherová et al., Analytical Chemistry, 2008, vol. 80, No. 20, 7894-7901.
Van Rumund et al., ANNNEUROL 2019;85:777-781.
Visova et al., Langmuir, 2020, 36, 8485-8493.
Wang et al., ACS Appl Mater Interfaces. 2014; 6(6): 4550-4559.
Wang et al., Sci Transl Med. 2012;4:121ra120.
Yang et al., Metabolic Brain Disease. 2019;34:129-140.
Zhang et al., 2008 Chem Mater 20: 3345-335.
Japanese Office Action for Patent Application No. 2022-526772, dated Oct. 29, 2024, pp. 1-5 (Translation Included).
Japanese Office Action for Patent Application No. 2022-526724, dated Oct. 29, 2024, pp. 1-5 (Translation Included).
Chinese Office Action for Patent Application No. 202080092653.0, dated Apr. 25, 2025, pp. 1-26 (Translation Included).
Xu et al., The Journal of Nanchang University (Medical Science), 2013, 53(11):94-99 (Translation Included).
CN Search Report for Patent Application No. 202080092653.0, dated Apr. 24, 2025, pp. 1-3.
Hope Kronman et al., "Multidimensional Effects of Stress on Neuronal Exosome Levels and Simultaneous Transcriptomic Profiles", 2024 The Authors. Published by Elsevier Inc on behalf of the Society of Biological Psychiatry. ISSN: 2667-1743 Biological Psychiatry: Global Open Science Jan. 2025; 5:100401 www.sobp.org/GOS, pp. 1-11.
Gang Cheng et al., "Zwitterionic carboxybetaine polymer surfaces and their resistance to long-term biofilm formation", NIH Public Access, Author Manuscript, Biomaterials. Author manuscript; available in PMC Feb. 19, 2010. Published in final edited form as: Biomaterials. Oct. 2009 ; 30(28): 5234-5240. doi: 10.1016/j.biomaterials.2009.05.058, pp. 1-15.
Esther van Andel et al., "Highly Specific Binding on Antifouling Zwitterionic Polymer-Coated Microbeads as Measured by Flow Cytometry", ACS Publications, 2017 American Chemical Society DOI: 10.1021/acsami.7b09725 ACS Appl. Mater. Interfaces 2017, 9, 38211-38221, pp. 1-11.
Receiver Operating Characteristic Curve in Diagnostic Test Assessment by Mandrekar (2010).
Exosomes: biogenesis, biologic function and clinical potential by Zhang et al (Cell Biosci. Feb. 2019 9:19).
Clusterin as a therapeutic target by Wilson and Zoubeidi (Expert Opinion on Therapeutic Targets, 2017, 21 (2):201-203).
The value of early diagnosis and treatment in Parkinson's disease by Tinelli, Kanavos and Federico Grimaccia (2016, LSE Consulting Reports).
Cardenes et al. ALCAM/CD166IsInvolved in the Binding and Uptake of Cancer-Derived Extracellular Vesicles. Int. J. Mol. Sci. 2022).
Wikberg et al. (Grafting of silica with sulfobetaine polymers via aqueous reversible addition fragmentation chain transfer polymerization and its use as a stationary phase in HILIC. J. Sep. Sci. 2009, 32, 2008-2016).
Wang et al. (RAFT Polymerization on Particle Surfaces: Same Goal, Different Strategies. Controlled Radical Polymerization: Materials Chapter 13 pp. 187-201).
Cai et al. (Zwitterionic polymers grafted poly(ether sulfone) hollow fiber membranes and their antifouling behaviors for osmotic power generation. Journal of Membrane Science 497 (2016) 142-152).
Ranjan et al., Synthesis of High Density Polymer Brushes on Nanoparticles by Combined RAFT Polymerization and Click Chemistru, Macromolecular Rapid Communications, 2008, pp. 1104-1110, vol. 29, WILEY-VCH Verlag GmbH & Co. KGaA, Weinheim, Germany.
Higaki et al., Anti-fouling behavior of polymer brush immobilized surfaces, Polymer Journal, Jan. 13, 2016, pp. 325-331, vol. 48.
Office Action for U.S. Appl. No. 17/775,602 mailed Apr. 22, 2026.

Fig. 3A
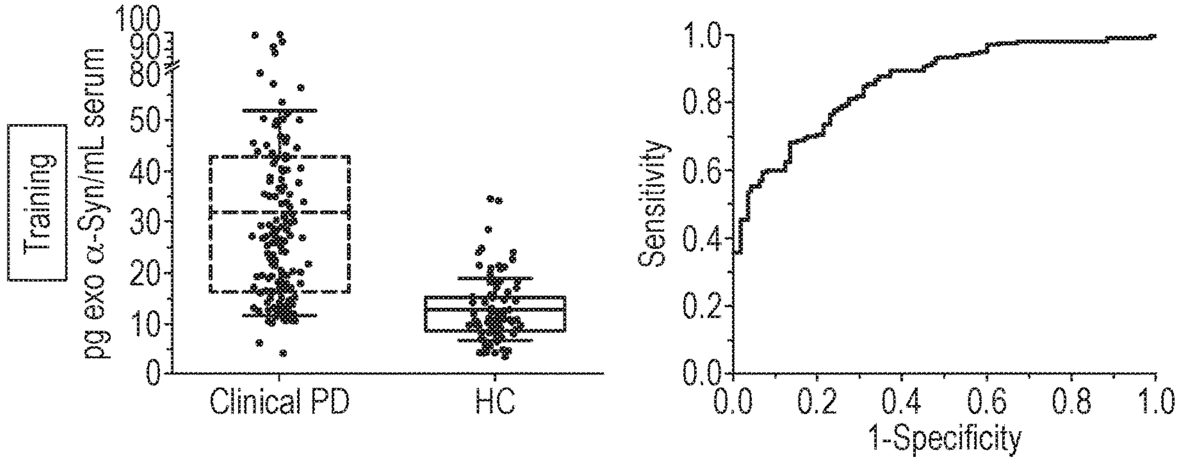
Fig. 3B
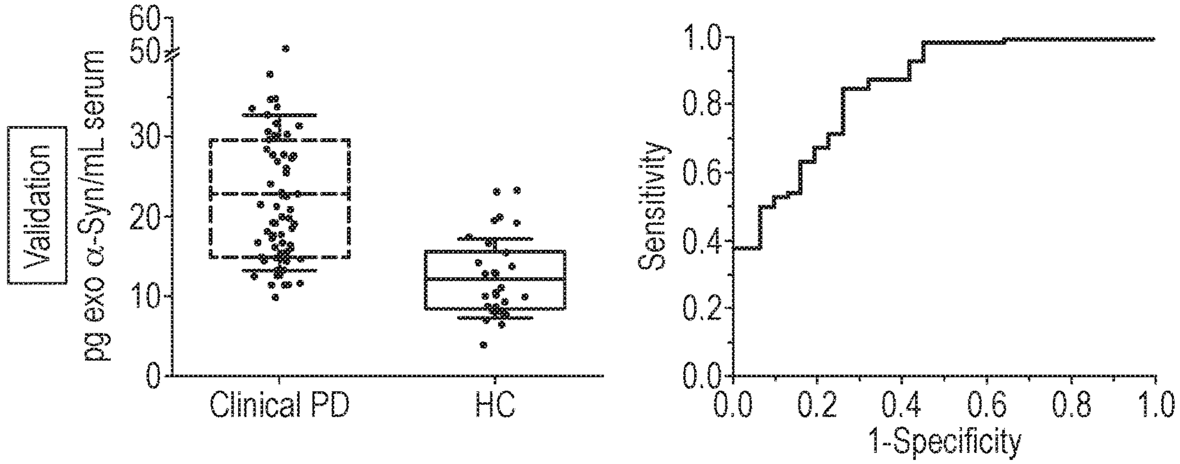
Fig. 3C
| Groups | Patient Numbers | exo α-Syn cut-off | AUC | Sens | Spec | PPV | NPV |
|---|---|---|---|---|---|---|---|
| Training (Kiel, Brescia) | Clinical PD vs HC (201 vs 113) | 14.21 pg/mL | 0.86 | 0.82 | 0.71 | 0.83 | 0.72 |
| Validation (Oxford) | Clinical PD vs HC (74 vs 31) | | 0.86 | 0.85 | 0.74 | 0.89 | 0.68 |

Fig. 4A
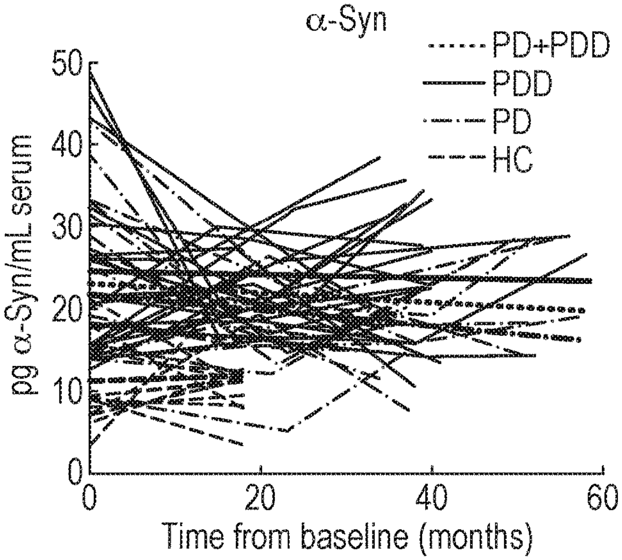
Fig. 4B
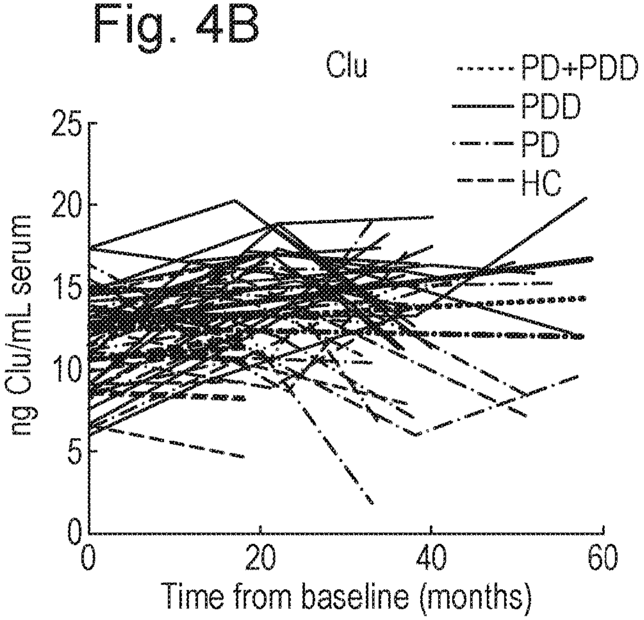
Fig. 4C
| | PD | PDD | Clinical PD | HC |
|---|---|---|---|---|
| n. first visit | 20 | 20 | | 14 |
| n. second visit | 20 | 20 | | 14 |
| n. third visit | 20 | 20 | | – |
| male (female) | 11(9) | 16(4) | 27(13) | 13(1) |
| Age at first sampling, mean | 63.15 | 69.35 | 66.25 | 65.28 |
| Gradient, k (α-Syn) | -0.0952 | -0.0213 | -0.0582 | 0.0492 |
| *p* value (α-syn) | 0.0757 | 0.7210 | 0.1626 | 0.6376 |
| Gradient, k (Clu) | -0.0105 | 0.0676 | 0.0284 | 0.0421 |
| *p* value (Clu) | 0.6818 | 0.6818 | 0.1234 | 0.4412 |

Fig. 7A
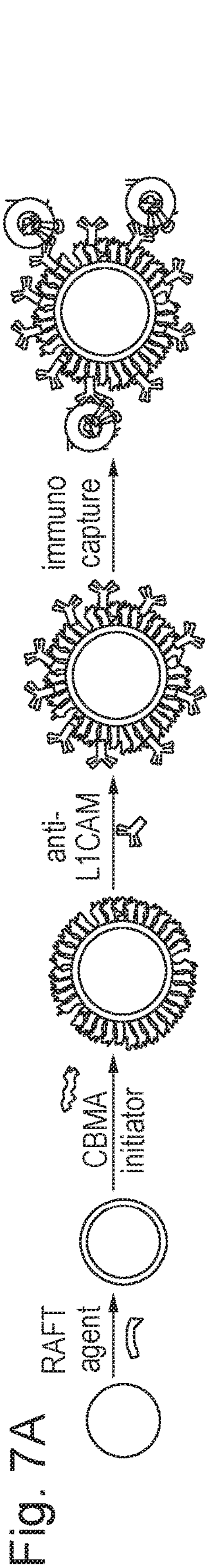
Fig. 7B
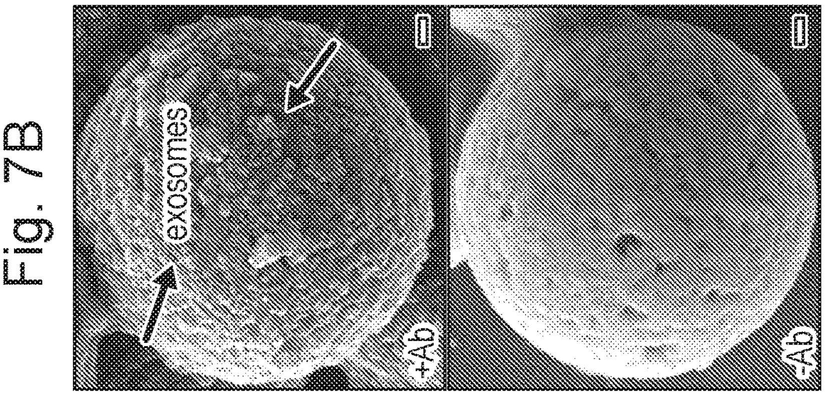
Fig. 7C
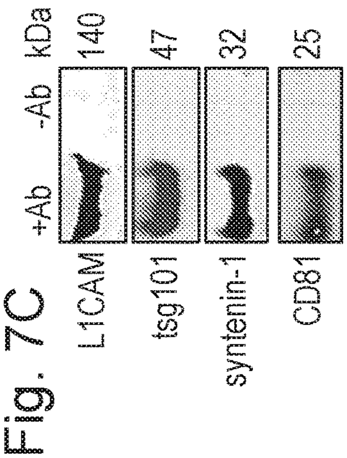
Fig. 7D
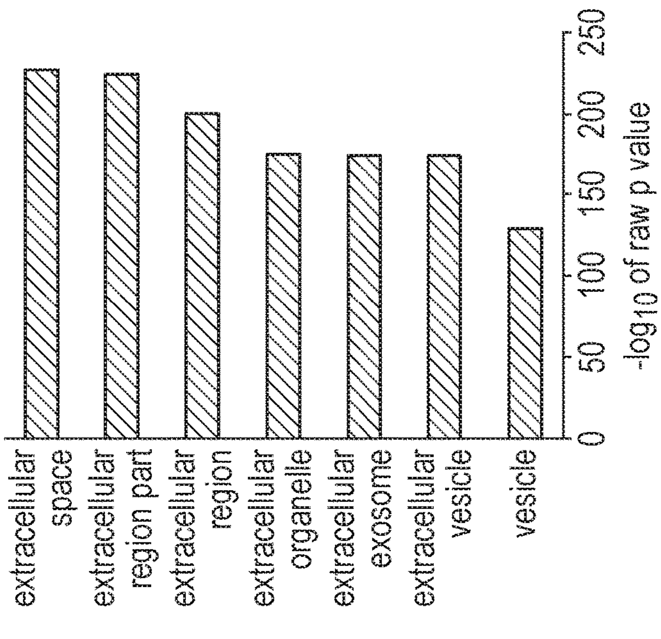
Fig. 7E
| Protein ID | MS score |
|---|---|
| Clusterin | 674 |
| 14-3-3 δ/ζ | 396 |
| HSP 70 | 141 |
| Rab-10 | 105 |
| Cathepsin G | 73 |
| DJ-1 | 72 |
| CD9 | 69 |
| NCAM | 43 |
| Syntenin-1 | 33 |

| α-Synuclein (pg/mL) | Signal 1 | Signal 2 | Signal mean | CV | % Recovery mean | Calculated concentration mean (pg/mL) | Calculated concentration CV |
|---|---|---|---|---|---|---|---|
| 10500 | 53654 | 44327 | 48991 | 13.5 | 101 | 10601 | 25.7 |
| 2625 | 20314 | 16222 | 18268 | 15.8 | 103 | 2698 | 17.5 |
| 656 | 4013 | 5003 | 4508 | 15.5 | 95.3 | 626 | 16.5 |
| 164 | 2118 | 1180 | 1649 | 40.2 | 111 | 181 | 62.6 |
| 41 | 828 | 828 | 828 | 0.0 | 73.5 | 30.2 | 0.0 |
| 10.3 | 788 | 728 | 758 | 5.6 | 124 | 12.8 | 88.8 |
| 2.56 | 693 | 715 | 704 | 2.21 | NA | NA | NA |
| 0 | 775 | 714 | 744 | 5.79 | NA | NA | NA |

| Clusterin (pg/mL) | Signal 1 | Signal 2 | Signal mean | CV | % Recovery mean | Calculated concentrati on mean (pg/mL) | Calculated concentrati on CV |
|---|---|---|---|---|---|---|---|
| 250000 | 123552 | 123592 | 123592 | 0.02 | 93.2 | 233031 | 0.04 |
| 62500 | 40318 | 41746 | 41032 | 0.92 | 104 | 64874 | 0.94 |
| 15625 | 9755 | 9441 | 9598 | 2.31 | 99.5 | 15553 | 2.11 |
| 3906.3 | 2422 | 2142 | 2282 | 8.68 | 98.9 | 3863 | 9.54 |
| 976.6 | 902 | 865 | 883.5 | 2.96 | 100 | 979 | 6.57 |
| 244.1 | 607 | 635 | 621 | 3.19 | 107 | 262 | 24.5 |
| 0 | 577 | 524 | 550.5 | 6.81 | NA | NA | NA |

| Syntenin (pg/mL) | Signal 1 | Signal 2 | Signal mean | CV | % Recovery mean | Calculated concentrati on mean (pg/mL) | Calculated concentrati on CV |
|---|---|---|---|---|---|---|---|
| 625000 | 5114 | 4915 | 5015 | 2.81 | 104 | 650467 | 3.26 |
| 156250 | 1260 | 1260 | 1260 | 0.00 | 94.4 | 147482 | 0.00 |
| 39062.5 | 581 | 566 | 573.5 | 1.85 | 117 | 45602 | 4.12 |
| 9765.63 | 473 | 445 | 459 | 12.4 | 91.3 | 9641.6 | 5.31 |
| 2441.41 | 374 | 397 | 385.5 | 13.9 | 94.3 | 2113.5 | 13.2 |
| 610.352 | 344 | 446 | 395 | 18.3 | NA | NA | NA |
| 0 | 372 | 398 | 385 | 4.78 | NA | NA | NA |

| Antibody pairs | | Standards | |
|---|---|---|---|
| Capture Ab | 11A5 (ATCC#PTA822) | α-Syn | pSer129 |
| Detection Ab | 4B12 (Biolegend#807802) | human α-Syn (rPeptide) rPeptide S-1001-1 | human a-Syn (rPeptide), in vitro phosphorylated by PLK2 BE04205-020 |

Specificity for pSer129 pS129 11A5/4B12 Ab pairing

Reproducibility for pSer129
Standard curve overlay of eight independent runs on separate days

| Conc. (pg/ml) | Average Signal | %CV |
|---|---|---|
| 10000.00 | 99141.44 | 15.8 |
| 2000.00 | 22842.63 | 17.4 |
| 400.00 | 4476.94 | 16.0 |
| 80.00 | 1009.13 | 16.9 |
| 16.00 | 271.13 | 15.0 |
| 3.20 | 113.19 | 10.1 |
| 0.64 | 79.31 | 7.9 |
| 0.0 | 70.19 | 7.8 |

BIOMARKERS FOR THE PREDICTION AND IDENTIFICATION OF PARKINSON'S DISEASE

CROSS-REFERENCE TO RELATED APPLICATIONS

This application is the National Stage of International Application No. PCT/GB2020/052872, filed Nov. 11, 2020, which claims priority to GB 1916390.6, filed Nov. 11, 2019, GB 1916388.0, filed Nov. 11, 2019, GB 2002290.1, filed Feb. 19, 2020, and GB 2002289.3, filed Feb. 19, 2020, which are entirely incorporated herein by reference.

FIELD OF THE INVENTION

The invention relates to biomarkers useful in the prediction and identification of a subject having Parkinson's Disease. The invention also relates to methods of measuring the levels of the biomarkers.

BACKGROUND TO THE INVENTION

Parkinson's disease (PD) is the most common movement disorder with a long prodromal phase (1,2) and risk of progression to dementia (3). These disease phases broadly correlate with the evolution of Lewy body and neuritic pathology (4), which involves the accumulation and aggregation of α-synuclein (5).

The earliest phase of PD is also referred to as preclinical PD, during which neurodegeneration has started but without evident symptoms or signs of the disease. The disease then progresses to a prodromal phase, during which the symptoms and signs of the disease are present, but are yet insufficient to define disease. The prodromal phase is notably long (more than 10 years in many patients) and surprisingly diverse, with multiple non-motor and motor symptoms, including hyposmia, anxiety, constipation, fatigue and subtle motor slowing. Clinical diagnosis of PD is typically made upon the presence of classical motor signs, and the three cardinal motor manifestations of PD are rest tremor, rigidity, and bradykinesia.

However, there is an appreciable misdiagnosis rate of PD, and on the other hand, many patients with PD in the community remain undiagnosed. Definitive diagnosis of the disease can only be made upon autopsy. In the early stages of the disease, PD and other forms of degenerative parkinsonism share common features and clinical distinction may be difficult (6).

Currently there is no test in clinical practice that can either predict risk or reliably distinguish PD from unrelated neurodegenerative conditions. Such a test would provide significant clinical benefit by enabling more accurate diagnosis of PD at an early stage, and so appropriate treatment therapies can begin early, thereby providing the individuals with a greater chance of maintaining longer-term independence and a high quality of life.

Given that abnormal α-synuclein accumulation is a primary component of PD pathology, α-synuclein has been studied as a potential biomarker for diagnosis of PD and/or indication of disease progression. α-Synuclein can be found in the cerebrospinal fluid (CSF). Although cerebrospinal fluid (CSF) total α-synuclein was found to be reduced in patients with PD compared to controls (7), meta-analyses showed an unsatisfactory diagnostic accuracy with a pooled sensitivity between 78-88% and a specificity between 40-57% (8). Furthermore, the invasive nature of CSF sample collection by lumbar puncture means that this approach is not ideal for routine monitoring.

α-Synuclein can also be found in the peripheral fluids (9). The concentration of α-synuclein in blood is strongly influenced by red blood cells, which are the source of >99% of the protein (10). For this reason, blood content of free total α-synuclein in PD patients is of limited utility (11), partly due to contamination with red cell haemolysis.

α-Synuclein can be found associated with exosomes. Circulating exosome composition and function are altered in PD (12). Although the reports on whether the total exosomal α-synuclein content was increased in PD patients have been inconsistent (12, 13, 14), the analysis of the population of exosomes that were released from neuronal tissues (i.e. plasma neuron-derived exosomes) in plasma showed that α-synuclein content was increased in PD patients with a weak correlation with disease severity (15). However, this study merely indicates the usefulness of α-synuclein as a biomarker in patients that have already been diagnosed with PD.

There is a need for new, minimally invasive tests to provide accurate diagnosis of PD at an early stage, in particular with improved discriminatory power between PD and other forms of degenerative parkinsonism. It is an objective of the invention to meet these needs.

SUMMARY OF THE INVENTION

The inventors surprisingly identified that certain proteins in the exosomes that were released from neuronal tissues (i.e. neuron-derived exosomes) in the blood can be useful as biomarkers of Parkinson's disease, and particularly in the early phases of the disease. In particular, the inventors found that increased α-synuclein egress in serum neuronal exosomes precedes the diagnosis of PD and persists with disease progression. In combination with clusterin, α-synuclein is a predictive marker of an evolving α-synucleinopathy that could be considered clinically in the stratification of at-risk patient groups or monitoring of α-synuclein-targeting therapies.

The inventors assessed the protein content of neuron-derived exosomes in blood samples from subjects having neurodegenerative conditions across the spectrum of Lewy body pathology, i.e. conditions characterised by α-synucleinopathy including early to late stages of PD, and neurodegenerative conditions characterised by non-α-synuclein proteinopathy (e.g. frontal temporal dementia (FTD), progressive supranuclear palsy (PSP) and corticobasal syndrome (CBS)). The inventors found that, in the neuron-derived exosomes in the blood, mean α-synuclein content was increased by 2-fold ($p<0.0001$) in prodromal and clinical PD when compared to controls or other neurodegenerative conditions. With 314 subjects in the training group and 105 in the validation group, α-synuclein content in the neuron-derived exosomes in the blood exhibited a consistent performance (AUC=0.86) in separating clinical PD from controls across populations. Longitudinal sample analyses showed that α-synuclein in the neuron-derived exosomes in the blood remains stably elevated with PD progression, contrary to previous observations (15).

Without wishing to be bound by theory, the data suggest that jettison of α-synuclein from neuronal tissues is a specific pathophysiological response in PD that precedes the clinical diagnosis and persists with disease progression. Therefore, α-synuclein can be a useful biomarker for predicting PD and discriminating a condition characterised by α-synuclein (such as PD and related conditions (e.g. PD with dementia and MSA)) from a condition characterised by non-α-synuclein proteinopathy.

Furthermore, the inventors found that clusterin content in the neuron-derived exosomes in the blood was elevated in subjects having neurodegenerative conditions characterised by non-α-synuclein proteinopathy (e.g. frontal temporal dementia (FTD), progressive supranuclear palsy (PSP) and corticobasal syndrome (CBS)) ($p<0.0001$), but not in subjects with Lewy body pathology, i.e. having conditions characterised by α-synucleinopathy (e.g. prodromal, motor and dementing stage of PD). Therefore, clusterin can be a useful biomarker for predicting and diagnosing neurodegenerative conditions characterised by non-α-synuclein proteinopathy, in particular tauopathy.

Combined α-synuclein and clusterin measurements in the neuron-derived exosomes in the blood distinguished subjects having an underlying α-synucleinopathy versus non-α-synuclein proteinopathies with AUC=0.98. Thus, clusterin may be used in combination with α-synuclein to improve the diagnostic power for predicting PD, and for discriminating a condition characterised by α-synuclein (such as PD and related conditions (e.g. PD with dementia and MSA)) from a condition characterised by non-α-synuclein proteinopathy.

The inventors also found that mean exosomal α-synuclein was increased by 2-fold in prodromal and clinical Parkinson's disease when compared to MSA. Furthermore, combined neuron-derived exosomal α-synuclein and clusterin measurement predicted Parkinson's disease from MSA with AUC=0.94. Thus, exosomal α-synuclein alone or in combination with clusterin may also be used in discriminating PD from its related conditions, e.g. conditions having similar signs and symptoms, such as atypical parkinsonian syndromes including MSA.

Thus, the invention provides a method for analysing a blood sample from a subject, comprising determining the levels of α-synuclein and clusterin in the neuron-derived exosomes in the blood sample, wherein the levels of α-synuclein and clusterin provide a diagnostic indicator of a subject susceptible to PD or of a subject having PD.

The invention also provides method for analysing a blood sample from a subject, comprising determining the levels of α-synuclein and clusterin in the neuron-derived exosomes in the blood sample.

The invention also provides a method for analysing a blood sample from a subject having one or more signs or symptoms of parkinsonism and who has not been diagnosed with PD, comprising determining the level of α-synuclein in the neuron-derived exosomes in the blood sample, wherein the level of α-synuclein provides a diagnostic indicator of the subject being susceptible to PD.

The invention also provides a method for discriminating a condition characterised by α-synuclein (such as PD and related conditions (e.g. PD with dementia and MSA)) from a condition characterised by non-α-synuclein proteinopathy, comprising analysing a blood sample from a subject according to any of the methods of the invention.

The invention also provides a method for discriminating PD from its related conditions, such as atypical parkinsonian syndromes including MSA, comprising analysing a blood sample from a subject according to any of the methods of the invention.

The invention also provides method for identifying a subject susceptible to PD, comprising analysing a blood sample from the subject according to any of the methods of the invention.

The invention also provides method of preventing and/or treating PD in a subject, comprising identifying a subject susceptible to PD according to any of the methods of the invention, and treating the subject with a therapy for PD.

The invention also provides a method of monitoring the efficacy of a α-synuclein-targeting therapy, such as a therapy for PD, being administered to a subject, comprising analysing a blood sample from the subject according to a method of the invention, wherein each biomarker is determined at two or more different points in time, with changing levels of each biomarker over time indicating whether the disease is getting better or worse.

The methods described above require the extraction of a selected population of exosomes from a blood sample, and the analysis of the content of certain proteins in the exosomes. Immunoassays which involve binding to exosomes have been described in the art. For instance, reference 16 describes a method which involves immunoaffinity beads designed to capture exosomes via recognition of epithelial cell adhesion molecule (EpCAM), an exosomal biomarker protein. The beads are coated with polyacrylic acid to provide functional binding sites, and then conjugated with sulfobetaine, an antifouling zwitterion. Anti-EpCAM antibody is then conjugated to the sulfobetaine molecules.

However, the present inventors found that determining the levels of specific proteins within neuronal exosomes, using such prior art methods, e.g. as described in 15, was not sufficiently accurate to provide a useful diagnostic indicator predictive of PD. In particular, the present methods require isolation of only a particular selected population of exosomes. This requires an assay with a high level of specificity for the desired exosomes. Further, the determination of the levels of certain proteins within this selected population of exosomes requires the exosome sample to be extracted with very low levels of interfering biological molecules. The inventors therefore recognised that the existing methodologies would not be sufficient to study the protein content of neuron-derived exosomes, and improved methods for selectively isolating this population of exosomes from blood samples would be needed.

The present inventors determined that a greater selectivity for the desired exosomes could be achieved by growing zwitterionic polymers on the surface of a particle and conjugating ligands having affinity for a selected population of exosomes to the zwitterionic polymers. The invention therefore also provides a coated particle having a coating comprising a zwitterionic polymer coupled to a ligand having affinity for a selected population of exosomes.

The invention also provides a method of isolating exosomes from a sample, comprising steps of: contacting the sample with the coated particle of the invention; removing unbound sample; and separating the captured exosomes.

Zwitterionic materials are effective at preventing nonselective binding of biologic materials, due to their ability to bind to water molecules and provide a high degree of hydration. The coated particles described herein have a high surface coverage of zwitterionic polymer, minimising any available surface to which biologic molecules might bind. Further, the polymers are typically grown outwards from the surface of the polymer in brush-like fashion. This provides a higher degree of hydration around the particle than is achieved using a coating of non-polymeric zwitterionic molecules. It also achieves a high degree of conformational entropy due to the movement of the polymer chains. All of these factors provide coated particles which are very effective at minimising interaction with nonspecific biologic molecules.

Attaching zwitterionic polymers to small particles such as nanoparticles is non-trivial. Thus, earlier methods for isolating exosomes used simpler processes, for example involving the attachment of single layers of zwitterionic molecules. The present inventors, however, identified a need for greater selectivity, without which the predictive value of the identified markers is significantly reduced. The coated particles and methods for capturing exosomes, as described herein, provide effective isolation of the desired exosomes, thus enabling accurate determination of their protein content. Using these methods, exosomal protein content can be measured to pg/mL levels.

The invention also provides a kit comprising coated particles of the invention for isolating a selected population of exosomes from a blood sample and/or reagents for determining the levels of α-synuclein and clusterin in the neuron-derived exosomes in a blood sample.

The invention also provides the use of α-synuclein and optionally clusterin as biomarker(s) to provide a diagnostic indicator of a subject being susceptible to PD, to discriminate a condition characterised by α-synuclein (such as PD and related conditions (e.g. PD with dementia and MSA)) from a condition characterised by non-α-synuclein proteinopathy, and/or to discriminate PD from its related conditions, such as atypical parkinsonian syndromes including MSA.

The invention also provides the use of α-synuclein and clusterin as biomarkers to provide a diagnostic indicator of a subject having Parkinson's disease.

The invention also provides the use of clusterin as a biomarker to provide a diagnostic indicator of a subject being susceptible to or having tauopathy.

The invention also provides a method for analysing a blood sample from a subject, comprising a step of determining the level of clusterin in the neuron-derived exosomes, wherein an increase in the level of clusterin provides a diagnostic indicator of a subject being susceptible to or having tauopathy.

The invention also provides a method for analysing a blood sample from a subject, comprising a step of determining the level of clusterin in the neuron-derived exosomes.

(B) Ratio of α-synuclein to clusterin improved the separation between α-synucleinopathies and alternative proteinopathies. Receiver operating characteristic (ROC) analysis of individual markers and their ratio or linear regression analysis of composite measurements revealed an improved predictive power of the two biomarkers in differentiating prodromal or clinical PD from alternative proteinopathies as shown in panels C and D. Clinical PD refers to the combined group of PD and PDD ($^{*}p<0.001$, $^{**}p<0.0001$).

FIG. 3 shows the estimation of cut-off values of α-synuclein in the neuron-derived exosomes in the blood between cohorts. Boxplots of mean exosomal α-synuclein levels and corresponding ROC curves in training (A) and validation groups (B). When an exosomal α-synuclein cut-off value ≥14.21 pg/mL estimated from the training group (Keil and Brescia) was applied to the validation group (Oxford), assay performance analysis revealed a consistent result across populations with similar area under a curve (AUC), Sensitivity (Sens), specificity (Spec), positive (PPV) and negative (NPV) predictive values in distinguishing clinical PD from controls as shown in panel C.

FIG. 4 shows the longitudinal analysis of α-synuclein and clusterin content in the neuron-derived exosomes in the blood of the samples. Linear mixed model of exosomal α-synuclein (A) and clusterin (B) was fitted to the longitudinal values with time from first sampling as a covariant, and patients stratified by level at initial visit in relation to median value. Persistent separation between disease subgroups and controls but no overall significant difference in the gradient from zero was identified when comparing clinical PD to control samples. Clinical PD refers to the combined group of PD and PDD. Patient characteristics and p values are summarized in panel C.

Figure 5:
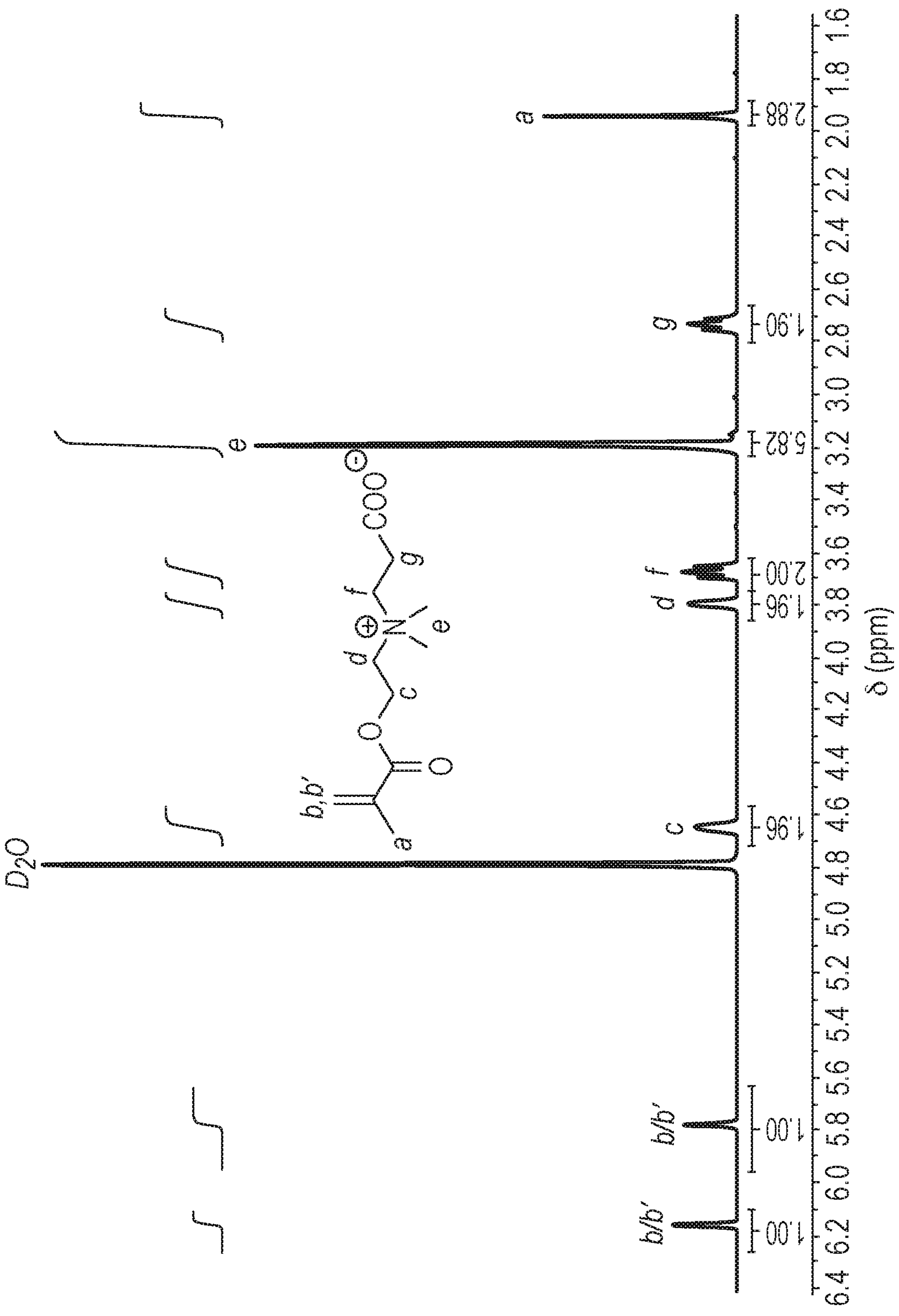

FIG. 5 shows the molecular structure of carboxybetaine methacrylate (CBMA) monomer and nuclear magnetic resonance (NMR) spectrum of CBMA in $D_2O$.

FIG. 6 (A) Fourier transform infrared spectroscopy-attenuated total reflection (FTIR-ATR) spectrum of pCBMA coated beads with bare iron oxide beads and CBMA monomer used as controls. Reduced adsorption of BSA (B) or serum proteins (C) on pCBMA coated beads compared to commercially available epoxy beads, both conjugated to anti-HA antibodies FIG. 7 shows pCBMA-based zwitterionic magnetic bead preparation and exosome immunocapture. (A) Synthesis and application of pCBMA coated magnetic microbeads for immunocapture of L1 CAM-positive neuronal exosomes in serum. (B) SEM of anti-L1CAM conjugated or control pCBMA coated beads demonstrating immunocapture of exosomes from serum (scale bar, 200 nm). (C) Lysates of immunocaptured vesicles contain transmembrane (CD81 and L1 CAM) and internal exosomal proteins (Tsg101 and Syntenin-1) as shown by immunoblotting. (D) GO analysis of proteins identified by mass spectrometry revealed terms enriched in exosomes and related extracellular vesicle functions. (E) List of bona fide exosomal proteins and top hits identified by mass spectrometry.

Figure 8A:
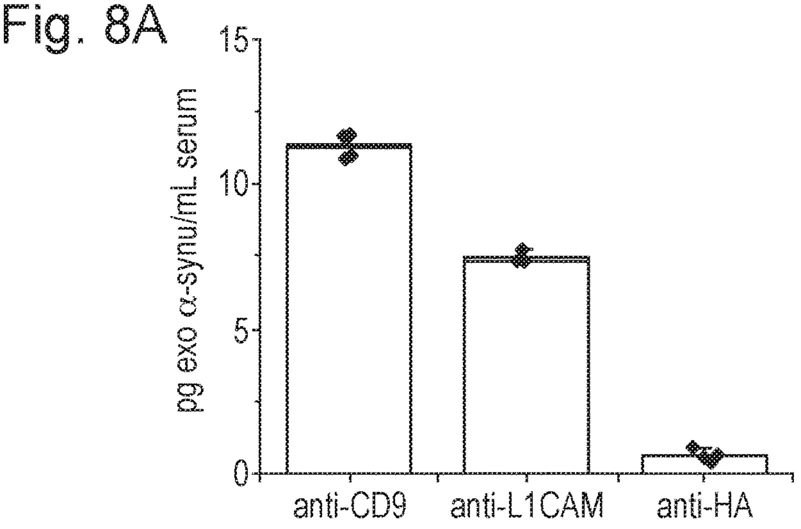
Figure 8B:
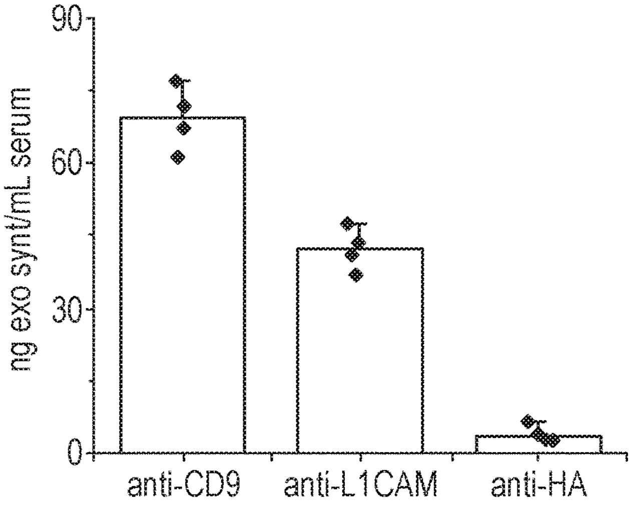
Figure 8C:
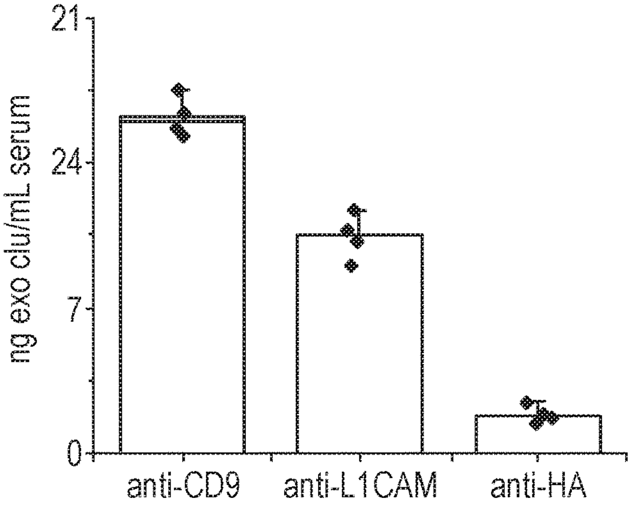

FIG. 8 shows specific detection by triplex electrochemiluminescence of α-synuclein (A), syntenin-1 (B) and clusterin (C) in serum exosomes immunocaptured with anti-CD9 (total exosome population), anti-L1CAM (neuronal exosome subpopulation) or anti-HA (control antibody against epitope not present on exosomes).

Figure 9A:
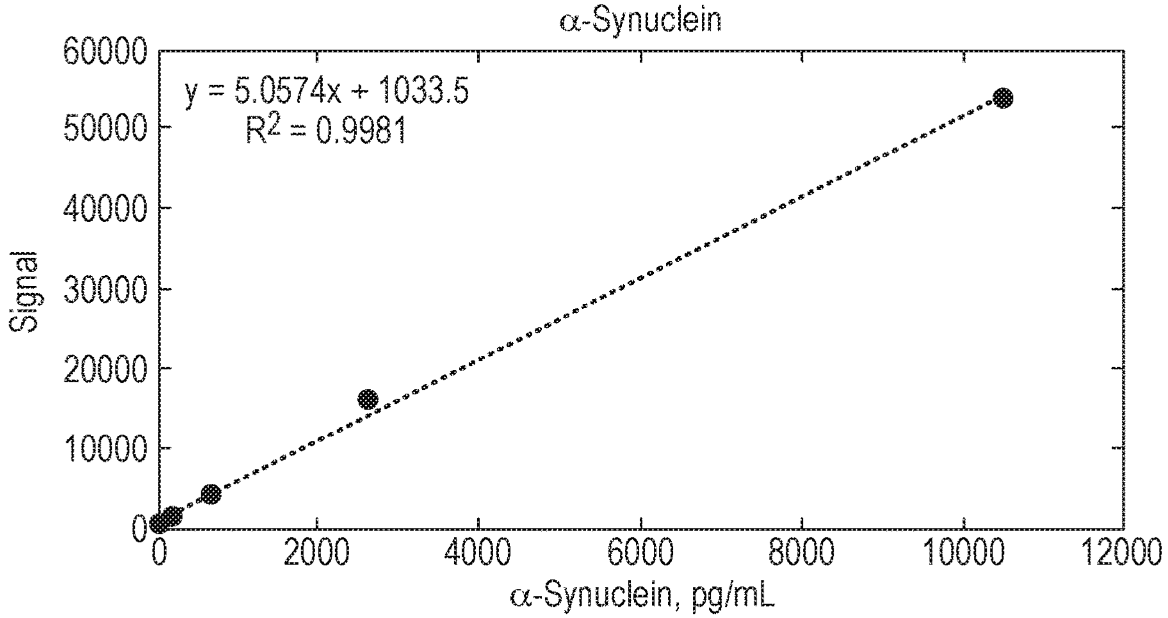
Figure 9B:
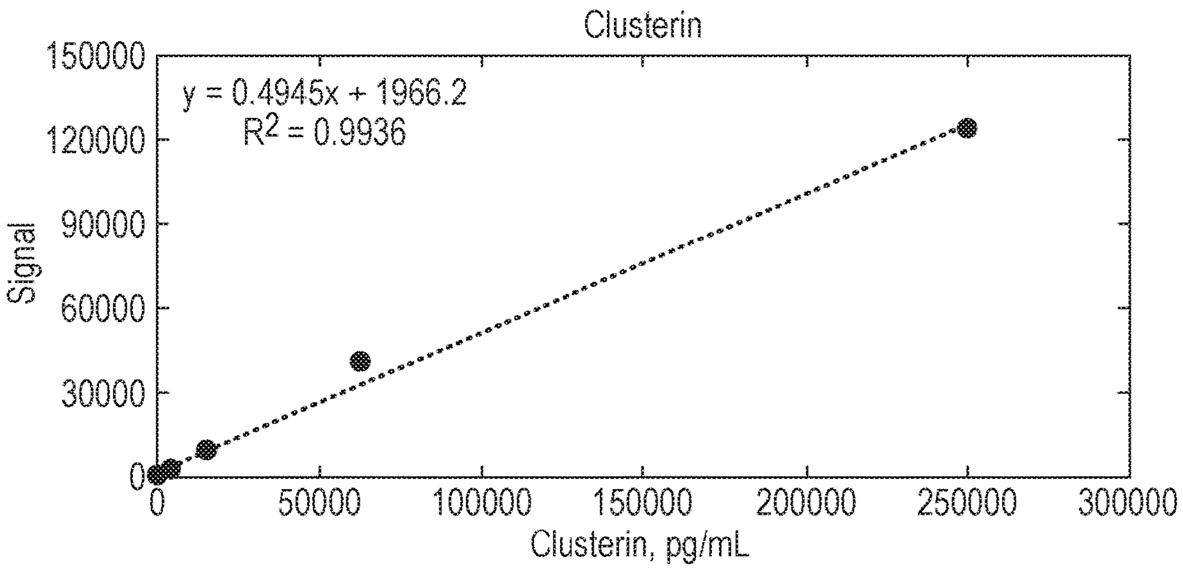
Figure 9C:
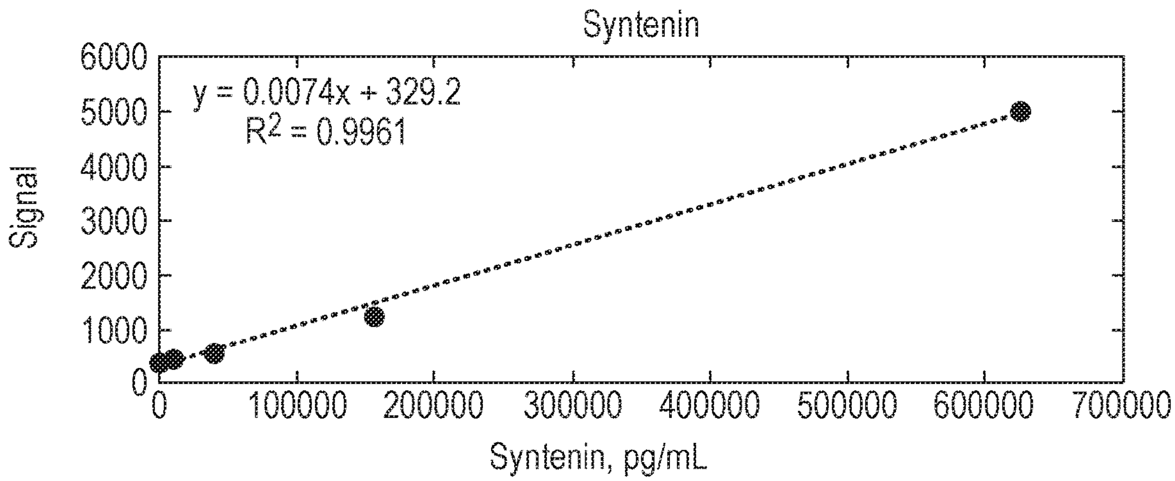

FIG. 9 shows syntenin-1 content in the neuron-derived exosomes in the blood of the samples from subjects across disease groups. No disease-specific pattern of distribution was detected across groups that could significantly contribute to biomarker development.

Figures 10A, 10B:
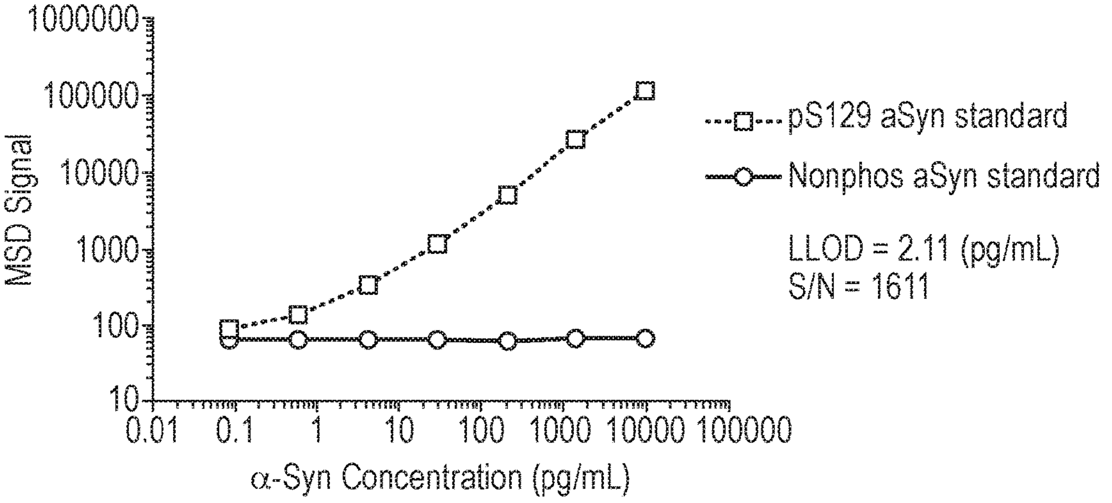
Figure 10C:
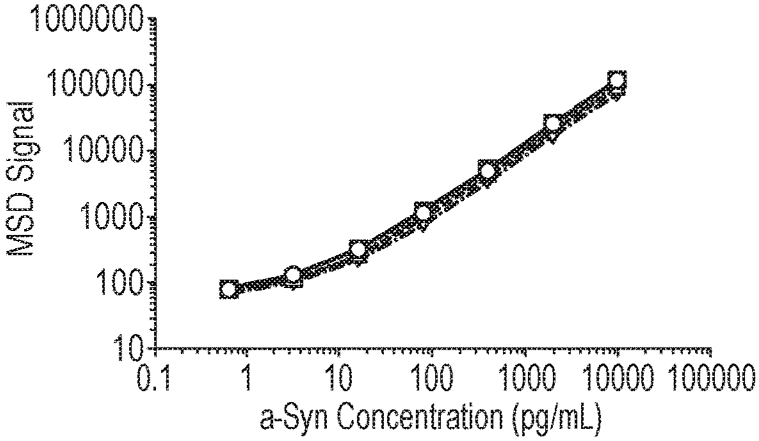

FIG. 10 shows the electrochemiluminescence assay development for the detection of pSer129 α-synuclein. (A) Information for antibody pairs used, (B) specificity test and (C) reproducibility. The LLOD for pSer129 α-synuclein is 2.11 pg/mL. It should be pointed out that proteins in exosomal lysates were 10 times concentrated: 500 μL of serum input was used for exosomes capture, lysed in 50 μL lysis buffer (concentration factor is 10). The calibration curve was used to detect biomarker in the lysates, for example, if the marker's concentration in lysates is 5 pg/mL, then the marker's concentration in serum is 5/10 pg/mL=0.5 pg exosomal marker/mL serum. For the pSer129 α-synuclein, the LLOD is 2.11 pg/mL in lysates and 0.211 pg/mL exosomal pSer129 α-synuclein in serum. Therefore, 0.5 pg/mL was considered as a cut-off for detection of exosomal pSer129 α-synuclein in serum to compare results between groups.

Figure 11:
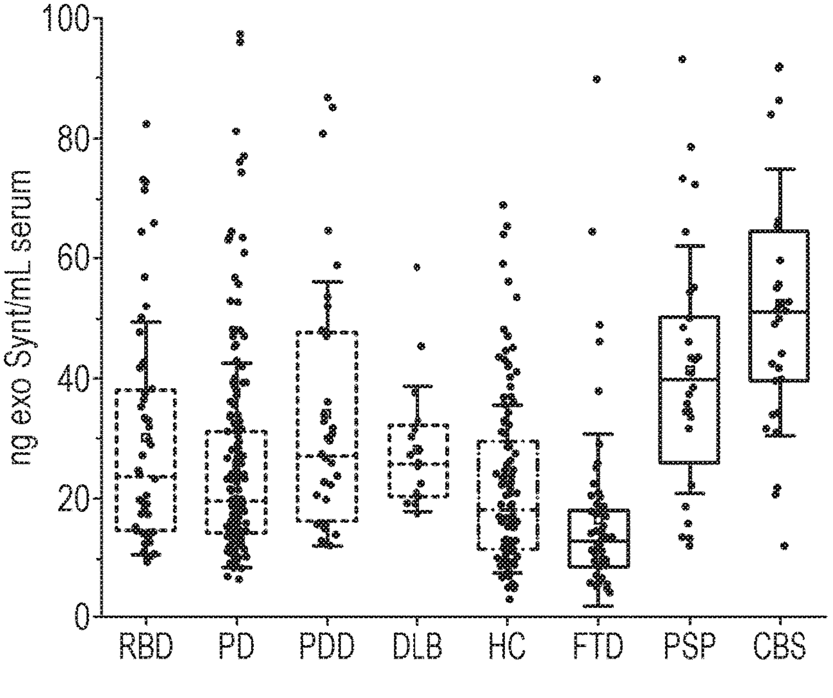

FIG. 11 shows the exosomal syntenin-1 levels across disease groups. No disease-specific pattern of distribution was detected across groups that could significantly contribute to biomarker development.

Figure 12:
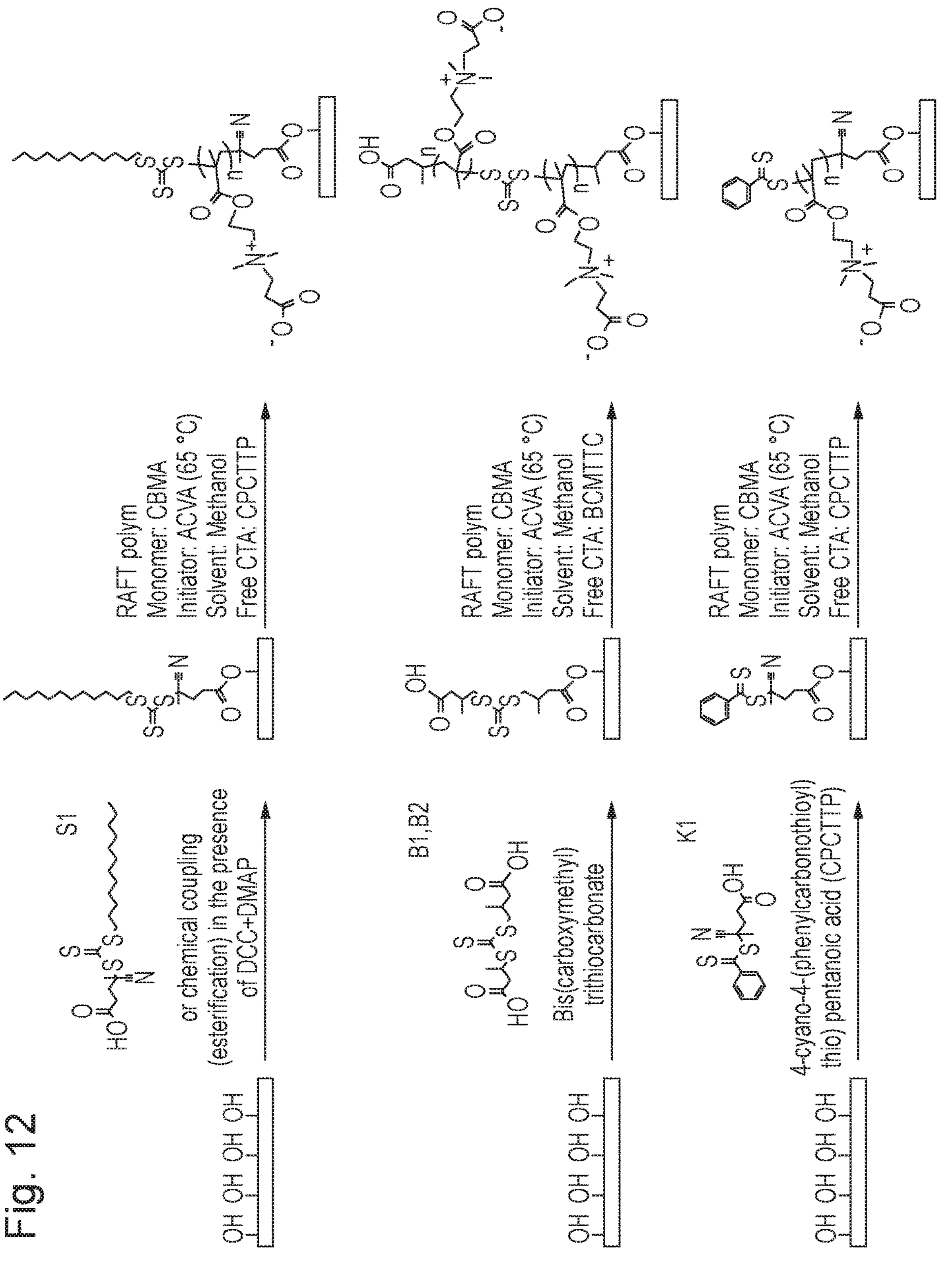

FIG. 12 provides exemplary methods for carrying out surface initiated RAFT polymerisation on a surface of a particle.

FIG. 13 shows that neuron-derived exosomal α-synuclein is increased across the spectrum of Lewy body pathology. (A) Boxplots of mean total α-synuclein across the spectrum of conditions with Lewy body pathology (RBD, motor PD, PDD, DLB), MSA and unrelated neurodegenerative diseases (FTD, PSP, CBS) as well as age- and sex-matched controls. Two-fold increase in the content of α-synuclein was detected in L1 CAM-positive exosomes isolated from conditions characterized by Lewy body pathology. (B) At the lowest detectable concentration (0.32 pg/ml), pSer129 α-synuclein was detected in a subgroup of PD patients that were tested (55.8%). No significant correlation was seen between total exosomal α-synuclein and either UPDRS (panel C, r=0.0267) or MoCA (panel D, r=0.0621) in PD patient samples. $^{}p<0.01$, $^{*}p<0.001$, $^{****}p<0.0001$. Mean values with interquartile range of exosomal markers and whisker range using SD with coefficient of 1 were used in the boxplots.

FIG. 14 shows that neuron-derived exosomal clusterin is increased in tauopathies and when combined with α-synuclein improved the differential diagnosis. (A) Clusterin (clu) release in serum neuronal exosomes is increased in FTD, PSP and CBS but not RBD, PD, PDD, DLB, MSA or age- and sex-matched controls. (B) Ratio of α-synuclein to clusterin improved the separation between Lewy body pathology and alternative proteinopathies. (C) Heatmap illustration of exosome profiles using α-Syn, Clu or α-Syn/Clu differentiating between diseases. The change in the concentration of each exosome marker was normalized to the value of HC. ROC analysis of individual markers and their ratio or linear regression analysis of composite measurements revealed an additive effect of the two biomarkers in differentiating prodromal or clinical PD from alternative proteinopathies as shown in panels D and F or MSA as shown in panels E and G. Clinical PD refers to the combined group of PD and PDD ($^{}p<0.01$, $^{*}p<0.001$, $^{****}p<0.0001$).

Figure 15:
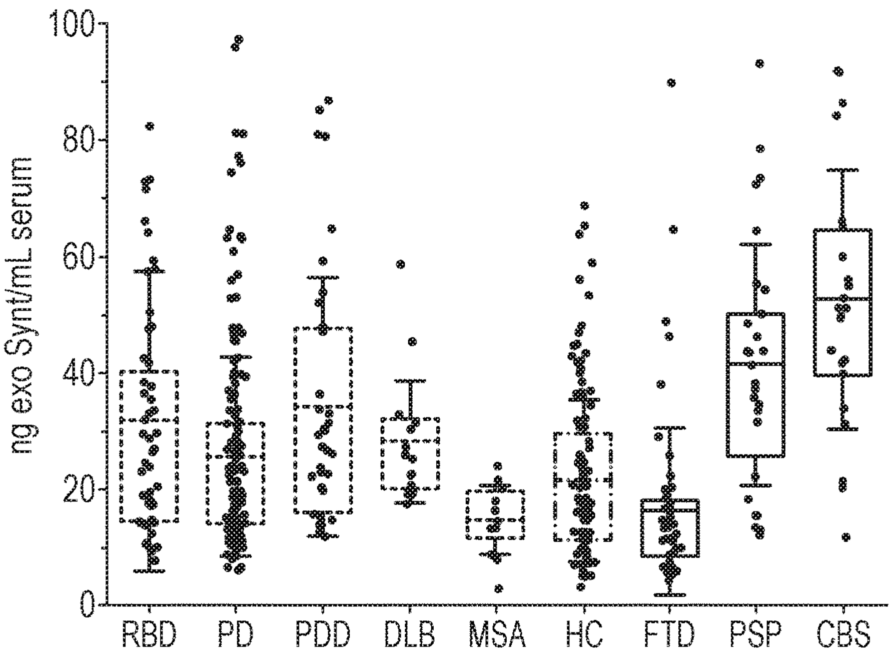

FIG. 15 shows the exosomal syntenin-1 levels across disease groups. No disease-specific pattern of distribution was detected across groups that could significantly contribute to biomarker development.

Figure 16:
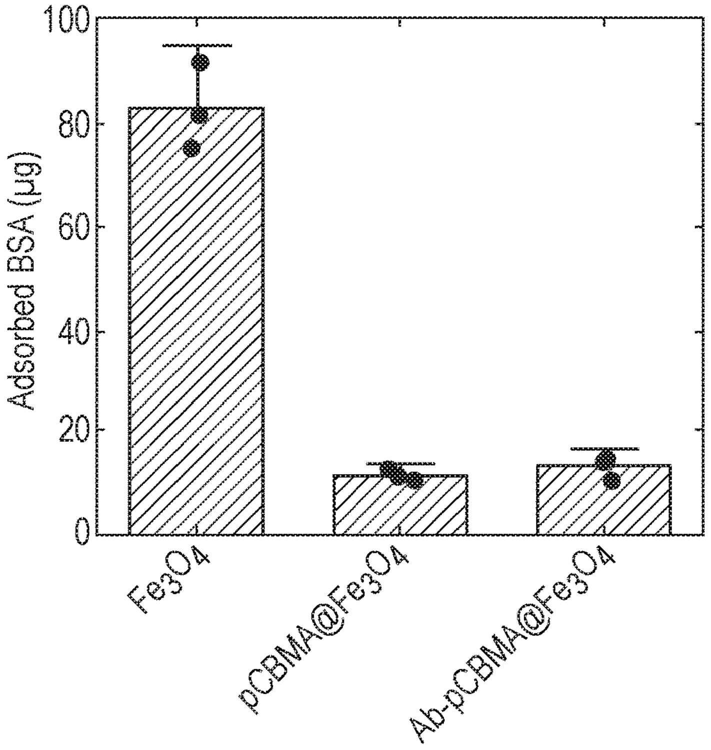

FIG. 16 contains a histogram depicting a quantitative assessment of adsorbed BSA on different magnetic bead (MB) surfaces (1 mg beads input). The error bar represents the standard deviation of three distinct collected experimental data sets.

Figure 17A:
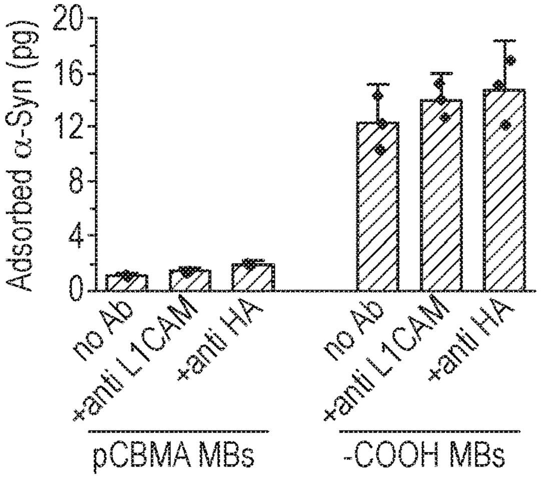
Figure 17B:
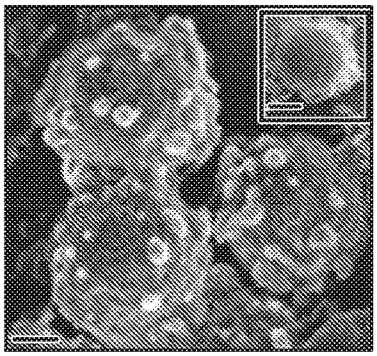

FIG. 17 contains FIGS. 17A, B, C and D. (A) is a histogram depicting the quantified adsorption of recombinant α-Syn on different Ab-modified pCBMA@$Fe_3O_4$ MBs surfaces. The commercial carboxylic acid-terminated MBs were used as the control. (B) is an SEM image of serum-captured exosomes on anti-L1CAM-modified MBs versus anti-HA (control)-modified MBs (insert). Scale bar 1 μm. (C) shows immunoblotting of lysates of immunocaptured vesicles confirming the detection of both trans-membrane proteins (L1CAM, CD81) and internal protein Synt-1 from exosomes. Specific electrochemiluminescence detection of α-Syn (D) in neuronal exosomes immunocaptured from serum with anti-L1CAM vs anti-HA (control)-modified pCBMA@$Fe_3O_4$ MBs FIG. 18 shows relative responses of anti-Synteinin-1 modified sensor to $10^{-3}$ g/mL of CRP, $10^{-3}$ g/mL of α-Syn, $10^{-3}$ g/mL of BSA and $10^{-9}$ g/mL Synt-1. The error bars were calculated from 9 measurements: triplicate repeats across three experiments using 3 independent working electrodes.

Figure 19A:
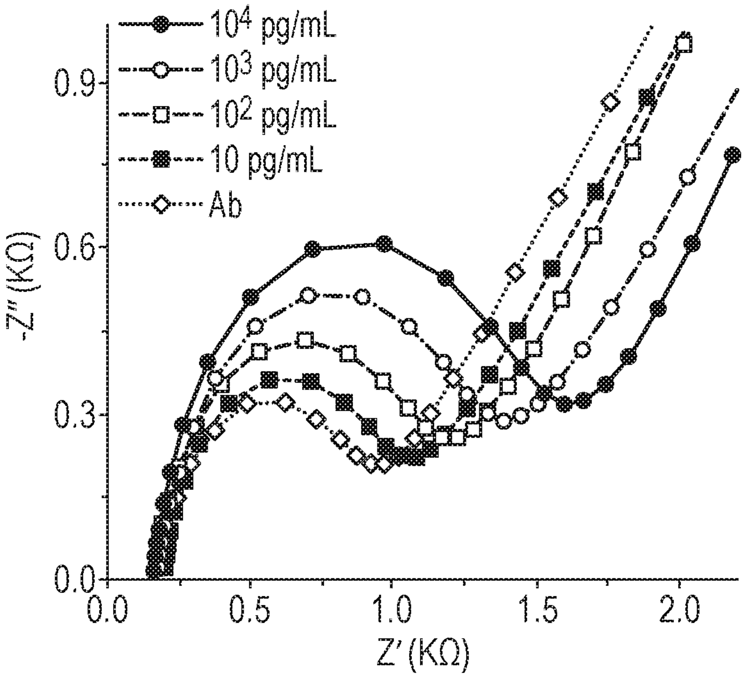
Figure 19B:
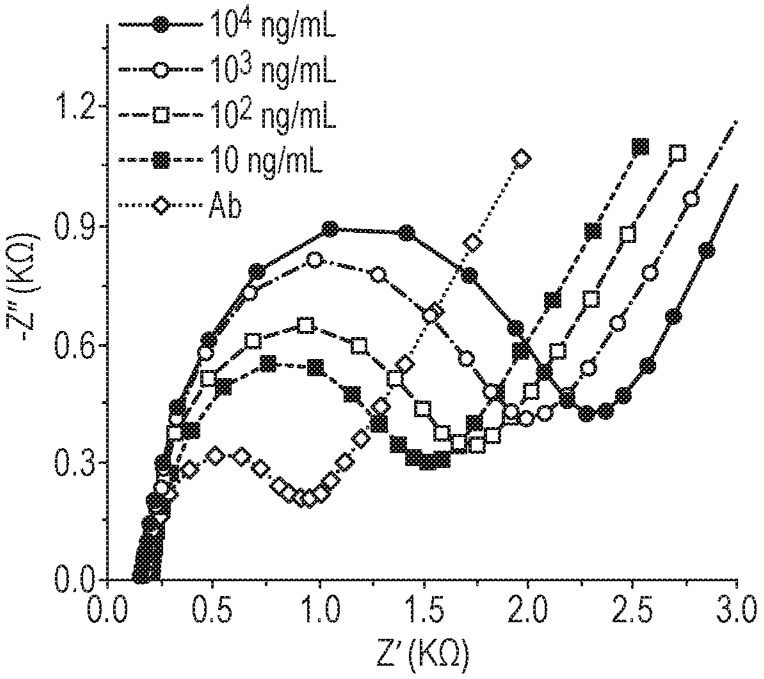

FIG. 19 shows Nyquist curves of (A) anti-α-Syn modified working electrode to α-Syn spiked into 10% human serum and (B) anti-Synteinin-1 modified working electrode to Synt-1 spiked into 10% human serum with varying concentrations as shown.

Figure 20A:
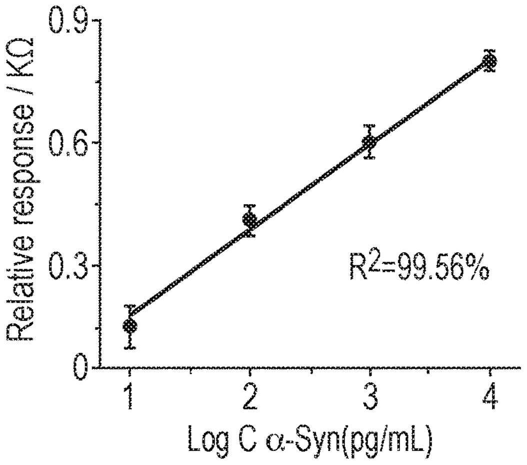
Figure 20B:
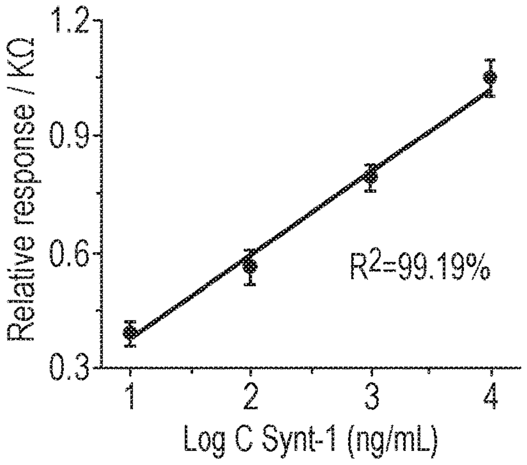

FIG. 20 shows impedimetric calibration curves for (A) α-Syn spiked into 10% human serum with a dynamic range from 10 to 104 pg/mL, and (B) Synt-1 spiked into 10% human serum in a concentration range of 10 to 104 ng/mL. The error bars were calculated from 9 measurements: triplicate repeats across three experiments using 3 independent working electrodes.

Figure 21:
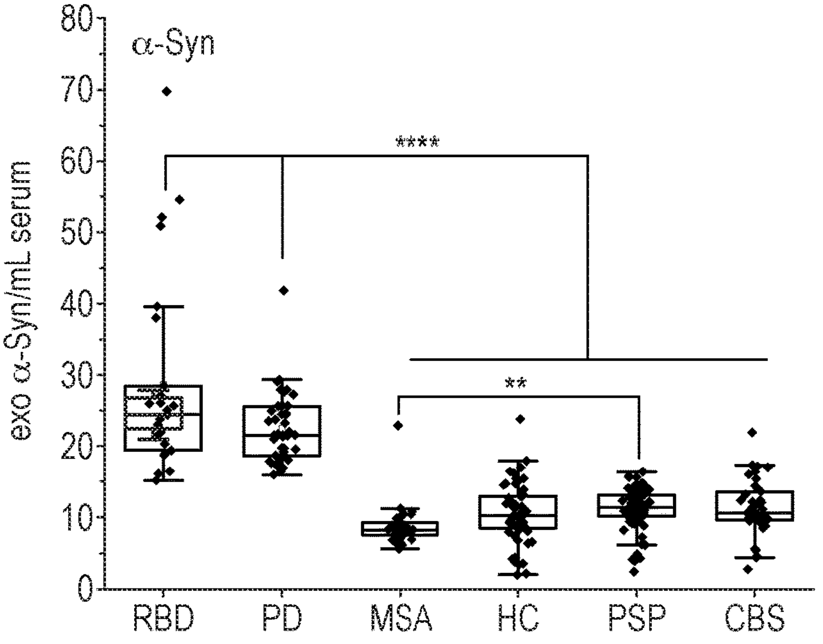
Figure 22A:
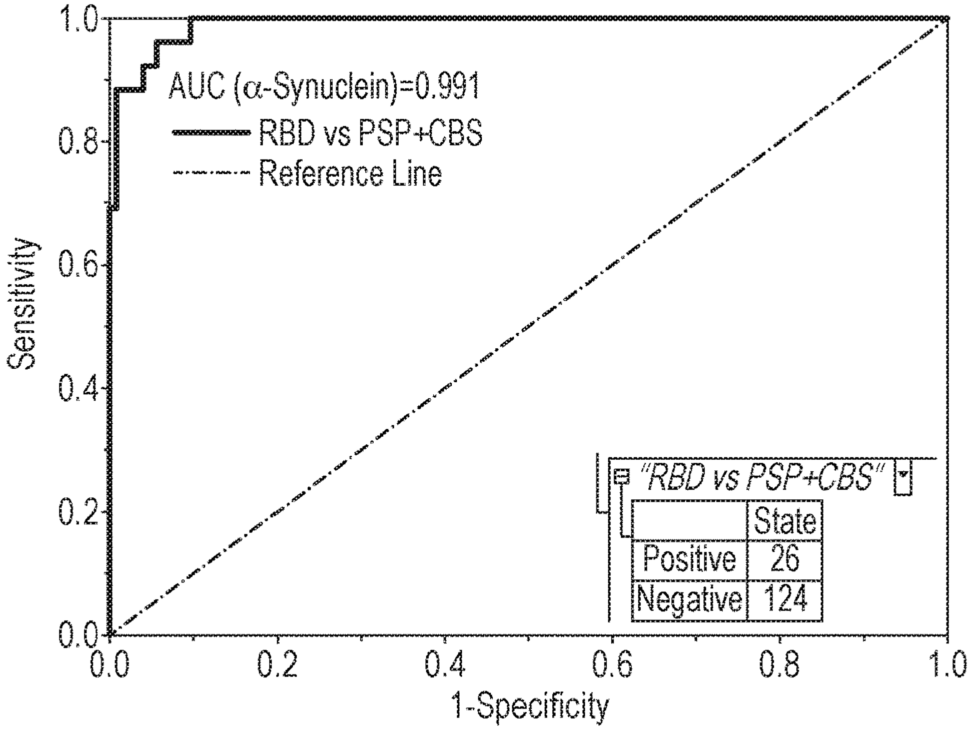
Figure 22B:
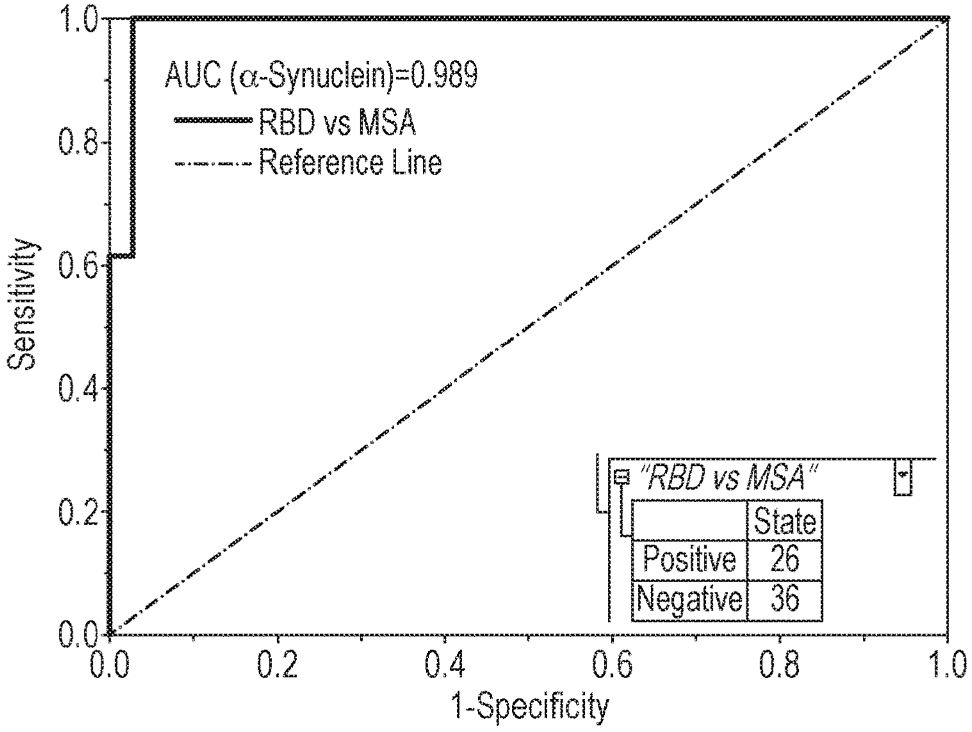
Figure 22C:
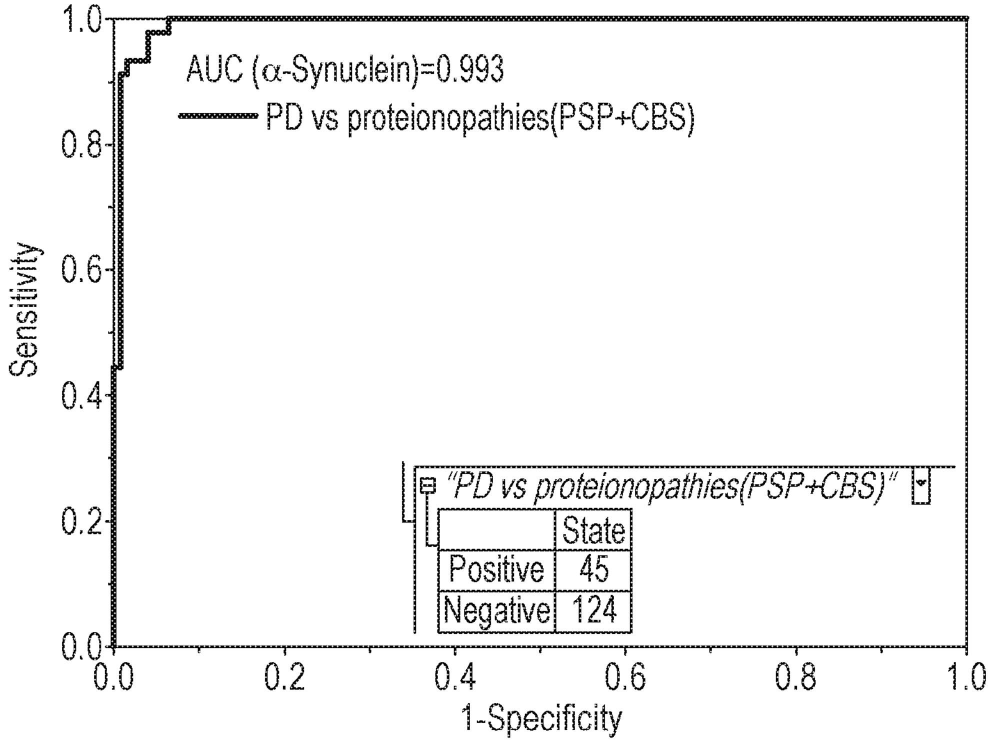
Figure 22D:
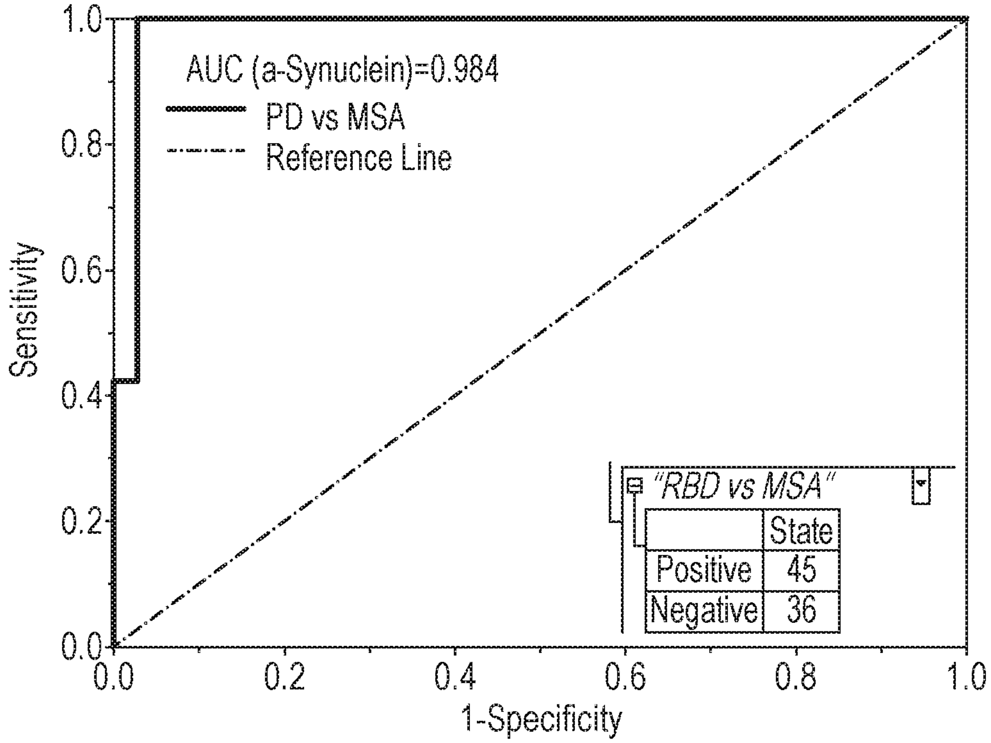

FIG. 21 shows a box plot of α-Synuclein level across different disease groups and healthy control group. $^{}P<0.01$, $^{*}P<0.001$, $^{****}P<0.0001$. Mean values with IQR of exosomal markers and whisker range using SD with coefficient of 1 were used in the boxplots.

FIG. 22 shows ROC curves represent the diagnostic mode using α-Synuclein as feature for the separation of (A) RBD vs PSP+CBS, (B) RBD vs MSA, (C) PD vs PSP+CBS, (D) PD vs MSA.

Figure 23:
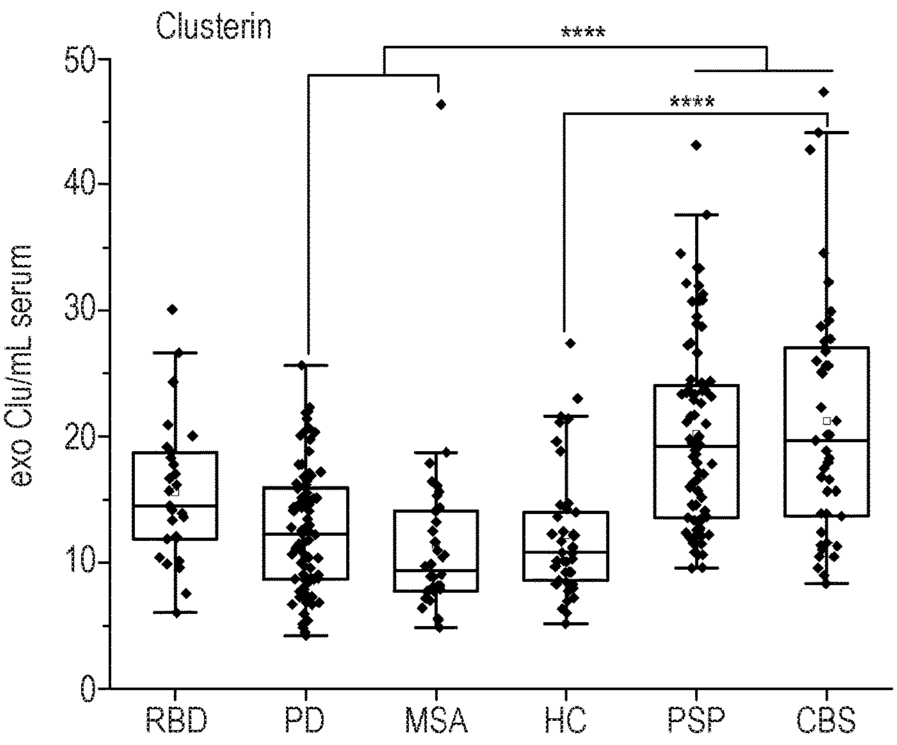

FIG. 23 shows a box plot of Clusterin level across different disease groups and healthy control group. $^{}P<0.01$, $^{*}P<0.001$, $^{****}P<0.0001$. Mean values with IQR of exosomal markers and whisker range using SD with coefficient of 1 were used in the boxplots.

Figure 24:
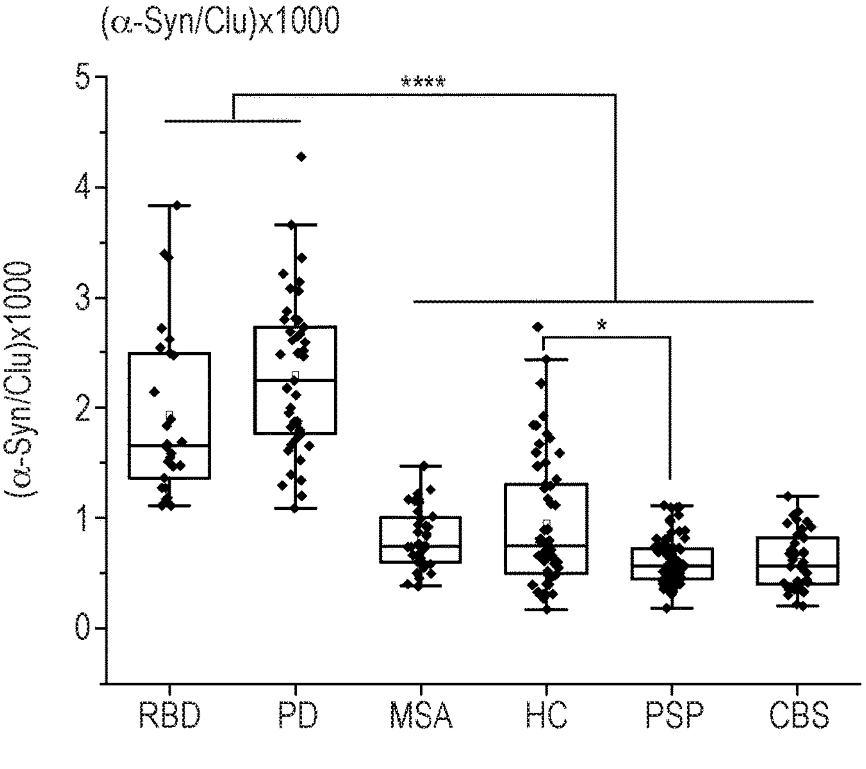
Figure 25A:
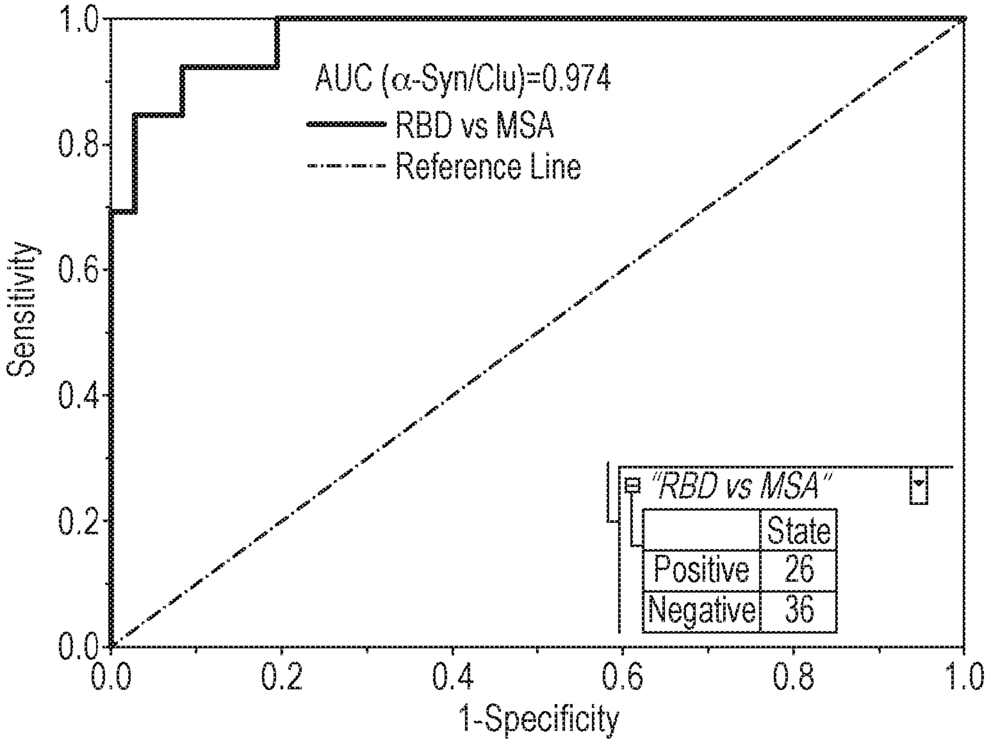
Figure 25B:
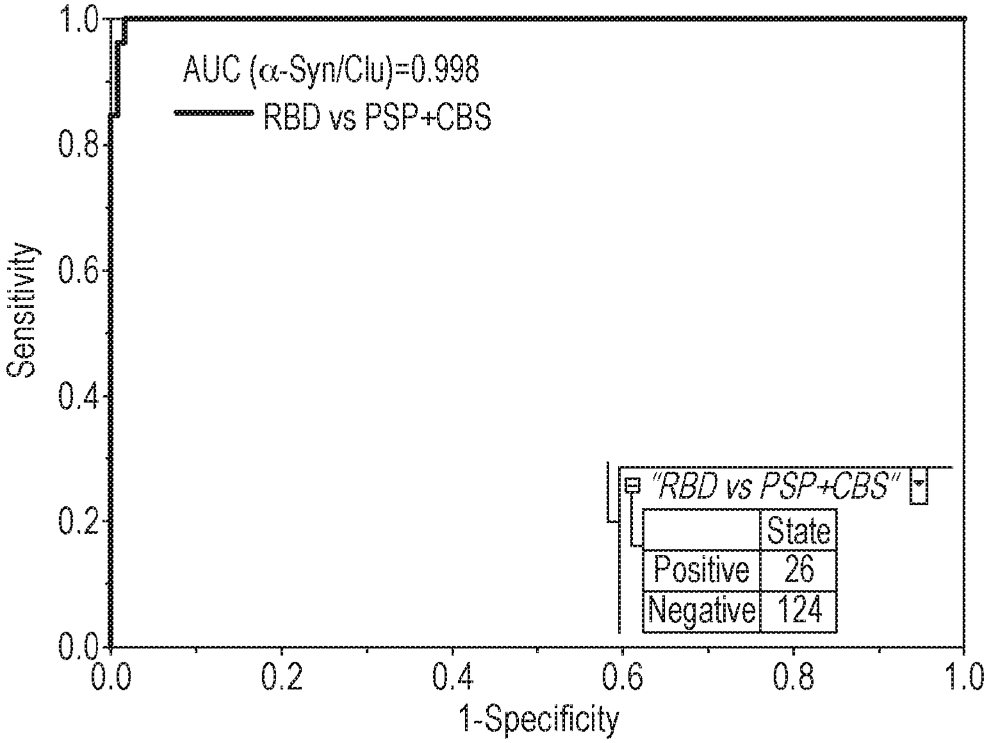
Figure 25C:
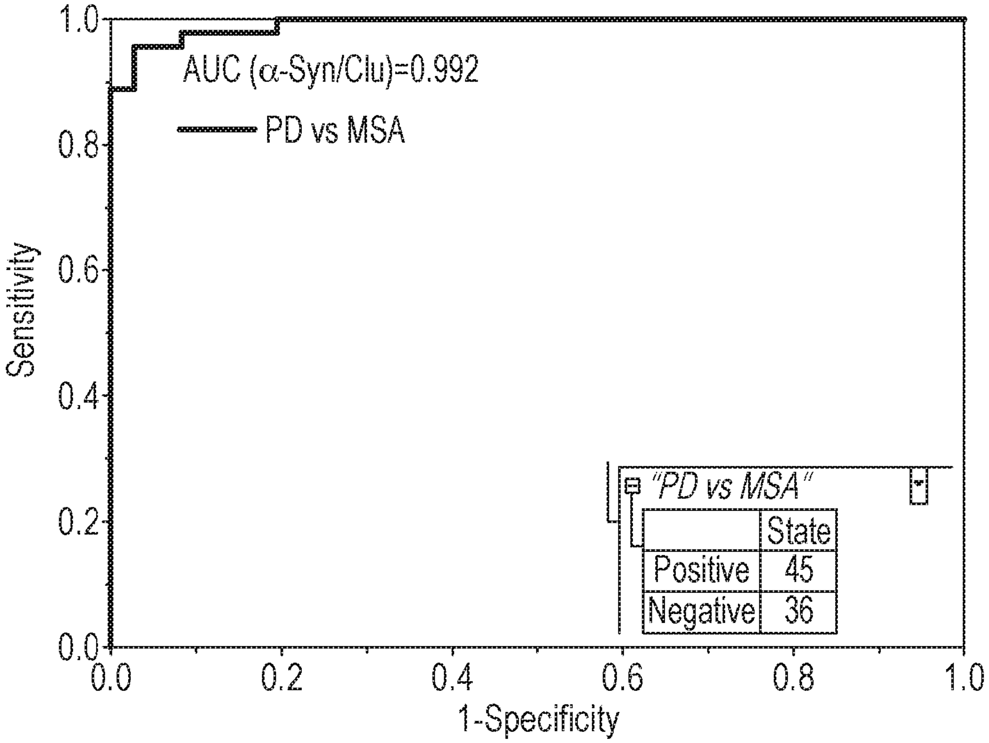
Figure 25D:
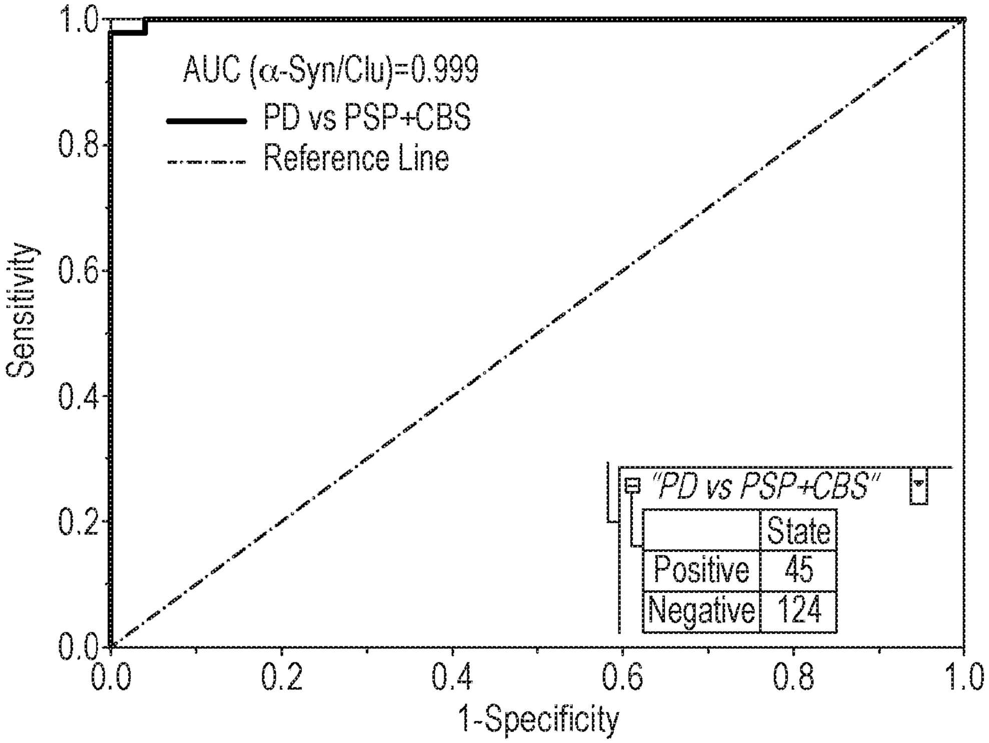

FIG. 24 shows a box plot of α-Synuclein/Clusterin level across different disease groups and healthy control group. $^{}P<0.01$, $^{*}P<0.001$, $^{****}P<0.0001$. Mean values with IQR of exosomal markers and whisker range using SD with coefficient of 1 were used in the boxplots.

FIG. 25 shows ROC curves which represent the diagnostic mode using α-Syn/Clu as feature for the separation of (A) RBD vs MSA, (B) RBD vs PSP+CBS, (C) PD vs MSA, (D) PD vs PSP+CBS.

DETAILED DESCRIPTION OF THE INVENTION

Biomarkers of the Invention

α-Synuclein

The methods of the invention can involve detecting and determining the protein level of α-synuclein in the neuron-derived exosomes from a blood sample. α-Synuclein is well described in the art (e.g. see 5), and is also known as SNCA, NACP, PARK1, PARK4, PD1, or synuclein alpha. The specific protein sequence of α-synuclein is not limiting on the invention. The invention includes detecting and measuring the levels of polymorphic variants of these proteins, or modified versions of these proteins, e.g. post-translational modified versions such as phosphorylated α-synuclein at serine 129.

α-Synuclein in the neuron-derived exosomes in the blood can be used as a predictive and/or a diagnostic biomarker for PD. The α-synuclein content in the neuron-derived exosomes in the blood provides a strong distinction between PD (from early to late phases of the disease progression) and non-PD subjects, such as healthy subjects and subjects having conditions characterised by non-α-synuclein proteinopathy. In particular, the inventors found that the α-synuclein content in the neuron-derived exosomes in the blood of PD subjects (from early to late phases) was significantly increased compared to non-PD subjects. The mean α-synuclein content in the neuron-derived exosomes in the blood of non-PD subjects is between about 12-13 pg/ml. For example, in the Examples below, the mean α-synuclein content in the neuron-derived exosomes in the blood samples of non-PD subjects was measured to be 12.91±5.93 pg/mL (+/−SD).

Therefore, a method for analysing a subject sample may function as a method for identifying if a subject is susceptible to PD or not, i.e. predicting whether the subject will have PD or not. A method for analysing a subject sample may function as a method for diagnosing if a subject has PD or not. A method for analysing a subject sample may also function as a method for discriminating a condition characterised by α-synuclein (such as PD and related conditions (e.g. PD with dementia and MSA)) from a condition characterised by PD from a neurodegenerative disease with non-α-synuclein proteinopathy. A method for analysing a subject sample may also function as a method for discriminating PD from its related conditions, e.g. conditions having similar signs and symptoms, such as atypical parkinsonian syndromes including MSA.

Clusterin

The methods of the invention can involve detecting and determining the protein level of clusterin in the neuron-derived exosomes from a blood sample. Clusterin is well known in the art (e.g. see 17) and is also known as CLU, AAG4, APO-J, APOJ, CLI, CLU1, CLU2, KUB1, NA1/NA2, SGP-2, SGP2, SP-40, or TRPM2. The specific protein sequence of clusterin is not limiting on the invention. The invention includes detecting and measuring the levels of polymorphic variants of these proteins, or modified versions of these proteins, e.g. post-translational modified versions.

Clusterin in the neuron-derived exosomes in the blood can also be used as a predictive and/or a diagnostic biomarker for PD. Clusterin content in neuron-derived exosome in the blood was found to remain at a similar level to healthy subjects throughout the disease progression of PD. The mean clusterin content in the neuron-derived exosomes in the blood of healthy subjects is between about 8-9 ng/ml. For example, in the Examples below, the mean clusterin content in the neuron-derived exosomes in the blood samples of healthy subjects was measured to be 8.67±4.92 ng/mL (+/−SD).

Therefore, a method for analysing a subject sample may function as a method for identifying if a subject is susceptible to PD or not, i.e. predicting whether the subject will have PD or not. A method for analysing a subject sample may function as a method for diagnosing if a subject has PD or not. A method for analysing a subject sample may also function as a method for discriminating a condition characterised by α-synuclein (such as PD and related conditions (e.g. PD with dementia and MSA)) from a condition characterised by PD from a neurodegenerative disease with non-α-synuclein proteinopathy. A method for analysing a subject sample may also function as a method for discriminating PD from its related conditions, e.g. conditions having similar signs and symptoms, such as atypical parkinsonian syndromes including MSA.

Clusterin in the neuron-derived exosomes in the blood can be used as a predictive and/or a diagnostic biomarker for tauopathy. Clusterin provides a strong distinction between tauopathy and non-tauopathy subjects, such as healthy subjects and subjects having conditions characterised by α-synucleinopathy. In particular, the inventors found that the clusterin content in the neuron-derived exosomes in the blood of tauopathy subjects was significantly increased compared to non-tauopathy subjects. The mean clusterin content in the neuron-derived exosomes in the blood of non-tauopathy subjects, such as α-synucleinopathy subjects, is between about 9-10 ng/ml. For example, the Examples below show that the mean clusterin content in the neuron-derived exosomes in the blood sample of PD subjects was measured to be between 9.72±6.02 ng/mL.

Therefore, a method for analysing a subject sample may function as a method for identifying if a subject is susceptible to tauopathy or not, i.e. predicting whether the subject will have tauopathy or not, and/or diagnosing if a subject has tauopathy or not.

Combination of α-Synuclein and Clusterin

To increase the overall confidence that an assay is giving sensitive and specific results across a population, it is advantageous to analyse the levels of both α-synuclein and clusterin. Hence, the methods of the invention can involve detecting and determining the protein levels of α-synuclein and clusterin in the neuron-derived exosomes from a blood sample. The levels of the biomarkers may provide a diagnostic indicator of whether a subject susceptible to PD or not, and/or whether a subject has PD or not.

The inventors found that the α-synuclein content in the neuron-derived exosomes in the blood of PD subjects (from early to late phases) was significantly increased compared to non-PD subjects. The mean α-synuclein content in the neuron-derived exosomes in the blood of non-PD subjects is between about 10-20 pg/ml. On the other hand, clusterin content in neuron-derived exosome in the blood was found to remain at a similar level to healthy subjects throughout the disease progression of PD and to significantly increase in subjects having a neurodegenerative disease with non-α-synuclein proteinopathy compared to healthy or subjects having α-synucleinopathy (e.g. early to late phases of PD). The mean clusterin content in the neuron-derived exosomes in the blood of healthy or subjects having α-synucleinopathy is between about 7-17 ng/ml. The divergent behaviour of the two biomarkers can enhance diagnosis of PD when they are assessed in the same sample. This combination of biomarkers is most useful for enhancing the distinction seen between PD and non-α-synuclein proteinopathy samples.

Therefore, a method for analysing a subject sample may function as a method for identifying if a subject is susceptible to PD or not, i.e. predicting whether the subject will have PD or not. A method for analysing a subject sample may function as a method for diagnosing if a subject has PD or not. Furthermore, a method for analysing a subject sample may function as a method for discriminating a condition characterised by α-synuclein (such as PD and related conditions (e.g. PD with dementia and MSA)) from a condition characterised by non-α-synuclein proteinopathy. A method for analysing a subject sample may also function as a method for discriminating PD from its related conditions, e.g. conditions having similar signs and symptoms, such as MSA.

The Sample

The invention analyses blood samples from subjects. In some embodiments, a method of the invention involves an initial step of obtaining the blood sample from the subject. In other embodiments, however, the blood sample is obtained separately from and prior to performing a method of the invention. After a blood sample has been obtained then methods of the invention could be performed in vitro.

Detection of biomarkers may be performed directly on a sample taken from a subject, or the sample may be treated between being taken from a subject and being analysed. For example, a blood sample may be treated by adding anticoagulants (e.g. EDTA), followed by removing cells and cellular debris, leaving plasma containing exosomes for analysis. Alternatively, a blood sample may be allowed to coagulate, followed by removing cells and various clotting factors, leaving serum containing exosomes for analysis. For example, in the Examples below, the level of the biomarkers were determined in serum samples. Once the plasma or serum is prepared, the sample may be aliquoted and frozen prior to biomarker detection.

In certain aspects of the invention, the subject has one or more signs or symptoms of parkinsonism and who has not been diagnosed with PD. The invention may further comprise a step of identifying a subject having one or more signs or symptoms of parkinsonism and who has not been diagnosed with PD. The clinical criteria for diagnosing PD are well described in the art, e.g. the UK Parkinson's Disease Society Brain Bank (UKPDSBB) criteria (18), the Gelb criteria (19) or the Movement Disorder Society (MDS) PD criteria (20). A subject is not diagnosed with PD unless it meets the requirements set out in any of these clinical PD criteria.

Parkinsonism encompasses several conditions, including PD and other conditions with similar symptoms such as tremor, bradykinesia, rigidity and postural instability, such as primary progressive aphasia (FTD), progressive supranuclear palsy (PSP), corticobasal syndrome (CBS), drug-induced parkinsonism, multiple system atrophy (MSA), and/or vascular parkinsonism. Signs and symptoms of parkinsonism are well described in the art, for example, see reference (21). For example, the signs and symptoms may comprise one or more of the non-motor signs, such as altered handwriting, turning in bed, disrupted walking, disrupted salivation, disrupted speech, reduced facial expression, rigidity, balance impairments, resting tremor, bradykinesia (slow movement), and/or postural instability. The signs and symptoms may comprise one or more of the non-motor signs, such as diagnosis of rapid eye movement sleep behaviour disorder (RBD), olfactory dysfunction, constipation, excessive daytime somnolence, symptomatic hypotension, erectile dysfunction, urinary dysfunction, and/or diagnosis of depression. The signs and symptoms may comprise an abnormal tracer uptake of the presynaptic dopaminergic system.

The subject may be at early phases of PD, but is asymptomatic, e.g. at the pre-clinical stage of PD. The subject may be in the prodromal stage of PD, e.g. the subject may be pre-symptomatic for PD or may already be displaying clinical symptoms. The signs and symptoms of the early phases of PD are known in the art, e.g. as described in reference 1.

For subjects already displaying some clinical PD symptoms, the invention may be used to confirm or resolve another diagnosis. For example, the subject may be suspected to have other forms of degenerative parkinsonisms or other conditions that affect movement. For example, the subject may be suspected of having primary progressive aphasia (FTD), progressive supranuclear palsy (PSP), corticobasal syndrome (CBS), drug-induced parkinsonism, multiple system atrophy (MSA), vascular parkinsonism, and/or benign essential tremor. Symptoms of these disorders are known in the art (e.g. see 21).

The invention is particularly useful for discriminating a condition characterised by α-synuclein (such as PD and related conditions (e.g. PD with dementia and MSA)) from a condition characterised by non-α-synuclein proteinopathy. Thus, the subject may be suspected of having PD, FTD, PSP, or CBS.

The invention is particularly useful for discriminating PD from its related conditions, e.g. conditions having similar signs and symptoms, such as atypical parkinsonian syndromes including MSA.

The subject may have already begun treatment. For example, the subject may have begun α-synuclein-targeting therapy, such as immunotherapy (e.g. anti-α-synuclein antibody therapy), phenylbutyrate-triglyceride (PBT), NPT 200-11, Nilotinib Ambroxol, and ENT-01, which are currently undergoing clinical trials targeting α-synuclein that aim to protect brain cells and slow down PD.

In certain aspects of the invention, it is the intention that the invention can be implemented relatively easily and/or cheaply in that the invention is not restricted to being used in subjects who are already suspected of having PD. Rather, it can be used to screen the general population or a high risk population e.g. subjects at least 50 years old (e.g. ≥50, ≥55, ≥60, ≥65, ≥70). Subjects who are at least 50 years old are prone to developing PD.

The subject may already be known to be predisposed to the development of PD e.g. due to family or genetic links. For example, the subject may contain mutations in the following genes: α-synuclein (Park1), parkin (Park2), DJ-1 (Park7), UCHL1 (Park5), A.53T, A30P, and/or E46K. In other embodiments, the subject may have no such predisposition, and may develop the disease as a result of environmental factors e.g. as a result of exposure to particular chemicals (such as toxins or pharmaceuticals), as a result of diet, as a result of infection, etc.

The subject may be identified by a questionnaire enquiring relevant prodromal PD signs and symptoms (e.g. sleep disturbance, anosmia, anxiety, apathy) followed by a blood test for gene mutations that are associated with PD.

The subject will typically be a human being. In some embodiments, however, the invention is useful in non-human organisms e.g. mouse, rat, rabbit, guinea pig, cat, dog, horse, pig, cow, or non-human primate (monkeys or apes, such as macaques or chimpanzees). In non-human embodiments, any method used for detection of proteins by the invention will typically be based on the relevant non-human ortholog of the human protein disclosed herein. In some embodiments animals can be used experimentally to monitor the impact of a therapeutic on a particular biomarker.

Exosomes

The invention analyses the biomarkers content in the exosomes from the blood samples from subjects. Exosomes are double-membrane vesicles (40-120 nm) released by most cell types including neurons (22). Circulating exosome composition and function are altered in subjects having PD, especially the exosomes that are released from the CNS tissues (e.g. the neuron-derived exosomes) (12). The inventors surprising found that circulating exosome composition is also altered in subjects susceptible to PD. Thus, the protein content in the exosomes in a blood sample can be used to as biomarkers for PD, from early to late phases of PD.

In some embodiments, a method of the invention further involves a step of isolating exosomes from the blood sample from the subject. In other embodiments, however, the exosomes are isolated separately from and prior to performing a method of the invention.

Exosomes can be isolated from the blood sample using multiple methods including ultracentrifugation, immunomagnetic beads, and/or chromatography. Additionally, exosomes have a lipid bilayer; therefore RNAse treatment prior to use will ensure that cargo used downstream was encapsulated within the vesicle. The exosomes may be identified using western blots or mass spectrometry using proteins which are involved in biogenesis of intraluminal vesicles, including tetraspanins (e.g. CD9, CD63, and/or CD81) and/or proteins involved in the endosomal sorting complex required for transport (ESCRT) machinery needed for biogenesis (e.g. PDCD6IP, TSG101, VPS28, VPS37, VPS25, VPS36, SNF8, and/or CHMP).

The invention refers to determining the level(s) of biomarker(s) in a selected population of exosomes in a blood sample. The selected population of exosomes may be exosomes that are released from the CNS tissues, such as neurons. The selected population of exosomes that are released from neurons is referred to as neuron-derived exosomes herein. Thus, the selected population of exosomes may contain neuronal proteins. For example, exosomes released from developing and mature hippocampal neurons contain L1 cell adhesion molecule (L1CAM) and the GluR2/3 subunits of glutamate receptors, both of which are known neuronal markers (23,24). Hence, the selected population of exosomes may contain L1CAM. The selected population of exosomes may contain the GluR2/3 subunits of glutamate receptors.

Ligands having affinity for the neuronal markers may be used to capture the neuron-derived exosomes. The affinity ligand may be any molecule that will bind the target without also binding other molecules in the sample. Any type of ligands can be used with the invention. The ligand may be an antibody which can be designed to target the neuronal marker through their antigen binding sites, an organic compound that is able to dock into binding sites on the neuronal marker, an inorganic metal that form coordination complexes with certain amino acids in the target neuronal marker, a hydrophobic molecule that can bind nonpolar pockets in the neuronal marker, and/or a protein with specific binding regions that are able to interact with the neuronal marker. For example, the ligand may be an anti-L1CAM antibody (e.g. clone UJ127 from Abcam, Cambridge, MA, USA).

The selected population of exosomes isolated from a blood sample using a method according to the invention may have a purity of ≥70% (i.e. 70% or greater), ≥80%, ≥90%, ≥95%, ≥97%, ≥99% or 100%.

Coated Particles

The affinity ligands described above may be immobilised on coated particles to capture the selected population of the exosomes.

The invention also provides a coated particle having a coating comprising a zwitterionic polymer coupled to a ligand having affinity for the selected population of exosomes. The coated particles can be prepared by growing a zwitterionic polymer from the surface of a particle using surface initiated reversible addition fragmentation chain transfer (RAFT) polymerisation. The coated particles are particularly useful for isolating neuron-derived exosomes for use in the methods of the invention.

Hence, the invention also provides a method of isolating exosomes from a sample, comprising steps of: contacting the sample with the coated particle of the invention; removing unbound sample; and separating the captured exosomes.

Also described herein is a method of producing coated particles which comprises the steps of:

(a) growing a zwitterionic polymer on the surface of a particle using reversible addition fragmentation chain transfer (RAFT) to provide a particle having a coating comprising a zwitterionic polymer;
(b) optionally activating the zwitterionic polymer to provide active functional groups on the zwitterionic polymer; and
(c) conjugating a ligand having affinity for the selected population of exosomes to the zwitterionic polymer.

The coated particle may comprise a particle of metal, magnetic material, paramagnetic material, glass or epoxy. In general, any immunoassay bead may be used as the particle. Magnetic or paramagnetic particles are preferred. Magnetic beads may, for example, comprise iron oxide particles, e.g. $Fe_3O_4$. The iron oxide particles may be encapsulated within a polymeric matrix, for example. Particles preferred for use in the present invention are those described by references 26 and 27.

The particles are typically from approximately 30 nm to 5 μm in size, more preferably from 50 to 3000 nm, for example from 1000 to 3000 nm. The particles may be nanoparticles of 30 nm to 1000 nm in size, preferably from 50 nm to 800 nm or from 100 nm to 500 nm.

The zwitterionic polymer may comprise carboxybetaine, sulfobetaine and/or phosphoryl choline moieties, preferably carboxybetaine and/or sulfobetaine moieties, most preferably carboxybetaine moieties. Typically, the zwitterionic polymer comprises repeating units of a zwitterionic monomer. Preferably the zwitterionic monomer comprises carboxybetaine and/or sulfobetaine, most preferably carboxybetaine. The monomer units may be acrylates, methacrylates, acrylamides or methacrylamides, for example. Acrylates and methacrylates are preferred due to the functional reactivity of the carboxylic acid groups.

The polymer may be poly(carboxybetaine methacrylate) (pCMBA). pCBMA is a highly effective antifouling polymer which also has the benefit of convenient functionalisation to enable attachment of the desired antibodies.

The polymer may be a brush polymer, where a plurality of polymer chains radiate out from the central particle. Particles having brush polymers attached demonstrate particularly effective antifouling due to their high conformational entropy and ability to repel non-specific biological materials.

Preferred particles have a high level of polymer coating on their surface. Preferably, at least 20% of the particle surface is coated with polymer, more preferably at least 50%, most preferably at least 80%, 90% or 95% of the surface is coated with polymer. In a preferred embodiment, at least 98% or at least 99% of the surface of the particle is coated with polymer. The degree of coating can be determined using visual techniques such as SEM.

The polymer coating typically has a thickness of at least 10 nm, preferably at least 100 nm, for example a thickness of from 10 nm to 500 nm, preferably from 100 to 300 nm, e.g. 100 nm to 200 nm. The coating thickness can be determined by comparing the size of the uncoated particle with that of the particle having the zwitterionic polymer attached, for example using visual techniques such as SEM.

The antibody may be covalently attached to functional groups on the zwitterionic polymer, for example where the polymer is pCBMA, the antibody may be attached to carboxyl groups of the pCBMA.

The ligand may have affinity for neuron-derived exosomes, for example, the ligand is an anti-L1CAM antibody.

The coated particles are typically produced by growing polymer from the surface of the particle. Intermediate layers may be present between the particle and the zwitterionic coating, or the zwitterionic coating may be directly attached to the particle. Growing the polymer from the particle surface (as opposed to grafting a formed polymer onto the particle) enables a high degree of dense polymer coverage of the surface to be achieved, which has consistent coverage and avoids large areas which lack any polymeric coating.

A preferred technique for providing the polymeric coating is reversible addition fragmentation chain transfer (RAFT). Whilst polymerisation techniques for growing polymers on planar surfaces are known in the art, it can be difficult to grow such polymers from the surface of a sub 5 μm particle. The present inventors found that the RAFT process is advantageous over other processes previously used (e.g. atom transfer radical polymerisation, i.e. ATRP), and that this leads to generation of a polymer-coated particle having (i) good colloidal stability; (ii) good density and structure of polymer films; and (iii) good non-fouling character.

The RAFT technique is typically a surface initiated RAFT polymerisation and can be carried out as described in reference 28. 4,4'-azobis(4-cyanovaleric acid (ACVA) can be used as initiator. Typical examples of polymerisation using the RAFT technique to prepare coated particles are set out in FIG. 12. The first step in a RAFT polymerisation is the attachment of a chain transfer agent (CTA) to the surface on which polymerisation is to occur. Suitable materials include 4-cyano-4-(((decylthio)carbonothioyl)thio)pentanoic acid, bis(carboxymethyl)trithiocarbonate (BCMTTC) and 4-cyano-4-(phenylcarbonothioyl)thio)pentanoic acid (CPCTTP). In applying a RAFT polymerisation to the surface of a small particle, selection of the correct chain transfer agent (CTA) is important and the present inventors found that use of bis(carboxymethyl)trithiocarbonate (BCMTTC) provided the most beneficial polymer films, as assessed by spectroscopic signature of the polymer film, colloidal stability of the coated particle, and reduction in nonspecific adsorption.

The polymerisation is typically carried out for sufficient period of time to enable a coating thickness of at least 10 nm or at least 100 nm, preferably a thickness of 10 nm to 500 nm, more preferably from 100 nm to 300 nm, to develop.

Antibody may be conjugated to the zwitterionic polymer coating by providing activated functional groups on the polymer surface, and reacting with antibody. Suitable activated functional groups include, for example, N-hydroxy succinimide (NHS) which is reactive with free amine groups on the antibody. For instance, carboxylic acid groups of a pCBMA coating may be activated by reacting with 1-ethyl-3-(3-dimethylaminopropyl) carbodiimide/N-hydroxysuccinimide (EDC/NHS). Typically, a single antibody, specific for the desired exosomes is attached to the particle. Anti-L1CAM is a preferred antibody. In some aspects, one or more additional molecules may also be attached to the coating.

The coated particles are highly selective for the desired biologic molecules and have very low levels of nonspecific adsorption. The degree of nonspecific adsorption can be measured by comparing particles (a) without zwitterionic polymer and (b) with zwitterionic polymer. Typically, the degree of nonspecific adsorption to the particles of the invention is less than 50% of that of an equivalent particle lacking zwitterionic polymer. Preferably, the degree of nonspecific adsorption is less than 20%, more preferably less than 15%, less than 10%, less than 5%, less than 2% or less than 1% of that of an equivalent particle lacking zwitterionic polymer.

Nonspecific adsorption can be determined, for example, by measuring adsorption of a selected nonspecific particle, e.g. bovine serum albumin (BSA), to particles conjugated to anti-HA antibody. The degree of nonspecific adsorption can be measured spectroscopically through levels of solution depletion or microscopically (e.g. SEM or particle nonspecific accumulation at protein surfaces as imaged optically).

Isolation of exosomes may be achieved by contacting a sample, e.g. a blood sample, with the coated particles described herein. After incubation of the coated particles with the sample, particle-exosome complexes are isolated by standard techniques. IN a preferred aspect, magnetic or paramagnetic particles are used and the particle-exosome complexes are separated by magnetic separation.

Biomarker Detection

Techniques for detecting proteins are well known in the art, e.g. affinity ligand-dependent methods (such as enzyme-linked immunosorbent assay (ELISA), protein immunoprecipitation, immunoelectrophoresis, Western blot, or protein immunostaining), and/or spectrometry methods (such as high-performance liquid chromatography (HPLC), or liquid chromatography-mass spectrometry (LC/MS)).

Detection of a biomarker of the invention typically involves contacting the sample with an affinity ligand, wherein a specific (rather than non-specific) binding reaction between the sample and the affinity ligand indicates the presence of the biomarker of interest.

The affinity ligand may be any molecule that will bind the target without also binding other molecules in the sample. Any type of ligands can be used with the invention. The ligand may be an antibody which can be designed to target α-synuclein or clusterin through their antigen binding sites, an organic compound that is able to dock into binding sites on α-synuclein or clusterin, an inorganic metal that form coordination complexes with certain amino acids in α-synuclein or clusterin, a hydrophobic molecule that can bind nonpolar pockets in α-synuclein or clusterin, and/or a protein with specific binding regions that are able to interact with α-synuclein or clusterin.

For example, the affinity ligand for α-synuclein may be an anti-α-synuclein antibody, e.g. from MSD (see Examples).

For example, the affinity ligand for clusterin may be an anti-clusterin antibody, e.g. from MSD (see Examples).

The affinity ligand may be immobilised on a solid support (e.g. a bead, plate, filter, film, slide, microarray support, resin, etc.).

In embodiments where both biomarkers (i.e. α-synuclein and clusterin) are to be detected, the sample may be simultaneously contacted with both ligands having affinity to the biomarkers ("multiplexed") in a single reaction compartment, e.g. a microtitre well, microfluidic chamber or detection pore. Alternatively, these biomarkers may either be contacted with its affinity ligand in separate, individual reaction compartments, and/or experiments could be separated over time and using different platform technologies in either multiplexed single reaction compartments or separate, individual reaction compartments. Multiplex platforms for the detection of proteins by immunoassay are well known in the art, e.g. MSD® Multi-array assay system.

Methods and apparatus for detecting binding reactions in immunoassays are standard in the art. For example, fluorescence-based detection methods and/or electrochemiluminescence detection methods may be used with the invention. For example, a sandwich immunoassay may be used to detect a biomarker, and the assay typically involves binding the biomarker to an immobilised affinity ligand on a glass substrate, followed by binding a second affinity ligand which is fluorescently labelled or electrochemiluminscent labelled to the biomarker, and then detecting the fluorescence or electrochemiluminscence.

The data obtained from detecting the biomarkers can be combined in a multivariate analysis. The combination of biomarkers may increase the classification power relative to a single biomarker. The combination of biomarkers can be evaluated simultaneously or in series. For evaluation in series, the data obtained for each biomarker can be combined after analysing the biomarker, e.g. after determining the level of the biomarker. Thus, for instance, a sample could be split into sub-samples and the sub-samples could be assayed in series.

Data Interpretation and Manipulation

The invention involves a step of determining the level(s) of the biomarker(s) of the invention. The invention may require a quantitative or semi-quantitative determination of each of the biomarkers. The invention may involve a relative determination (e.g. a ratio relative to another marker, or a measurement relative to the same marker in a control sample). The invention may involve a threshold determination (e.g. a yes/no determination whether a level is above or below a threshold).

The level(s) of the biomarker(s) of the invention are altered in a disease cohort, compared with the control cohort. An analysis of the level of these biomarkers in the case and control populations may identify differences which provide diagnostic information. A skilled person can easily determine the relative change (e.g. up-regulation or down-regulation) for any given biomarker relative to any particular control of interest (e.g. a negative control or a positive control) in any given blood sample.

A control sample can be a positive control sample or a negative control sample. Typically the control sample is age-matched against the test subject. A positive control sample includes samples from confirmed cases of PD. A negative control sample includes samples from confirmed cases of the absence of PD. A non-PD sample can be a subject with presentation of other unrelated neurodegenerative conditions, e.g. Frontotemporal dementia (FTD), progressive supranuclear palsy (PSP), corticobasal syndrome (CBS). The absolute levels of a biomarker in a particular control sample (e.g. samples of a non-PD subject who has FTD) may be different from that in another control sample (e.g. samples of a non-PD subject who has PSP). It will be appreciated the relative expression profiles (e.g. up- or down-regulation or fold-changes) in PD samples compared to non-PD samples (i.e. a negative control sample) observed for the biomarkers of the invention might be relevant to only the specific control indicated.

Usually biomarkers will be measured to provide quantitative or semi-quantitative results (whether as relative concentration, absolute concentration, fold-change, etc.) as this gives more data for use with classifier algorithms. Usually the raw data obtained from an assay for determining the presence, absence, or level (absolute or relative) requires some manipulation prior to their use. For instance, the nature of most detection techniques means that some signal will sometimes be seen even if no biomarker is actually present and so this noise may be removed before the results are interpreted. Similarly, there may be a background level of the biomarker in the general population which needs to be compensated for. Data may need scaling or standardising to facilitate inter-experiments comparisons. These and similar issues, and techniques for dealing with them, are well known in the art.

Various techniques are available to compensate for background signal in a particular experiment. For example, replicate measurements will usually be performed (e.g. using duplicate or triplicate reactions) to determine intra-assay variation and average values from the replicates can be compared (e.g. the median value of the immunoassay). Furthermore, standard markers can be used to determine inter-assay variation and to permit calibration and/or normalisation e.g. an immunoassay reaction can include one or more 'standards', of known concentration, to determine the amplification efficiency of the immunoassay reaction, and to permit estimation of the total protein content of an unknown sample, relative to other unknown samples.

As well as compensating for variation which is inherent between different experiments, it can also be important to compensate for background levels of a biomarker which are present in the general population. Again, suitable techniques are well known. For example, levels of a particular biomarker in a sample will usually be measured quantitatively or semi-quantitatively to permit comparison to the background level of that biomarker. Various controls can be used to provide a suitable baseline for comparison, and choosing suitable controls is routine in the diagnostic field.

The measured level(s) of the biomarker(s), after any compensation or normalisation can be transformed into a diagnostic result respectively in various ways. This transformation may involve an algorithm which provides a diagnostic result as a function of the measured level(s).

The creation of algorithms for converting measured levels or raw data into scores or results is well known in the art. For example, linear or non-linear classifier algorithms can be used. These algorithms can be trained using data from any particular technique for measuring the marker(s). Suitable training data will have been obtained by measuring the biomarkers in "case" and "control" samples i.e. samples from subjects known to suffer from PD and from subjects known not to suffer from PD. Most usefully the control samples will also include samples from subjects with an unrelated neurodegenerative condition, such as FTD, PSP or CBS, which is to be distinguished from PD, e.g. it is useful to train the algorithm with data from subjects with prodromal and/or with data from subjects with unrelated neurodegenerative conditions. The classifier algorithm is modified until it can distinguish between the case and control samples e.g. by changing the optimal cut-off value, etc. For example, as shown in Example 2 and FIG. 3, the optimal cut-off value for using α-synuclein to distinguish clinical PD and health control samples was found to be 14.21 pg/ml.

Thus a method of the invention may include a step of analysing biomarker levels in a subject's sample by using a classifier algorithm which distinguishes between PD subjects and non-PD subjects based on measured biomarker levels in samples taken from such subjects. Various suitable classifier algorithms are available e.g. linear discriminant analysis, naive Bayes classifiers, regression modelling, perceptrons, support vector machines (SVM) and genetic programming (GP), as well as a series of statistical methods such as Principal Component Analysis (PCA) and unsupervised hierarchical clustering and linear modelling.

Moreover, these approaches can potentially distinguish PD subjects from subjects with unrelated neurodegenerative conditions. The biomarkers of the invention can be used to train such algorithms to reliably make such distinctions. The resulting data will be analysed for any potential signatures relating to differences between patient cohorts referring to levels of statistical significance (generally $p<0.05$), multiple testing correction and fold changes within the expression data that could be indicative of biological effect (normally it is desirable to use techniques that can indicate a change of at least 1.5 fold e.g. >1.75 fold, >2-fold, >2.5-fold, >5-fold, etc.). The classification performance (sensitivity and specificity (S+S), Receiver Operating Characteristic (ROC) analysis) of any putative biomarkers will be rigorously assessed using nested cross validation and permutation analyses prior to further validation.

Diagnosis

A method of the invention may include a step of comparing biomarker levels in a subject's sample to a reference. The reference may be (i) a threshold value, (ii) the corresponding biomarker level in a sample from a positive control, and/or (iii) the corresponding biomarker level in a sample from a negative control. The comparison provides a diagnostic indicator of whether the subject is susceptible to the disease or has the disease. As would be within the understanding of a person skilled in the art, whether the level or a biomarker is increased or decreased would depend on the reference used. For example, in a subject having PD, the α-synuclein content in the neuron-derived exosomes in the blood would be at a higher level than the level in a negative control sample (non-PD sample), and at a similar level as in a positive control sample (PD sample).

Typically, the invention involves comparing the level of a biomarker against a threshold value, and the optimal threshold value may be determined by training classifier algorithm to distinguish between "case" and "control" samples as explained above.

For example, the reference for α-synuclein may be a threshold value of between 10-20 pg/ml, such as between 12-16 pg/ml or between 14-15 pg/ml. If a blood sample contains a higher α-synuclein level in the neuron-derived exosomes relative to the threshold value, this indicates that the subject is susceptible to or has PD. Conversely, if a blood sample contains a α-synuclein level in the neuron-derived exosomes similar to the threshold value, this indicates that the subject is not susceptible to or does not have PD.

In some embodiments, if a blood sample contains a higher α-synuclein level in the neuron-derived exosomes relative to the threshold value indicates that the subject has a condition characterised by α-synuclein (such as PD and related conditions (e.g. PD with dementia and MSA)) and not a condition characterised by non-α-synuclein proteinopathy.

In some embodiments, if a blood sample contains a higher α-synuclein level in the neuron-derived exosomes relative to the threshold value indicates that the subject has PD and not its related conditions, e.g. conditions having similar signs and symptoms, such as atypical parkinsonian syndromes including MSA.

The reference for clusterin may be a threshold value of between 7-17 pg/ml, such as between 10-14 ng/ml or between 12-13 ng/ml. If a blood sample contains: (i) a higher α-synuclein level in the neuron-derived exosomes relative to the threshold value for α-synuclein, and (ii) has a clusterin level that is not higher than the threshold value, this indicates that the subject is susceptible to or has PD.

In some embodiments, if a blood sample contains: (i) a higher α-synuclein level in the neuron-derived exosomes relative to the threshold value for α-synuclein, and (ii) has a clusterin level that is not higher than the threshold value, this indicates that the subject has a condition characterised by α-synuclein (such as PD and related conditions (e.g. PD with dementia and MSA)) and not a condition characterised by non-α-synuclein proteinopathy.

In some embodiments, if a blood sample contains: (i) a higher α-synuclein level in the neuron-derived exosomes relative to the threshold value for α-synuclein, and (ii) has a clusterin level that is not higher than the threshold value, this indicates that the subject has PD and not its related conditions, e.g. conditions having similar signs and symptoms, such as atypical parkinsonian syndromes including MSA.

Alternatively, if a subject contains a higher clusterin level in the neuron-derived exosomes in the blood relative to the threshold value, this indicates that the subject is susceptible to or has tauopathy.

When referring to the diagnosis of a subject being susceptible to PD, this means predicting whether the subject will have clinical PD or not. Hence, the diagnosis may indicate whether the subject is in the early phases of PD, such as pre-clinical PD or prodromal PD. Preclinical PD is the disease phase during which neurodegeneration has started but without evident symptoms or signs of the disease. Prodromal PD is the disease phase during which the symptoms and signs of the disease are present, but are yet insufficient to define disease. The MDS criteria for preclinical and prodromal PD are provided in reference 1.

When referring to the diagnosis of tauopathy, the tauopathy may be, for example, frontal temporal dementia (FTD), progressive supranuclear palsy (PSP) and corticobasal syndrome (CBS)).

Advanced statistical tools can be used to determine whether the levels determined for each biomarker in the various samples (case or control) are the same or different. For example, an in vitro diagnosis will rarely be based on comparing a single determination. Rather, an appropriate number of determinations will be made with an appropriate level of accuracy to give a desired statistical certainty with an acceptable sensitivity and/or specificity. Levels of biomarkers are measured quantitatively to permit proper comparison, and enough determinations will be made to ensure that any difference in levels can be assigned a statistical significance to a level of $p<0.05$ or better.

Methods of the invention may have sensitivity of at least, but not limited to, 50% (e.g. ≥50%, ≥55%, ≥60%, ≥65%, ≥70%, ≥75%, ≥80%, ≥85%, ≥90%, ≥95%, ≥96%, ≥97%, ≥98%, ≥99%).

Methods of the invention may have specificity of at least, but not limited to, 50% (e.g. ≥50%, ≥55%, ≥60%, ≥65%, ≥70%, ≥75%, ≥80%, ≥85%, ≥90%, ≥95%, ≥96%, ≥97%, ≥98%, ≥99%).

In particular, the inventors assessed α-synuclein to clusterin ratio and applied a logistic regression model for the combination of these biomarkers. Both analyses showed that combined α-synuclein to clusterin measurements exhibited an improved AUC, sensitivity and specificity estimates for differential diagnosis in predicting clinical PD versus other proteinopathies, with an AUC=0.98 (sensitivity=95%; specificity=93%), even in the prodromal phase of PD, with an AUC=0.98 (sensitivity=94%, specificity=96%). The composite α-synuclein to clusterin measurement also exhibited a high performance in distinguishing prodromal or clinical PD from MSA (AUC=0.94 and 0.91, respectively).

Data obtained from methods of the invention, and/or diagnostic information based on those data, may be stored in a computer medium (e.g. in RAM, in non-volatile computer memory, on CD-ROM, DVD) and/or may be transmitted between computers e.g. over the Internet.

If a method of the invention indicates that a subject has PD, further steps may then follow. For instance, the subject may undergo confirmatory diagnostic procedures, such as those involving physical inspection of the subject, and/or may be treated with therapeutic agent(s) suitable for treating PD. The confirmatory diagnostic procedures include known biomarkers for PD and/or non-α-synuclein proteinopathy, other information about the subject; and/or other diagnostic tests or clinical indicators for PD, such as DaTSCAN for determining dopamine uptake and/or brain imaging scans using MRI-based markers.

The invention also provides a method of preventing and/or treating Parkinson's disease in a subject, comprising identifying a subject susceptible to Parkinson's disease according to the methods of the invention, and treating the subject with a therapy for Parkinson's disease. A therapy for Parkinson's disease may involve administering levodopa, dopamine agonists (e.g. pramipexole, ropinirole) and/or monoamine oxidase-B inhibitors (e.g. selegiline and rasagiline).

Thus, the invention also provides levodopa for use in a method of preventing and/or treating Parkinson's disease in a subject, comprising identifying a subject susceptible to Parkinson's disease according to the methods of the invention, and administering a therapeutically effective amount of levodopa to the subject.

The invention also provides dopamine agonist for use in a method of preventing and/or treating Parkinson's disease in a subject, comprising identifying a subject susceptible to Parkinson's disease according to the methods of the invention, and administering a therapeutically effective amount of dopamine agonist to the subject.

The invention also provides monoamine oxidase-B inhibitor for use in a method of preventing and/or treating Parkinson's disease in a subject, comprising identifying a subject susceptible to Parkinson's disease according to the methods of the invention, and administering a therapeutically effective amount of monoamine oxidase-B inhibitor to the subject.

The invention also provides a method of preventing and/or treating a condition characterised by α-synucleinopathy in a subject, comprising treating the subject with a α-synuclein-targeting therapy and monitoring the efficacy of the disease according to the methods of the invention. A α-synuclein-targeting therapy may involve administering a therapeutic agent targeting α-synuclein such as anti-α-synuclein antibody, phenylbutyrate-triglyceride (PBT), NPT 200-11, Nilotinib, Ambroxol, or ENT-01. Thus, the invention also provides a therapeutic agent targeting α-synuclein for use in a method of preventing and/or treating a condition characterised by α-synucleinopathy in a subject, comprising administering the subject with therapeutically effective amount of a therapeutic agent targeting α-synuclein and monitoring the efficacy of the disease according to the methods of the invention.

Monitoring Efficacy of Therapy

Methods of the invention may involve testing samples from the same subject at two or more different points in time. Methods which determine changes in biomarker(s) over time can be used, for instance, to monitor the efficacy of a therapy being administered to the subject. Thus, the invention also provides a method of monitoring the efficacy of a α-synuclein-targeting therapy being administered to a subject. The invention also provides a method for monitoring development of a condition characterised by α-synucleinopathy, such as PD, in a subject. Each biomarker of the invention may be determined according to the methods of the invention at two or more different points in time, with changing levels of each biomarker over time indicating whether the disease is getting better or worse.

The therapy may be administered before the first sample is taken, at the same time as the first sample is taken, or after the first sample is taken. The invention can be used to monitor a subject who is receiving α-synuclein-targeting therapy, for example, the subject may be receiving a therapeutic agent such as anti-α-synuclein antibody therapy, phenylbutyrate-triglyceride (PBT), NPT 200-11, Nilotinib and Ambroxol, ENT-01, which are currently undergoing clinical trials targeting alpha-synuclein that aim to protect brain cells and slow down Parkinson's.

Thus, the methods of the invention may comprise the steps of: (i) determining the levels of α-synuclein and/or clusterin in a first sample from the subject taken at a first time; and (ii) determining the levels of α-synuclein and/or clusterin in a second sample from the subject taken at a second time, wherein: (a) the second time is later than the first time; and (b) a change in the level(s) of the biomarker(s) in the second sample compared with the first sample indicates that a condition characterised by α-synucleinopathy, such as PD, is in remission or is progressing. Thus, the method monitors the biomarker(s) over time, with changing levels indicating whether the disease is getting better or worse. As would be within the understanding of a person skilled in the art, when the level of the biomarker changes towards the level seen in healthy controls (and away from the level seen in disease patients), the condition characterised by α-synucleinopathy, such as PD, is in remission. On the other hand, when the level of the biomarker changes towards the level seen in disease patients or remain at the level seen in disease patients (and/or away from the level seen in healthy controls), the condition characterised by α-synucleinopathy, such as PD, is progressing.

The disease development can be either an improvement or a worsening, and this method may be used in various ways e.g. to monitor the natural progress of a condition characterised by α-synucleinopathy, such as PD, or to monitor the efficacy of a α-synuclein-targeting therapy being administered to the subject. Thus, a subject may receive a therapeutic agent before the first time, at the first time, or between the first time and the second time.

Where the methods involve a first time and a second time, these times may differ by at least 1 day, 1 week, 1 month or 1 year. Samples may be taken regularly. The methods may involve measuring biomarkers in more than 2 samples taken at more than 2 time points i.e. there may be a 3rd sample, a 4th sample, a 5th sample, etc.

Kit

The invention also provides diagnostic devices and kits for detecting the biomarkers of the invention.

The invention also provides a diagnostic device for use in providing a diagnostic indicator of a subject susceptible to or having Parkinson's disease, wherein the device permits determination of the levels of α-synuclein and/or clusterin in a sample.

The invention also provides a diagnostic device for use in discriminating a condition characterised by α-synuclein (such as PD and related conditions (e.g. PD with dementia and MSA)) from a condition characterised by non-α-synuclein proteinopathy in a subject, wherein the device permits determination of the levels of α-synuclein and/or clusterin.

The invention also provides a diagnostic device for use in discriminating PD from its related conditions (e.g. conditions having similar signs and symptoms, such as atypical parkinsonian syndromes including MSA) in a subject, wherein the device permits determination of the levels of α-synuclein and/or clusterin.

The invention also provides a kit comprising (i) a diagnostic device of the invention and (ii) instructions for using the device to detect α-synuclein and/or clusterin. The kit is useful in providing a diagnostic indicator of a subject susceptible to or having Parkinson's disease. The kit is particularly useful in discriminating a condition characterised by α-synuclein (such as PD and related conditions (e.g. PD with dementia and MSA)) from a condition characterised by non-α-synuclein proteinopathy in a subject. The kit is particularly useful in discriminating PD from its related conditions, e.g. conditions having similar signs and symptoms, such as atypical parkinsonian syndromes including MSA.

The invention also provides a product comprising (i) one or more detection reagents which permit measurement of synuclein and/or clusterin, and (ii) a sample from a subject.

The invention also provides a kit comprising the coated particles of the invention for isolating a selected population of exosomes from a blood sample and/or reagents for determining the levels of α-synuclein and clusterin in the neuron-derived exosomes in a blood sample.

Other

It is to be understood that the terminology used herein is for the purpose of describing particular embodiments of the invention only, and is not intended to be limiting.

In addition as used in this specification and the appended claims, the singular forms "a", "an", and "the" include plural references unless the content clearly dictates otherwise. Thus, for example, reference to "a bacteria strain" includes two or more "bacteria strains".

Furthermore, when referring to "≥x" herein, this means equal to or greater than x.

The term "comprising" encompasses "including" as well as "consisting" e.g. a composition "comprising" X may consist exclusively of X or may include something additional e.g. X+Y.

References to a "level" of a biomarker mean the amount of an analyte (e.g. α-synuclein or clusterin) measured in a sample and this encompasses relative and absolute concentrations of the analyte, analyte titres, relationships to a threshold, rankings, percentiles, etc.

An assay's "sensitivity" is the proportion of true positives which are correctly identified i.e. the proportion of subjects with PD who test positive by a method of the invention. This can apply to individual biomarkers, both biomarkers (α-synuclein and clusterin), single assays or assays which combine data integrated from multiple sources. It can relate to the ability of a method to identify samples containing a specific analyte (e.g. α-synuclein or clusterin) or to the ability of a method to correctly identify samples from subjects susceptible to or having disease.

An assay's "specificity" is the proportion of true negatives which are correctly identified i.e. the proportion of subjects without PD who test negative by a method of the invention. This can apply to individual biomarkers, both biomarkers (α-synuclein and clusterin), single assays or assays which combine data integrated from multiple sources. It can relate to the ability of a method to identify samples containing a specific analyte (e.g. α-synuclein or clusterin) or to the ability of a method to correctly identify samples from subjects susceptible to or having disease.

All publications, patents and patent applications cited herein, whether supra or infra, are hereby incorporated by reference in their entirety.

The following examples illustrate the invention.

EXAMPLES

Example 1

This example aims to develop a method to specifically isolate neuron-specific exosomes.

Synthesis of Carboxybetaine Methacrylate (CBMA)

CBMA was synthesized according to an adapted literature procedure (25). 3.16 g 2 -(Dimethylamino)ethyl methacrylate (DMAEMA; 20 mmol, 1 equiv.; Sigma Aldrich) was dissolved in 50 mL dry dichloromethane (DCM) and cooled to 0-5° C. 1.72 g β-propiolactone (24 mmol, 1.2 equiv.; Alfa Aesar) dissolved in 10 mL dry DCM was then added slowly. The solution was stirred at 0-5° C. for 8 h. The resulting white precipitate was isolated by filtration and washed with DCM and Et2O affording 1.91 g (42%) of pure CBMA. 1H NMR (400 MHz, D2O) δ 6.27-6.11 (m, 1H), 5.78 (p, J=1.4 Hz, 1H), 4.65 (dq, J=7.2, 2.3 Hz, 2H), 3.86-3.74 (m, 2H), 3.74-3.62 (m, 2H), 3.20 (s, 6H), 2.74 (t, J=7.9 Hz, 2H), 1.94 (t, J=1.3 Hz, 3H). Anhydrous DCM was obtained from a MBraun MPSP-800 column and used immediately. NMR spectra were recorded and referenced to the solvent (δ=4.79 ppm).

Preparation of Poly(Carboxybetaine Methacrylate) Based Zwitterionic Magnetic Beads and Antibody Conjugation The magnetic beads were prepared by a two-step approach comprising of the formation of ferrihydrite/formaldehyde composite microbeads and subsequent hydrothermal reduction of the ferrihydrite to $Fe_3O_4$ (26,27). Poly (carboxybetaine methacrylate), was then formed and coated on the $Fe_3O_4$ using reversible addition fragmentation chain transfer (RAFT) method to generate pCBMA magnetic beads (28). Bis(carboxymethyl)trithiocarbonate (Bittc, Sigma) and 4,4'-Azobis(4-cyanovaleric acid) (ACVA) were used as RAFT agent and initiator, respectively. For conjugation of antibody, the carboxylic acid groups of the pCBMA beads were activated with 2-morpholinoethanesulfonic acid (MES) buffer (50 mM, pH 5.5) containing 50 mg/mL 1-ethyl-3-(3-dimethylaminopropyl) carbodiimide/N-hydroxysuccinimide (EDC/NHS, Sigma) at room temperature for 1 h. Beads were then rinsed with MES buffer and PBS, followed by adding 8 μg of anti-L1CAM (ab80832, Abcam, UK) per 1 mg beads. The mixture incubated on the rotator for 1.5 h at room temperature. The resultant pCBMA-anti-L1CAM beads were washed twice with PBS and used for immunocapture.

Figure 6A:
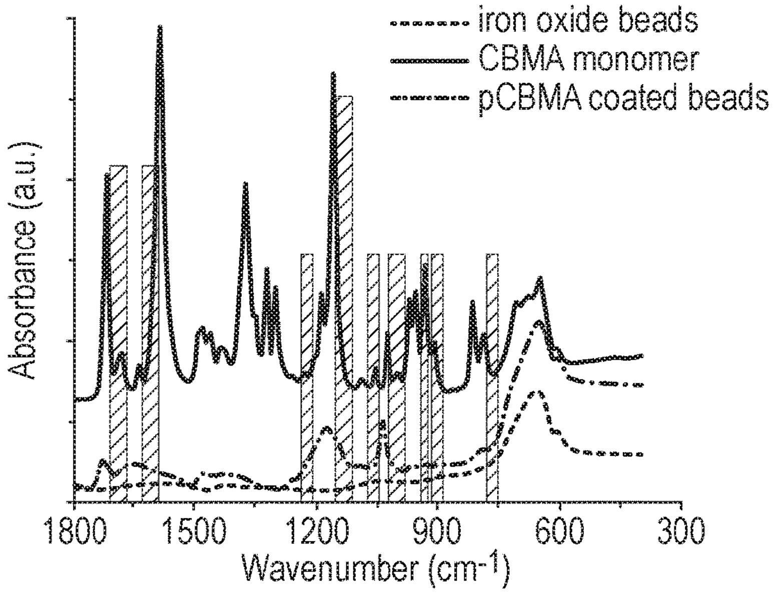
Figure 6B:
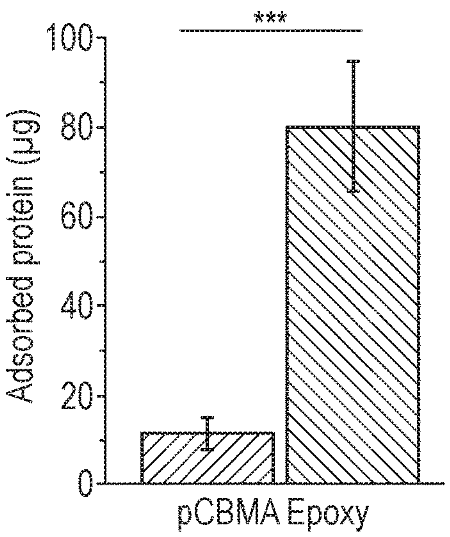
Figure 6C:
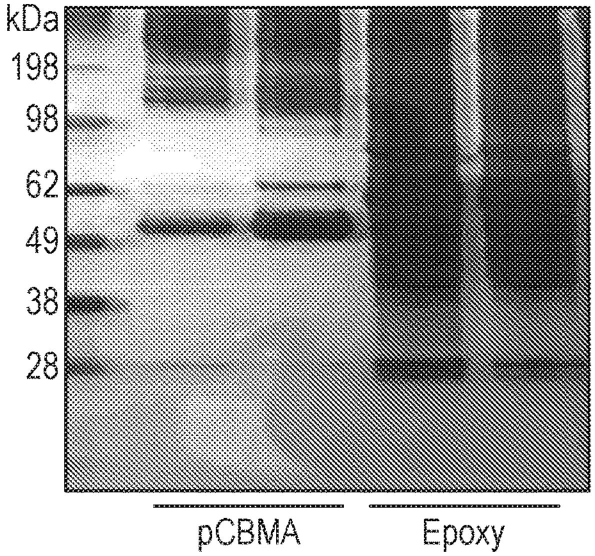

Assay Development for Isolation and Detection of Neuron-Derived Exosomes in Blood To specifically isolate exosomes derived from neuronal cells an immunoaffinity-based capturing approach was used with an antibody against the neuronal L1 adhesion molecule (L1CAM) covalently bound to magnetic microbeads. L1CAM belongs to a group of cell adhesion molecules that are primarily expressed in the nervous system and was previously shown to be a surface marker of neuron-derived exosomes isolated from multiple sources, including blood [15]. The inventors further developed this assay to minimise contamination from peripheral sources. To this end, the inventors produced magnetic beads (~2.4 μm) pre-coated with a zwitterionic polymer poly(carboxybetaine methacrylate) pCBMA, via reversible addition fragmentation chain-transfer (FIG. 5). Successful polymerisation of pCBMA on beads was shown by attenuated total IR reflection spectroscopy when compared to iron oxide beads (FIG. 6A). The antifouling properties of the coated beads were confirmed by reduced non-specific adsorption of bovine serum albumin or total serum protein (FIGS. 6B and 6C) when compared to commercially available epoxy beads, both conjugated to anti-HA antibodies. The carboxylic acid groups of pCBMA were then activated and cross-linked to anti-L1CAM antibodies and assessed for immunocapture of neuronal exosomes in serum (FIG. 7A). Firstly, the inventors showed by SEM that exosomes bound to anti-L1CAM conjugated pCBMA coated beads but not control beads (FIG. 7B). Secondly, the inventors tested and confirmed by immunoblotting the presence of both surface (L1CAM, CD81) and internal (syntenin-1, tsg101) exosome markers in lysates of vesicles captured by anti-L1CAM conjugated pCBMA coated magnetic beads (FIG. 7C). Thirdly, the inventors profiled the total proteomic composition in L1CAM-captured exosomes from pooled human serum by mass spectrometry and identified 512 proteins. The inventors used gene ontology (GO) term analysis to define enriched functions or components within these proteins. Enrichment scores, the degree to which a list of proteins in a GO term are represented within the protein list when compared to the total list of proteins tested, were plotted for GO terms that were significant (p value threshold of $10^{-3}$). The analysis revealed terms enriched in exosomes and related extracellular vesicle functions (FIG. 7D). Among the identified proteins were multiple bona fide exosome markers such as CD9, syntenin-1, 14-3-3 zeta/delta (YWHAZ), neural cell adhesion protein (N1CAM) as well as the protein clusterin (FIG. 7E). For targeted analysis of protein concentration in immunocaptured exosomes the inventors developed a triplex analysis of L1CAM-positive exosomes for total α-synuclein, clusterin and syntenin-1 and demonstrated specific detection of these markers in immunocaptured exosomes (FIG. 8).

Fourier Transform Infrared-Attenuated Total Reflectance (FTIR-ATR)

Appropriate amount of the prepared pCBMA magnetic beads were wash with ethanol and ultrapure water and dried at 50° C. for FTIR-ATR analysis (Bruker Vertex 80, Bruker Corporation, Ettlingen, Germany). CBMA Monomer and uncoated magnetic beads were used as controls.

Immunoblotting

Immunocaptured exosomes were lysed in LDS buffer (Thermo Fisher) and resolved using sodium dodecyl sulfate polyacrylamide gel electrophoresis (SDS-PAGE), transferred onto polyvinylidene fluoride membranes (PVDF, Invitrogen) and immunoblotted with antibodies against syntenin-1 (ab133267, Abeam), CD81 (sc-5275, Santa Cruz), Tsg101 (ab125011, Abcam) and L1 CAM (ab80832, Abeam). All antibodies were used at 1:1,000 dilution. Following incubation with a horseradish peroxidase-conjugated secondary antibody (GE Healthcare) (1:10,000 dilution), chemiluminescence was used for immunodetection (ChemiDoc, Bio-Rad).

SEM

Immunocaptured exosomes were fixed in 2% glutaraldehyde on clean silicon wafer and washed twice with PBS. After natural evaporation, the samples were coated with around 5 nm platinum using a sputter coater (Cressington) and imaged with a scanning electron microscope at 5 kV (Zeiss Crossbeam 540).

Mass Spectroscopy

Immunocaptured exosomes were lysed in RIPA buffer for 15 min at room temperature. Lysates were reduced using dithiothreitol and alkylated with iodoacetamide. Exosomal proteins were isolated with methanol-chloroform precipitation and digested using 0.1 μg/μL of sequencing grade modified porcine trypsin (Promega) diluted in NH4HCO3. Peptides were purified using a C18 spin column (Pierce). The eluted peptides containing acetonitrile were evaporated in a Speedvac (Thermo scientific) to 10 μL and then adjusted to 10 μL with 2% acetonitrile, 0.1% formic acid in ultrapure water. Samples were subsequently analyzed by nanoUPLC-MS/MS using a Waters, nanoAcquity column, 75 μm×250 mm, 1.7 μm particle size, and a gradient of 1-40% acetonitrile in 60 min at a flow rate of 250 nL/min. Mass spectrometry analysis was performed on a Thermo LTQ Orbitrap Velos (60,000 Resolution, Top 20, CID, Waltham, MA, USA). Raw MS data were analyzed using Progenesis QI for Proteomics software (v3.0; Nonlinear Dynamics, Newcastle upon Tyne, UK). MS/MS spectra were searched against the UniProt *Homo sapiens* Reference proteome (retrieved Jan. 6, 2017) using Mascot (v2.5.1; Matrix Science, Inc., Boston, MA), allowing for a precursor mass tolerance of 10 ppm and a fragment ion tolerance of 0.05 Da.

Example 2

The aim of this experiment was to assess the clinical utility of serum neuronal exosomes in patient stratification or prediction across the spectrum of Parkinson's disease versus neurodegenerative conditions characterised by non-α-synuclein proteinopathy.

Methods

Patient Populations

A total of 638 subjects were included in this study (Table 1). Serum samples and clinical data were collected from patients with polysomnographically confirmed RBD (n=53), PD (n=275), Dementia with Lewy bodies (n=21, DLB), Frontotemporal Dementia including the behaviour variant or primary progressive aphasia (n=65 FTD), Progressive supranuclear palsy, PSP (n=35) and Corticobasal Syndrome, CBS (n=45). Healthy controls (n=144, HC) were of similar age and sex.

Patients and controls were recruited from three different centres: The Oxford Parkinson's Disease Centre Discovery cohort, the Kiel-PD cohort and the Bresica cohort.

Sera from neuropathologically confirmed cases of DLB with relatively pure α-synuclein pathology (n=10) and healthy controls (n=10) were used.

Longitudinal serum samples were assessed from Parkinson's (n=40) and control (n=14) individuals.

TABLE 1

The subject used in this study.

| | RBD | PD | PDD | DLB | HC | FTD | PSP | CBS |
|---|---|---|---|---|---|---|---|---|
| Number of individuals | 53 | 230 | 45 | 21 | 144 | 65 | 35 | 45 |
| Male (Female) | 50 (3) | 148 (82) | 34 (11) | 6 (15) | 94 (50) | 38 (27) | 18 (17) | 27 (18) |
| Age at examination, mean | 63.8 | 66.3 | 71.5 | 68.5 | 60.2 | 62.5 | 68.0 | 61.1 |
| Duration of disease | na | 7.67 | 8.28 | na | na | na | na | na |
| UPDRS | na | 24.90 | 39.58 | 20.90 | 2.65 | na | 24.48 | 22.49 |
| MoCA | 25.40 | 27.32 | 18.20 | 16.27 | 26.5 | na | 21.40 | 22.30 |

Exosome Immunocapture

Blood samples were collected, serum was isolated, aliquoted and frozen at −80° C. until further use.

For exosome isolation a 3-step sequential spin (300 g for 10 min, 2000 g for 20 min, and 10,000 g for 30 min) was used to remove cellular debris, proteins aggregates and fatty material in the serum. The supernatant, i.e. pre-cleared serum, was obtained for immunocapture using the coated beads described in Example 1. The immunobeads were incubated at 4° C. overnight and bead-exosomes complexes were collected and washed. Isolated exosomes were lysed in 1% triton X-100 in PBS with 4% protease inhibitors at room temperature for exosomal protein quantification.

Detection of Exosomal Proteins

Electrochemiluminescence (ECL) was performed in 96-well Meso Scale Discovery (MSD) U-Plex plates that enable multiplexing of markers in the same exosome preparation. All steps were performed at room temperature. Three unique linkers for the selected markers (syntenin-1, clusterin, and α-synuclein) were used according to the manufacturer's protocol (MSD). The plates were coated with biotinylated capture antibodies, and exosome lysates or recombinant protein standards followed by detection antibodies with Sulfo-TAG-labelling were added. The plates were read using the MSDECL platform (QuickPlex SQ 120) and data were analysed.

Antibody pairs for clusterin and α-synuclein were provided by MSD and pre-conjugated with biotin and ruthenium tag. Additive-free anti-syntenin-1 goat polyclonal antibody (PAB7132, Abnova) and anti-syntenin-1 rabbit monoclonal antibody (ab236071, Abcam) were conjugated with biotin and ruthenium and used as capture and detection antibodies respectively. For phosphorylated α-synuclein at serine129 (pSer129) detection, the antibody pair used consists of a biotinylated antibody against pSer129 α-synuclein (11A5, purified from PTA-8222 hybridoma cell line, ATCC) acting as capture antibody and a ruthenium labelled antibody against total α-synuclein (4B12, Biolegend) acting as the detection antibody.

For combined exosomal α-synuclein, clusterin and syntenin-1 the inventors developed triplex MSD and demonstrated specific detection of these markers in immunocaptured exosomes (FIG. 8) and for all assays the inventors assessed dynamic range and lower limit of detection (FIGS. 9 and 10).

Study Design and Statistical Analyses

For multiple comparisons the inventors performed non-parametric statistical testing as the data were not normally distributed (Kruskal-Wallis one-way analysis of variance with the Dunn test for post hoc comparison between individual pairings). Relationships between exosome markers and disease duration, gender, MoCA scores and UPDRS motor scores were analyzed with bivariate correlation using Pearson's correlation coefficients. To assess the performance of the proposed biomarker in separating α-synucleinopathies from controls and define cut-off values the inventors used the Kiel and Brescia cohorts as a training group (n=314) and the Oxford cohort as a validation group (n=105). Data from these groups were analysed using receiver operating characteristic (ROC). The "optimum" cut-off point was determined by Youden's index, i.e. the value associated with the maximal value of sensitivity+specificity−1. Values with $p<0.05$ were regarded as significant. Logistic regression analysis was used to determine the best combination of different protein markers (clusterin and α-synuclein) for discriminating between diagnostic groups or sets of subgroups. Longitudinal samples were analyzed using linear mixed model to investigate the correlation between biomarker concentration and duration, with sample at first visit treated as baseline. The robust regression and outlier removal method (ROUT) was applied to test for outliers Logistic regression and linear mixed model were performed using MATLAB (MATLAB and Statistics Toolbox Release 2014a The MathWorks, Inc., Natick, Massachusetts, United States).

Results

Neuron-Derived Exosomal α-Synuclein is Increased Across the Spectrum of Lewy Body Pathology The inventors blindly analysed serum samples from 638 subjects across three transnational cohorts to comprehensively assess the blood-based assay and investigate the role of neuron-derived exosomal α-synuclein as a biomarker across the spectrum of Lewy body pathology by assaying patients in the prodromal, motor and dementing stage. To this end, the inventors separated the PD participants according to MoCA scores, corrected for education into those with pure motor PD or PD dementia. Dementia in the context of PD was defined as MoCA screening score of less than 21/30 (29) at the time of sample collection. Thus, the inventors subsequently analysed blindly subgroups of motor PD (n=230) or PD with dementia (n=45). The inventors also included a group of 21 cases with the clinical diagnosis of DLB, 10 of which were confirmed at autopsy. A group of idiopathic RBD without motor signs (n=53) was also used as a surrogate of prodromal PD as prospective cohort studies have observed a very strong association between RBD and subsequent clinically defined α-synucleinopathy, with up to 80% of cases converting primarily to PD or DLB (30,31).

Figure 1A:
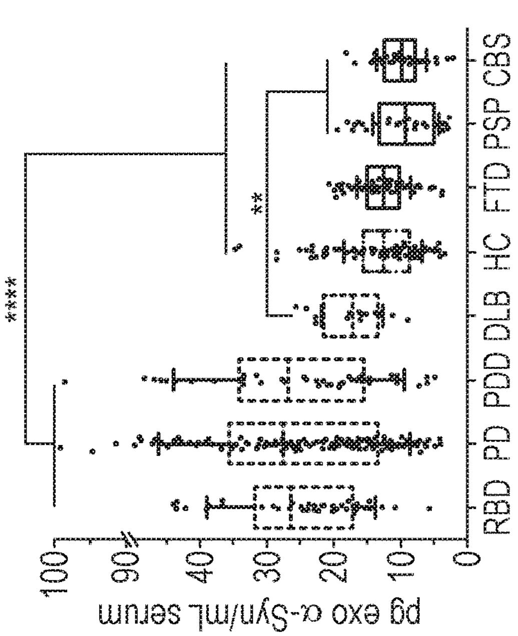
FIG. 1 shows α-synuclein content in the neuron-derived exosomes in the blood of the samples from patients across the spectrum of Lewy body pathology, i.e. having conditions characterised by α-synucleinopathy. (A) Boxplots of mean total α-synuclein across the spectrum of conditions with Lewy body pathology (REM sleep behaviour disorder (RBD), motor PD, PD dementia (PDD), dementia with Lewy bodies (DLB)) and unrelated neurodegenerative conditions (frontal temporal dementia (FTD), progressive supranuclear palsy (PSP), corticobasal syndrome (CBS)) as well as age- and sex-matched controls. Two-fold increase in the content of α-synuclein was detected in L1 CAM-positive exosomes isolated from conditions characterized by α-synuclein pathology. (B) At the limit of detection (0.5 pg/ml), PSer129 α-synuclein was detected only in a small subgroup of PD patients that were tested (28.6%). No significant correlation was seen between exosomal α-synuclein and either Unified Parkinson's Disease Rating Scale (UPDRS) (panel C, r=0.0267) or Montreal Cognitive Assessment (MoCA) (panel D, r=0.0621). $^{}p<0.01$, $^{**}p<0.0001$. Mean values with interquartile range of exosomal markers and whisker range using standard deviation with coefficient of 1 were used in the boxplots.

The inventors found that α-synuclein was elevated in RBD, PD and DLB exosomes by ~2-fold compared to controls or other proteinopathies (FIG. 1A). Specifically, α-synuclein content in L1 CAM-positive exosomes was similarly elevated (data shown as mean+/−SD) in RBD (26.44±12.64 pg/mL), motor PD (27.44±18.82 pg/mL) and PD with dementia (PDD 27.76±17.25 pg/mL) when compared to healthy subjects (HC, 12.91±5.93 pg/mL). α-Synuclein was also elevated in DLB (17.23±4.58 pg/mL). The inventors demonstrated the association between increased release of α-synuclein in neuronal exosomes and Lewy body pathology by testing sera taken pre-mortem in autopsy confirmed control and DLB cases (n=10 per group). In these two subgroups, mean neuronal exosome-associated α-synuclein was 17.60±5.86 pg/mL in DLB and 10.50±4.60 pg/mL in controls (1.7-fold increase, p=0.0097). As expected, exosomal α-synuclein concentration was much lower compared to reported levels of free total α-synuclein in blood (10-17 ng/mL) (7,10).

To assess the abundance of neuron-derived exosomal α-synuclein in unrelated neurodegenerative conditions, the inventors included patients with FTD (n=65) which is pathologically characterised primarily by tau or TDP-43 aggregation, and patients with PSP (n=35) and CBS (n=45) which are pathologically characterised by fibrillar aggregates of four repeat tau. The inventors found that α-synuclein content in L1CAM-positive exosomes from these diseases is similar to HC as shown in FIG. 1A (FTD, 12.60±4.03 pg/mL; PSP, 9.20±4.90 pg/ml; CBS, 9.93±3.68 pg/mL).

Figure 1B:
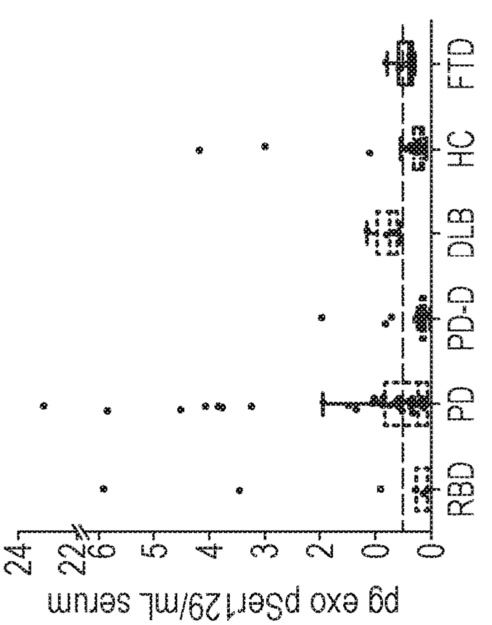
Figure 1C:
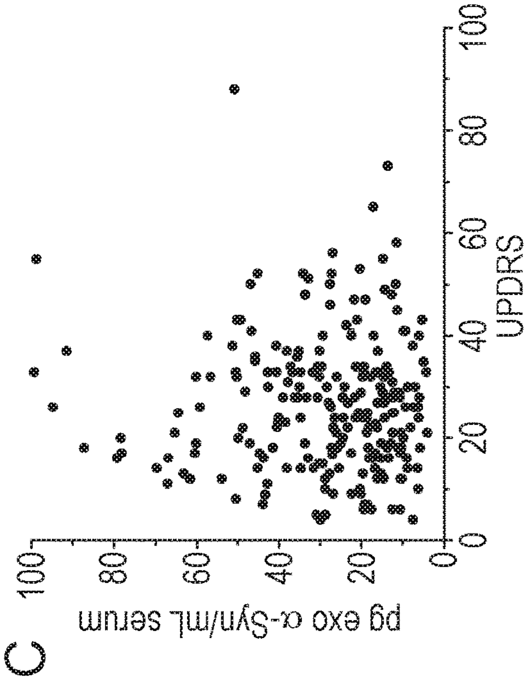
Figure 1D:
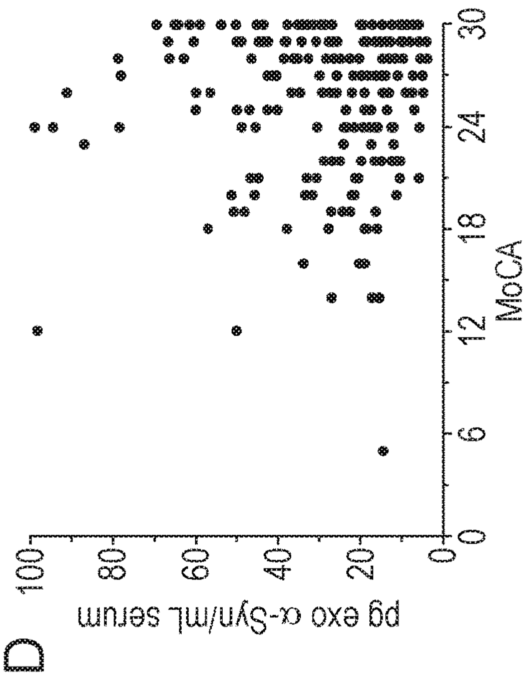

In the first 226 subjects, the inventors also determined whether phosphorylated α-synuclein at serine 129 (pSer129) is detected in L1CAM-positive exosomes and has value as a blood-based biomarker. pSer129 α-synuclein is the main disease-associated modification that accounts for more than 90% of α-synuclein found in Lewy bodies (32). This analysis showed that only a small number of individuals have a detectable level of pSer129 α-synuclein in neuronal exosomes. Interestingly, when a cut-off value of 0.5 pg/ml was applied (FIG. 1B) which is within the limit of detection of the assay (FIG. 10), pSer129 α-synuclein was elevated in a subgroup of (33) PD patients (28.6% of total PD tested). In this subpopulation, pSer129 α-synuclein correlated with disease duration longer than 7.3 years (r=0.26, p=0.0263) and UPDRS (r=0.34, p=0.0495) but not MoCA (r=0.006, p=0.3643). Unlike previous studies (15,13), the inventors did not detect any significant correlation between exosomal α-synuclein and either UPDRS (r=0.0267) or MoCA (r=0.0621) as shown in FIGS. 1C and 1D.

Multiplexed Measurement of α-Synuclein and Clusterin Improved the Predictive Value of the Exosome Test Across α-Synucleinopathies.

Figure 2A:
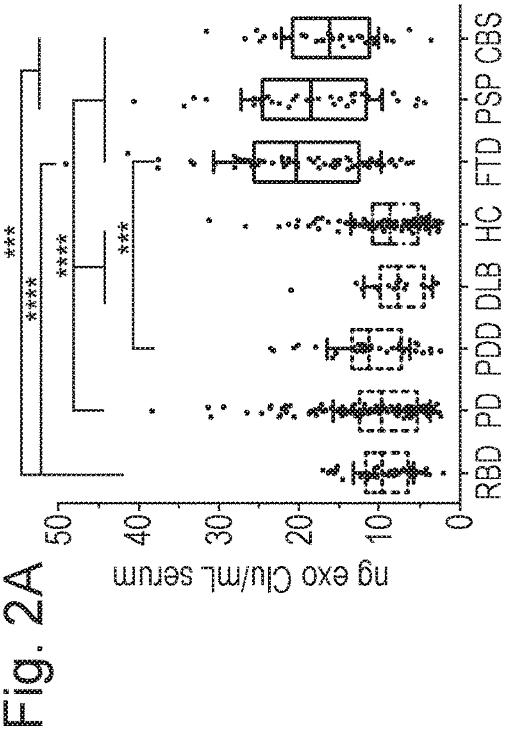
FIG. 2 shows clusterin content in the neuron-derived exosomes in the blood of the samples is increased in tauopathies and when combined with α-synuclein improved the differential diagnosis. (A) Clusterin (clu) release in serum neuronal exosomes is increased in FTD, PSP and CBS but not RBD, PD, PDD, DLB or age- and sex-matched controls.
Figure 2B:
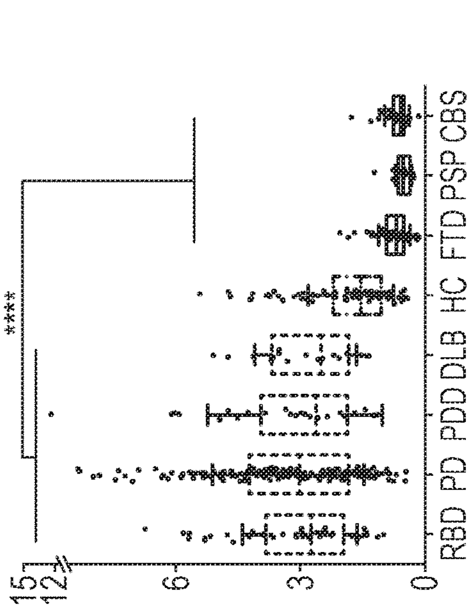
Figure 2C:
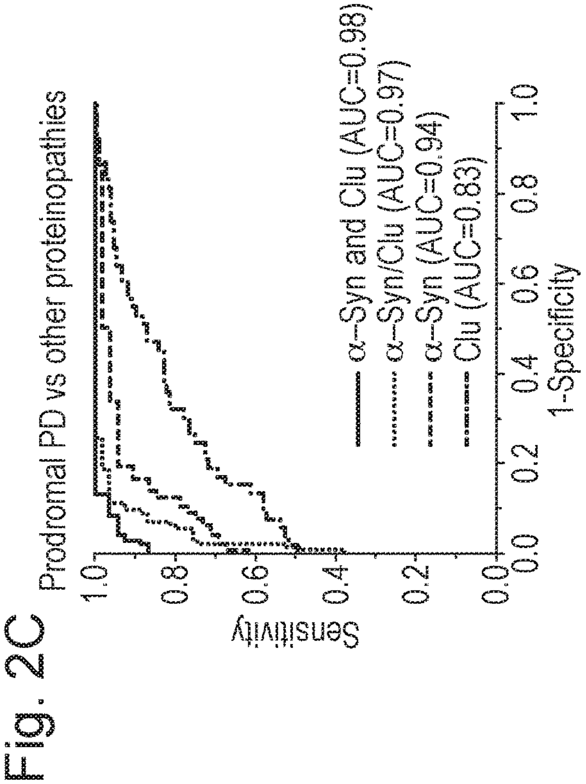
Figure 2D:
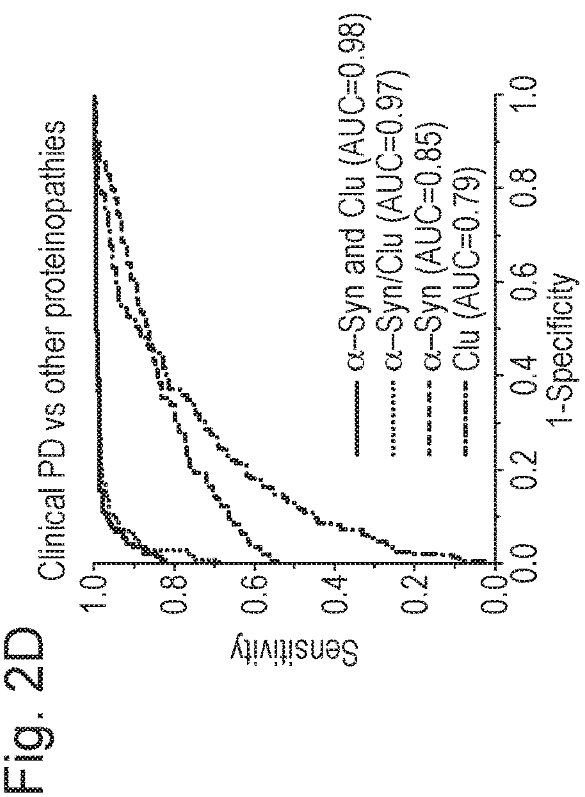

To assess the value of multiplexed exosome measurements, the inventors selected clusterin as an additional marker because it was the most abundant exosome-associated protein detected in the mass spectrometric analysis (FIG. 7E). Clusterin was previously identified as a risk gene (33,34) for dementia. The inventors therefore hypothesized that the quantification of clusterin in neuronal exosomes may aid the stratification of patients with cognitive defects or the separation of those with alternative pathology. Strikingly, the inventors found that clusterin was elevated in FTD (20.22±10.47 ng/mL), PSP (18.42±8.84 ng/ml) and CBS (16.16±6.07 ng/ml) (FIG. 2A) and not elevated in RBD (9.55±3.71 ng/mL), clinical PD (9.72±6.02 ng/mL) or HC (8.67±4.92 ng/mL). This differential abundance of clusterin in unrelated proteinopathies suggests that integration of clusterin in a blood-based PD exosome test could be of value in distinguishing patients with predominantly non-α-synuclein pathology. In contrast, the generic exosomal protein syntenin-1 did not exhibit a disease-specific distribution with sufficient separation to contribute as a biomarker (FIG. 11).

To further evaluate the clinical potential of combined α-synuclein and clusterin measurements in L1 CAM-positive exosomes as biomarkers, the inventors assessed α-synuclein to clusterin ratio and applied a logistic regression model for the combination of these markers. Both analyses showed that combined α-synuclein and clusterin measurements exhibited an improved AUC, sensitivity, and specificity estimates for differential diagnosis in predicting clinical PD versus other proteinopathies, with an AUC=0.98 (sensitivity 0.95; specificity 0.93), even in the prodromal phase of PD (RBD vs other proteinopathies, AUC=0.98, sensitivity 0.94, specificity 0.96) as shown in FIG. 2 and table 2.

Table 2. Summary of ROC Analyses in Patient Group Across Cohorts Comparing Synucleinopathies and Controls or Other Proteinopathies Using α-Synuclein, Clusterin and Composite Marker (α-Synuclein and Clusterin).

Composite marker was analysed with logistic regression. ROC-based separations were applied where there is significant difference between two groups. High-performance markers are shown in bold.

| | α-Syn (pg/mL) | | | | Clu (ng/mL) | | | |
|---|---|---|---|---|---|---|---|---|
| | AUC | Cut-off | Spec | Sens | AUC | Cut-off | Spec | Sens |
| RBD vs. HC | 0.88 | 14.55 | 0.72 | 0.94 | — | — | — | — |
| RBD vs. FTD+ PSP+ CBS | 0.94 | 14.61 | 0.81 | 0.94 | 0.83 | 12.49 | 0.81 | 0.72 |
| PD vs. HC | 0.79 | 14.50 | 0.78 | 0.72 | — | — | — | — |
| PD vs. FTD+ PSP+ CBS | 0.83 | 14.56 | 0.81 | 0.72 | 0.82 | 12.06 | 0.74 | 0.74 |
| PD+ PDD vs. HC | 0.79 | 14.50 | 0.72 | 0.74 | — | — | — | — |
| PD+ PDD vs. FTD+ PSP+ CBS | 0.85 | 14.38 | 0.80 | 0.74 | 0.79 | 12.39 | 0.71 | 0.72 |

-continued

| | | | | | | | | |
|---|---|---|---|---|---|---|---|---|
| RBD, PD, PDD vs. HC | 0.82 | 0.80 | 0.72 | 14.50 | — | — | — | — |
| RBD, PD, PDD vs. FTD+ PSP+ CBS | 0.86 | 14.36 | 0.80 | 0.83 | 0.80 | 12.42 | 0.73 | 0.76 |
| RBD, PD, PDD, DLB vs. HC | 0.82 | 14.45 | 0.75 | 0.79 | — | — | — | — |
| RBD, PD, PDD, DLB vs. FTD+ PSP+ CBS | 0.83 | 14.32 | 0.78 | 0.80 | 0.87 | 12.45 | 0.82 | 0.85 |
| HC vs FTD− PSP− CBS | — | — | — | — | 0.86 | 12.41 | 0.81 | 0.82 |

| | α-Syn/Clu | | | | Composite of α-Syn and Clu | | | |
|---|---|---|---|---|---|---|---|---|
| | AUC | Cut-off | Spec | Sens | AUC | Cut-off (probability) | Spec | Sens |
| RBD vs. HC | 0.78 | 2.18 | 0.74 | 0.74 | 0.81 | 0.20 | 0.72 | 0.92 |
| RBD vs. FTD+ PSP+ CBS | 0.97 | 1.38 | 0.89 | 0.96 | 0.98 | 0.66 | 0.93 | 0.95 |
| PD vs. HC | 0.77 | 1.95 | 0.70 | 0.73 | 0.84 | 0.54 | 0.73 | 0.77 |
| PD vs. FTD+ PSP+ CBS | 0.98 | 1.13 | 0.92 | 0.94 | 0.96 | 0.68 | 0.96 | 0.92 |
| PD+ PDD vs. HC | 0.77 | 1.95 | 0.70 | 0.72 | 0.84 | 0.58 | 0.70 | 0.79 |
| PD+ PDD vs. FTD+ PSP+ CBS | 0.97 | 1.13 | 0.92 | 0.94 | 0.98 | 0.41 | 0.96 | 0.94 |
| RBD, PD, PDD vs. HC | 0.76 | 1.21 | 0.71 | 0.73 | 0.85 | 0.61 | 0.71 | 0.82 |
| RBD, PD, PDD vs. FTD+ PSP+ CBS | 0.96 | 1.39 | 0.89 | 0.89 | 0.96 | 0.79 | 0.97 | 0.92 |
| RBD, PD, PDD, DLB vs. HC | 0.81 | 2.08 | 0.76 | 0.79 | 0.83 | 0.65 | 0.77 | 0.75 |
| RBD, PD, PDD, DLB vs. FTD+ PSP+ CBS | 0.95 | 1.40 | 0.93 | 0.92 | 0.96 | 0.76 | 0.96 | 0.92 |
| HC vs FTD− PSP− CBS | 0.89 | 1.41 | 0.82 | 0.84 | 0.89 | 0.59 | 0.81 | 0.86 |

To assess the consistency of exosomal α-synuclein in differentiating clinical PD from healthy subjects across populations, the inventors applied a two-stage design model: A training group of 314 subjects from the Kiel and Brescia cohorts was used to identify an optimal cut-off value, which was then applied to an independent validation group of 105 subjects from the Oxford cohort. This revealed that at 14.21 pg/ml, the assay exhibits a consistent performance (training versus validation) with an AUC of 0.86, sensitivity of 0.82 vs 0.85, specificity of 0.71 vs 0.74, and positive predictive value of 0.83 vs 0.89 and negative predictive value of 0.72 vs 0.68 as shown in FIG. 3.

Longitudinal Trajectories of Exosome-Associated α-Synuclein and Clusterin with Disease Progression To investigate the variability of neuron-associated exosomal markers within an individual over the course of the disease, the inventors blindly analysed prospective longitudinal samples from the Oxford cohort. A linear mixed model was applied to fit the longitudinal values of exosomal α-synuclein and clusterin with time from first sampling as a covariant, and patients stratified by level at initial visit in relation to median value. Longitudinal sample numbers for PD, PDD and controls are summarized in FIG. 4. Overall, the gradient did not differ significantly from zero for either stratum of α-synuclein or clusterin when comparing clinical PD (PD or PDD or combination) or controls. This analysis indicates that neuron-derived exosomal α-synuclein levels remain elevated within individuals with PD over a 5-year period with persistent separation from controls as shown in FIG. 4.

Discussion

This study presents a blood-based test for clinical utility in α-synucleinopathies, such as PD. This analysis is the largest multicentre study of neuronal exosome proteins in serum that has defined parameters for their potential utility in clinical practice: as a single cross-sectional measurement, serum neuronal exosome-associated α-synuclein and clusterin performs best as a predictive marker of underlying α-synucleinopathy versus another proteinopathy or healthy subjects in clinical and prodromal PD, outperforming any previously reported blood-based assay or CSF total or pathogenic α-synuclein (7,35). This enhanced performance of the serum neuronal exosome test across samples collected at multiple sites is at least in part due to improved specific immunocapture using zwitterionic coating that resists non-specific binding (36). The consistency of the assay of exosomal α-synuclein across populations and stability over disease progression when assessed within individuals suggests that it could be considered as a pharmacodynamic biomarker for α-synuclein targeting therapies in PD and related diseases.

The finding of increased neuronal exosome α-synuclein levels in PD and PDD compared to controls by ~2-fold across three studies firmly establishes that increased exosomal α-synuclein is a validated disease-relevant observation in PD. In addition, the inventors have demonstrated that neuronal exosome α-synuclein levels are elevated in patients with RBD, a group at high risk of developing PD and not in other neurodegenerative conditions (FTD/PSP/CBS). This observation in clinical samples suggests that jettison of α-synuclein from neuronal tissues is a specific pathophysiological response across the spectrum of α-synucleinopathies that precedes the clinical diagnosis. In this context, pSer129 α-synuclein was not consistently detected in neuronal exosomes from blood except in a PD subgroup. Thus, at least in the early stages of disease, exosomal release appears to concern primarily non-pathogenic forms of α-synuclein whereas exosome-associated pathogenic α-synuclein may occur in advanced stages, signifying a more severe motor phenotype.

Interestingly, exosomal clusterin but not α-synuclein was elevated in FTD, PSP and CBS, three neurodegenerative conditions that are characterised pathologically by primarily tau or TDP-43 proteinopathy and minimal α-synuclein pathology (37). Although total serum clusterin is elevated in Alzheimer's disease (AD), this association is controversial (38,39) and may involve Aβ-independent pathways (40). The data in this study suggest that the neuron-associated exosomal fraction of clusterin could be useful as a diagnostic biomarker for neurodegenerative conditions characterised by tauopathy. In the context of this study, integration of clusterin quantification could aid the separation of patients with predominantly non-α-synuclein pathology. Given that concomitant proteinopathies are frequently found in dementias (3,37), clusterin in combination with α-synuclein could be especially useful in stratifying those patients with cognitive involvement (e.g. PDD, DLB) most likely to benefit from therapies targeting α-synuclein. In support of this notion, the inventors found that combined serum neuronal exosome α-synuclein and clusterin measurements or their ratio improved the sensitivity and specificity of the blood-based exosome test with an AUC of 0.98.

The inventors previously showed that serum exosome number or size does not differ between PD patients and controls (12). This finding, and the distinct protein pattern across groups reported here (i.e. α-synuclein being highest in RBD/PD/PDD/DLB vs clusterin being highest in FTD/PSP/CBS) suggests that changes in L1CAM-positive exosome composition is the most likely explanation for these observations. Genome-wide association studies and functional interrogation of monogenic causes of PD indicates that protein trafficking to endosomes and lysosomes is relevant to the pathogenic cascade (41). Exosomes are derived from intraluminal vesicles within maturing (late) endosomes, also known as multivesicular bodies (MVB). The content of MVB is typically destined for degradation when they fuse with lysosomes. An alternative destination for MVB is the plasma membrane and the release of exosomes. It is therefore possible that progressive failure of intraneuronal trafficking from endosomes to lysosomes leads to increased exosomal release of α-synuclein. This model would be consistent with a number of cell-based studies, which showed that α-synuclein is trafficked to endosomes and undergoes lysosomal degradation (42, 43, 44) whereas inhibition of lysosomal function increased α-synuclein release in exosomes in conditioned media (45, 46, 47). Based on this model, the reported decrease in CSF total α-synuclein in PD (7,8) could be secondary to an adaptive efflux into serum exosomes in response to defective neuronal handling of the protein.

The strengths of this study include its multicentre nature and large sample size across the spectrum of α-synucleinopathies and inclusion of unrelated proteinopathies, which exceeds any previous exosome investigation in PD. This allowed the inventors to use training and validation groups from distinct cohorts to establish cut-off values for exosomal α-synuclein and demonstrate the consistent performance of the assay. The availability of longitudinal samples enabled the inventors to show the stability of the marker over time. Limitations include the need to replicate the relevance of clusterin in additional patient cohorts.

The finding that neuron-derived exosomal α-synuclein is consistently elevated across populations and remains elevated within individuals with PD when tested over a 5-year period, suggests that measurements of the neuronal exosome content of α-synuclein in serum could be used as a proxy to its intraneuronal processing and thus a marker for monitoring disease-modifying therapies that target α-synuclein in brain, especially in the early stages of PD. Given the high risk of RBD conversion to PD (48) and the wide acceptance of RBD patients as potential candidates for neuroprotective therapies against PD, this study also defined the parameters for an easily accessible, objective readout of underpinning Lewy pathology in this group of prodromal PD. Notably, combined measurements of neuronal exosome content of α-synuclein and clusterin improved the predictive test value of a primary α-synucleinopathy versus an alternative proteinopathy (AUC 0.98). Therefore, assaying of neuron-derived exosomal α-synuclein and clusterin in serum is a blood-based predictive test of an evolving α-synuclein pathology, such as PD, and this could be introduced in clinical trials for α-synuclein-targeting therapy targeting at-risk populations.

Example 3

This example further demonstrates the clinical utility of α-synuclein measurement, and optionally in combination with clusterin measurement, in serum neuronal exosomes as biomarkers across the spectrum of Parkinson's disease, multiple system atrophy and other proteinopathies.

Materials and Methods

A total of 664 subjects were included in this study (Table 3). Serum samples and clinical data were collected from patients with polysomnographically confirmed RBD (n=65), PD (n=275), Dementia with Lewy bodies (n=14, DLB), multiple system atrophy (n=14, MSA), Frontotemporal Dementia including the behaviour variant or primary progressive aphasia (n=65, FTD), Progressive supranuclear palsy (n=35, PSP) and Corticobasal Syndrome (n=45, CBS). Healthy controls (n=144, HC) were of similar age and sex.

The levels of α-synuclein, clusterin and syntenin-1 in L1 CAM-positive exosomes from serum samples were determined as detailed in Example 2.

Statistical analyses were carried out as detailed in Example 2.

Table 3. Summary of Individual Cohort Characteristics and Concentrations of Exosome Markers.

Data represent the mean at the time of sample collection. UPDRS and MoCA were available in 48% of healthy control. RBD=rapid eye movement sleep behaviour disorder, PD=Parkinson's disease, PDD=Parkinson's disease with dementia, DLB=Dementia with Lewy bodies, MSA=Multiple system atrophy, HC=healthy controls, FTD=Frontotemporal dementia including the behaviour variant or primary progressive aphasia, PSP=Progressive supranuclear gaze palsy, CBS=Corticobasal syndrome. *Post-mortem cases.

| Sites | | RBD | PD | PDD | DLB | MSA | HC | FTD | PSP | CBS |
|---|---|---|---|---|---|---|---|---|---|---|
| Oxford | Number of individuals | 65 | 48 | 26 | 10* | 14 | 31 | — | — | — |
| | Male (Female) | 62 (3) | 36 (12) | 21 (5) | 7 (3) | 10 (4) | 22 (9) | — | — | — |
| | Age | 64.2 ± 8.3 | 62.8 ± 9.3 | 70.2 ± 6.6 | 82.8 ± 7.7 | 68.1 ± 10.8 | 66.3 ± 8.8 | — | — | — |
| | Duration of disease (years) | na | 1.8 ± 2.1 | 3.5 ± 4 | — | 4.9 ± 2.6 | na | — | — | — |
| | UPDRS | 5.1 | 32.9 | 39.6 | — | 27.7 | na | — | — | — |
| | MoCA | 25.5 | 27.1 | 18.2 | — | 27.3 | na | — | — | — |
| | exo α-Synuclein (pg/mL) | 26.69 ± 12.8 | 22.36 ± 9.5 | 25.34 ± 10.6 | 17.23 ± 4.6 | 10.72 ± 4.5 | 12.48 ± 5.1 | — | — | — |
| | exo Clusterin (ng/mL) | 10.01 ± 5.2 | 7.85 ± 3.6 | 9.56 ± 4 | 6.99 ± 3 | 6.84 ± 3.2 | 11.25 ± 2.6 | — | — | — |
| | exo Syntenin-1 (ng/mL) | 32.85 ± 27.1 | 43.31 ± 21.6 | 38.29 ± 22 | 28.10 ± 10.5 | 14.77 ± 5.8 | 33.40 ± 15.9 | — | — | — |
| Kiel | Number of individuals | — | 155 | 15 | — | | 113 | — | — | — |
| | Male (Female) | — | 96 (59) | 11 (4) | — | | 72 (41) | — | — | — |
| | Age | — | 67.5 ± 9.3 | 73.9 ± 8.2 | — | | 59.0 ± 4.8 | — | — | — |
| | Duration of disease (years) | — | 9.30 ± 6.1 | 14.4 ± 6.6 | — | | na | — | — | — |
| | UPDRS | — | 23.44 | 39.2 | — | | na | — | — | — |
| | MoCA | — | 27.54 | 18.47 | — | | na | — | — | — |
| | exo α-Synuclein (pg/mL) | — | 29.32 ± 20.5 | 36.57 ± 24.4 | — | | 12.72 ± 6.1 | — | — | — |
| | exo Clusterin (ng/mL) | — | 10.60 ± 6.4 | 12.77 ± 5.9 | — | | 8.08 ± 5.2 | — | — | — |
| | exo Syntenin-1 (ng/mL) | — | 25.65 ± 20.3 | 38.82 ± 22.5 | — | | 18.81 ± 12 | — | — | — |
| Brescia | Number of individuals | — | 27 | 4 | 11 | | — | 65 | 35 | 45 |
| | Male (Female) | — | 17 (10) | 2 (2) | 7 (4) | | — | 38 (27) | 18 (17) | 27 (18) |
| | Age | — | 65.0 ± 9.4 | 71.0 ± 15.8 | 68.6 ± 4.9 | | — | 62.5 ± 7 | 68.0 ± 7.5 | 61.1 ± 7.2 |
| | Duration of disease (years) | — | na | 18.5 ± 5.8 | 3.4 ± 3.0 | | — | 2.9 ± 2.5 | 2.8 ± 1.8 | 1.9 ± 1.3 |
| | UPDRS | — | 20.11 | 39.75 | na | | — | na | 24.48 | 22.30 |
| | MoCA | — | 26.78 | 16.50 | na | | — | na | 21.40 | 22.49 |

-continued

| Sites | | RBD | PD | PDD | DLB | MSA | HC | FTD | PSP | CBS |
|---|---|---|---|---|---|---|---|---|---|---|
| | exo α-Synuclein (pg/mL) | — | 25.61 ± 19 | 20.96 ± 5.4 | 16.87 ± 3.1 | | — | 12.60 ± 4 | 9.20 ± 4.9 | 9.93 ± 3.7 |
| | exo Clusterin (ng/mL) | — | 7.56 ± 5.8 | 6.39 ± 4.8 | 6.15 ± 5.2 | | — | 22.22 ± 10.5 | 18.42 ± 8.8 | 16.16 ± 6.1 |
| | exo Syntenin-1 (ng/mL) | — | 22.95 ± 10 | 15.92 ± 3.9 | 20.05 ± 5.3 | | — | 20.81 ± 20.9 | 44.31 ± 23 | 54.73 ± 25 |

Results

Neuron-Derived Exosomal α-Synuclein is Increased Across the Spectrum of Lewy Body Diseases Serum samples from 664 subjects across the spectrum of Lewy body pathology were analysed by assaying patients in the prodromal, motor and dementing stage. To this end, the PD participants were separated according to MoCA scores, corrected for education into those with pure motor PD or PD dementia. Dementia within the PD cohorts was defined as MoCA screening score of less than 21/30 (29) at the time of sample collection. Thus, subgroups of motor PD (n=230) or PD with dementia (n=45) were subsequently analysed blindly. A group of 21 cases with the clinical diagnosis of DLB was also included, 10 of which were confirmed at autopsy. A group of idiopathic RBD without motor signs (n=65) was also used as a surrogate of prodromal PD as prospective cohort studies have observed a very strong association between RBD and subsequent clinically defined α-synucleinopathy, with up to 80% of cases converting primarily to PD or DLB (30,31).

Figure 13A:
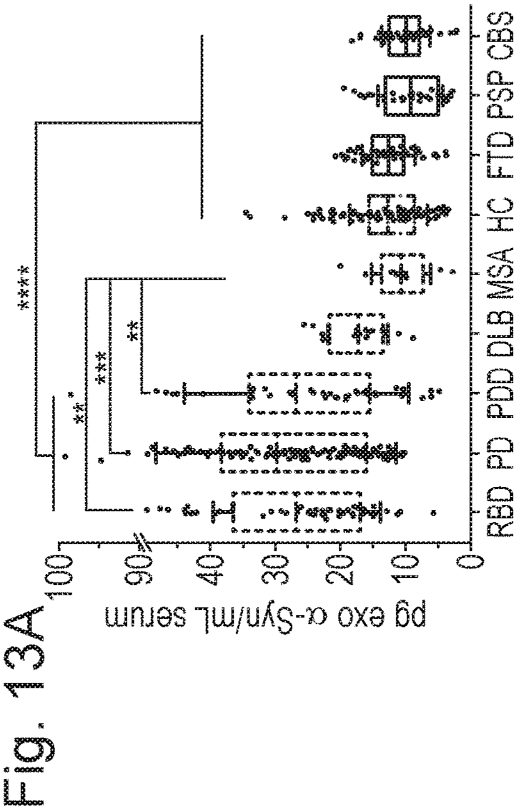
Figure 13B:
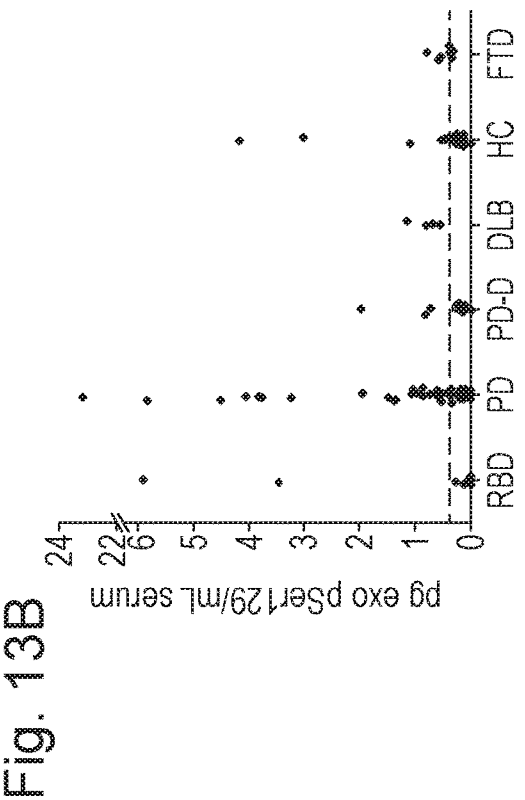

It was found that α-synuclein was elevated in RBD, PD and DLB exosomes by fold compared to controls, MSA or other proteinopathies (FIG. 13A and Table 3). Specifically, α-synuclein content in L1 CAM-positive exosomes is similarly elevated (data shown as mean±SD) in RBD (26.69±12.82 pg/mL), motor PD (27.44±18.82 pg/mL) and PD with dementia (PDD 26.76±17.25 pg/mL) when compared to healthy subjects (HC, 12.71±5.93 pg/mL). α-Synuclein was also elevated in DLB (17.23±4.58 pg/mL). The association between increased release of α-synuclein in neuronal exosomes and Lewy body pathology was demonstrated by testing sera taken pre-mortem in autopsy confirmed control and DLB cases (n=10 per group). In these two subgroups, mean neuronal exosome-associated α-synuclein was 17.60±5.86 pg/mL in DLB and 10.50±4.60 pg/mL in controls (1.7-fold increase, p=0.0097). As expected, exosomal α-synuclein concentration was much lower compared to reported levels of free total α-synuclein in blood (10-17 ng/mL) (7,15). Interestingly, neuron-derived exosomal α-synuclein was not elevated in any of the cases with MSA (10.72±4.49 pg/mL), a disease characterised primarily by oligodendroglial pathology, despite the fact that MSA samples were collected and processed using an identical procedure to PD samples.

To assess the abundance of neuron-derived exosomal α-synuclein in unrelated neurodegenerative diseases, the following patient groups were tested: patients with FTD (n=65) which is pathologically characterised primarily by tau or TDP-43 aggregation, and patients with PSP (n=35) and CBS (n=45) who present with atypical parkinsonism and pathologically are characterised by fibrillar aggregates of four repeat tau. It was found that α-synuclein content in L1 CAM-positive exosomes from these diseases is similar to HC as shown in FIG. 13A (FTD, 12.60±4.03 pg/mL; PSP, 9.20±4.90 pg/ml; CBS, 9.93±3.68 pg/mL).

Figure 13C:
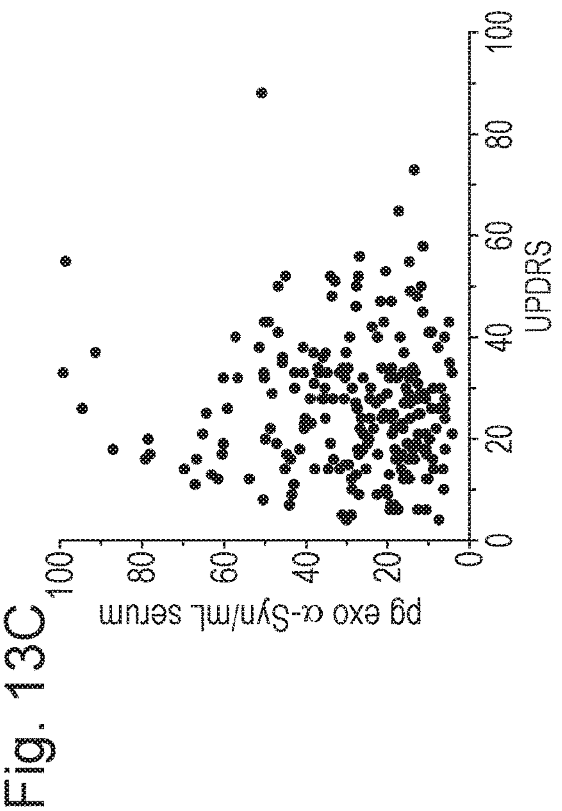
Figure 13D:
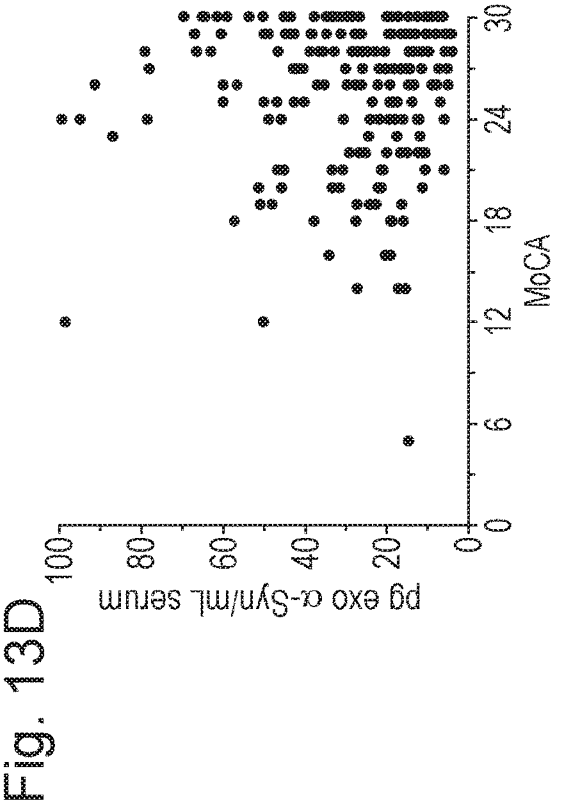
Figures 14A, 14B, 14C:
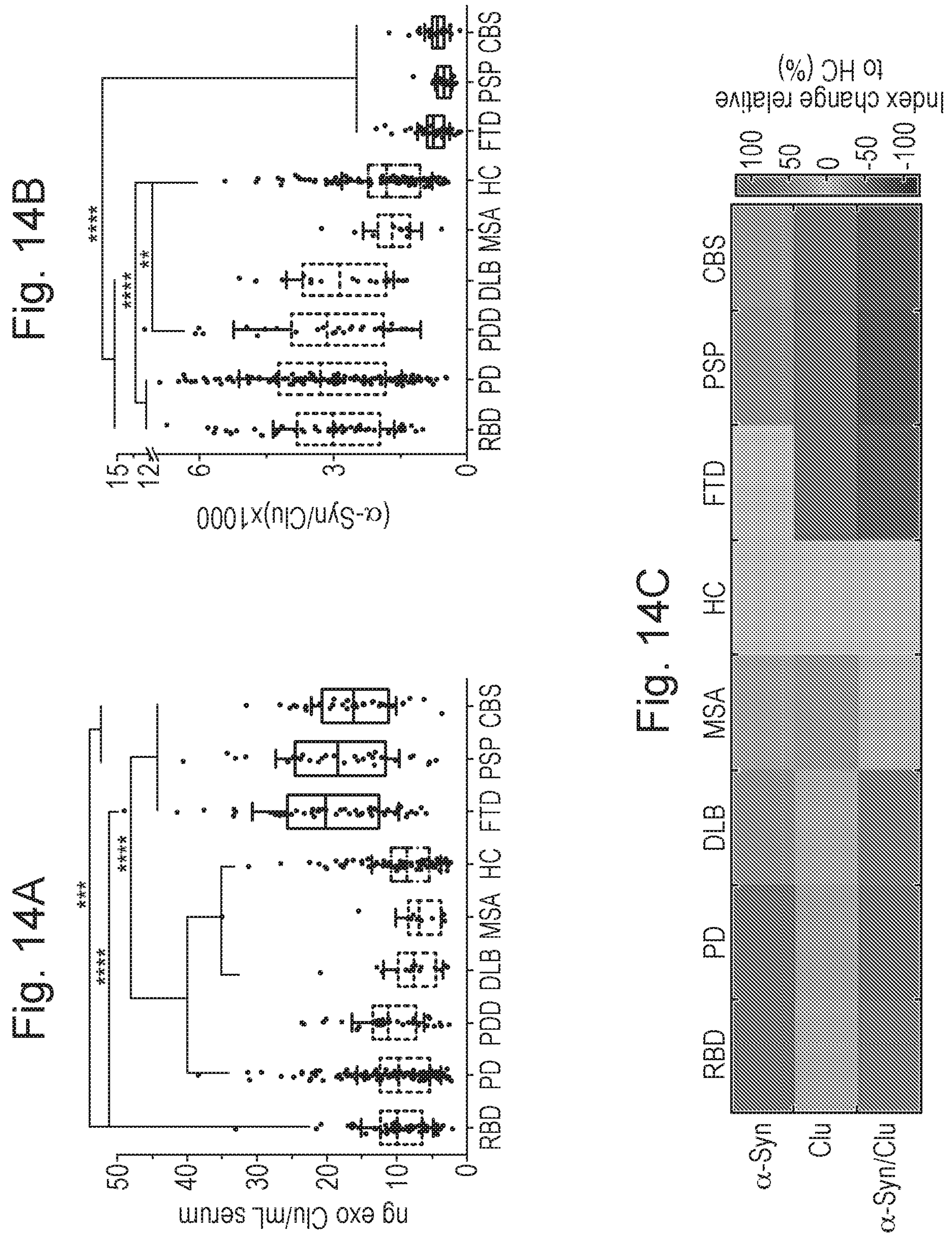

In 226 subjects (18 RBD, 77 PD, 36 PDD, 11 DLB, 69 HC, 15 FTD), it was also investigated whether elevated α-synuclein in Lewy body disease is phosphorylated at serine 129 (pSer129) in L1 CAM-positive exosomes and has a value as a blood-based biomarker. pSer129 α-synuclein is the main disease-associated modification that accounts for more than 90% of α-synuclein found in Lewy bodies (32). This analysis showed that only a small number of individuals have a detectable level of pSer129 α-synuclein in neuronal exosomes. Interestingly, when a cut-off value of 0.5 pg/ml was applied (FIG. 13B) which is within the limit of detection of the assay, pSer129 α-synuclein was elevated in a subgroup of 22 PD patients (28.6% of total PD tested). In this PD subpopulation, pSer129 α-synuclein correlated with disease duration longer than 7.3 years (r=0.26, p=0.0263) and UPDRS (r=0.34, p=0.0495) but not MoCA (r=0.006, p=0.3643). Unlike previous studies (15,13) no significant correlation between exosomal α-synuclein and either UPDRS (r=0.0267) or MoCA (r=0.0621) was detected, as shown in FIGS. 13C and 13D.

α-Synuclein and Clusterin Measurement Improved the Predictive Value of the Exosome Test It was found that clusterin was elevated in FTD (20.22±10.47 ng/mL), PSP (18.42±8.84 ng/ml) and CBS (16.16±6.07 ng/ml) (FIG. 14A) but not elevated in RBD (10.01±5.22 ng/mL), clinical PD (9.72±6.02 ng/mL), MSA (6.84±3.24 ng/mL) or HC (8.67±4.92 ng/mL). The differential abundance of clusterin in unrelated proteinopathies suggests that integration of clusterin in a blood-based exosome test could be of value in distinguishing PD patients from tau-related atypical parkinsonian syndromes (FIG. 14B). This is demonstrated in the heatmap (FIG. 14C) that summarises the overall trend of the biomarkers (mean concentrations were used) across different patient groups when normalised to HC. In contrast, the generic exosomal protein syntenin-1 did not exhibit a disease-specific distribution with sufficient separation to contribute as a biomarker (FIG. 15).

Figure 14D:
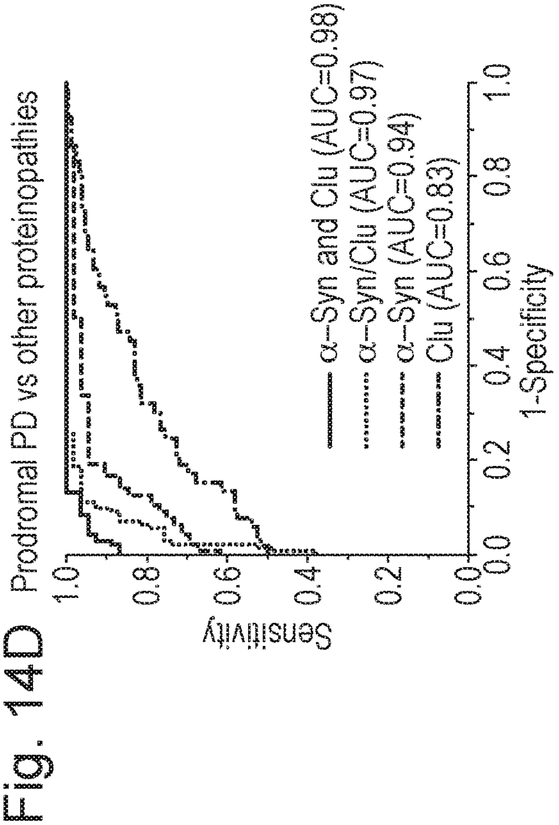
Figure 14E:
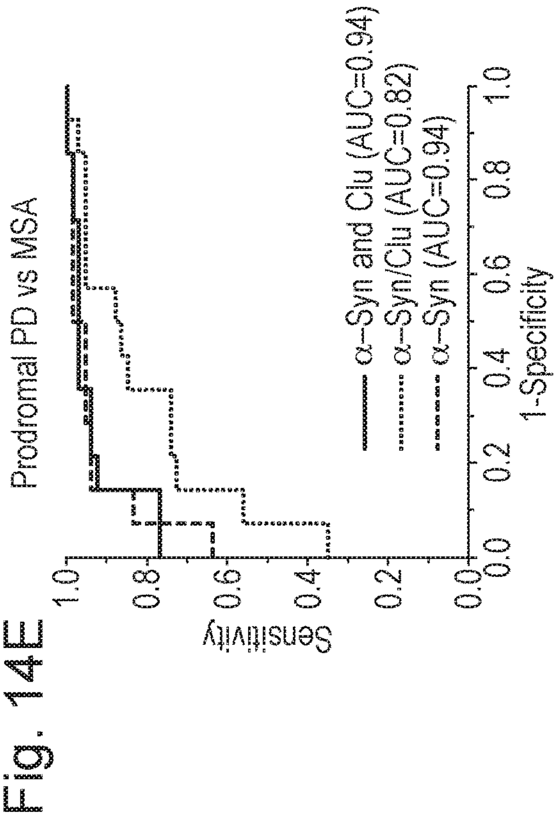
Figure 14F:
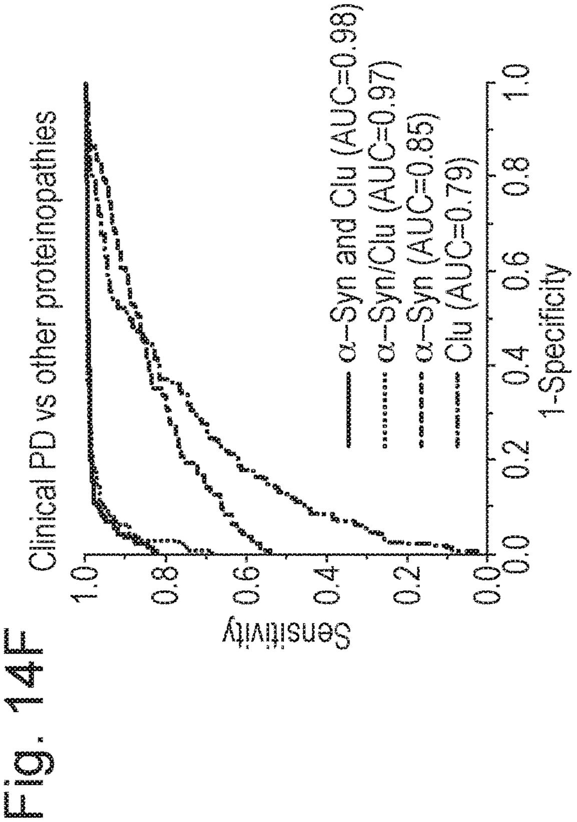
Figure 14G:
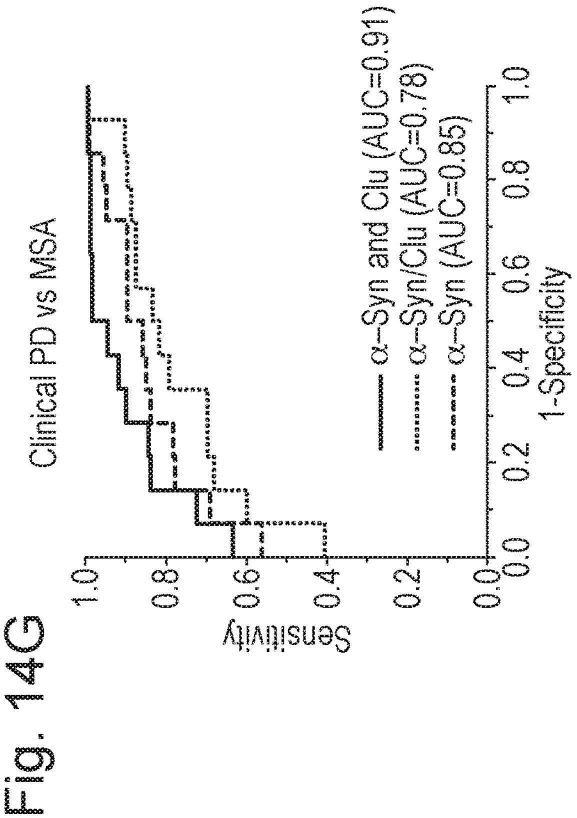

To further evaluate the clinical potential of combined α-synuclein and clusterin measurements in L1 CAM-positive exosomes as biomarkers, the α-synuclein to clusterin ratio was assessed and a logistic regression model was applied for the combination of these markers. The composite α-synuclein and clusterin measurement exhibited an improved AUC, sensitivity, and specificity estimates for differential diagnosis in predicting clinical PD versus other proteinopathies, with an AUC=0.98 (sensitivity 0.94; specificity 0.96), even in the prodromal phase of PD (RBD vs other proteinopathies, AUC=0.98, sensitivity 0.95, specificity 0.93) as shown in FIGS. 14D and 14F and Table 4. This measurement also exhibited a high performance in distinguishing prodromal or clinical PD from MSA (AUC=0.94 and 0.91 respectively) as summarised in FIGS. 14E and 14G.

Table 4 Summary of ROC Analyses in Patient Group Across Cohorts Comparing Synucleinopathies to Controls or Other Proteinopathies Using α-Synuclein, Clusterin and Composite Marker (α-Synuclein and Clusterin).

Composite marker was analysed with logistic regression. ROC-based separations were applied where there is significant difference between two groups ($p<0.001$). High-performance ($AUC\geq0.90$) markers are shown in bold and underlined.

| | α-Syn (pg/mL) | | | | Clu (ng/mL) | | | |
|---|---|---|---|---|---|---|---|---|
| Groups | AUC | Cut-off | Spec | Sens | AUC | Cut-off | Spec | Sens |
| RBD vs. HC | 0.88 | 14.55 | 0.72 | 0.94 | — | — | — | — |
| RBD vs MSA | 0.94 | 14.12 | 0.86 | 0.94 | — | — | — | — |
| RBD vs. FTD+ PSP+ CBS | 0.94 | 14.61 | 0.81 | 0.94 | 0.83 | 12.49 | 0.81 | 0.72 |
| PD vs. HC | 0.86 | 14.50 | 0.72 | 0.81 | — | — | — | — |
| PD vs. FTD+ PSP+ CBS | 0.83 | 14.56 | 0.81 | 0.72 | 0.82 | 12.06 | 0.74 | 0.74 |
| PD+ PDD vs. HC | 0.85 | 14.50 | 0.72 | 0.81 | — | — | — | — |
| PD+ PDD vs MSA | 0.85 | 13.70 | 0.86 | 0.78 | — | — | — | — |
| PD+ PDD vs. FTD+ PSP+ CBS | 0.85 | 14.38 | 0.80 | 0.74 | 0.79 | 12.39 | 0.71 | 0.72 |
| RBD, PD, PDD vs. HC | 0.82 | 0.80 | 0.72 | 14.50 | — | — | — | — |
| RBD, PD, PDD vs. FTD+ PSP+ CBS | 0.86 | 14.36 | 0.80 | 0.83 | 0.80 | 12.42 | 0.73 | 0.76 |
| RBD, PD, PDD, DLB vs. HC | 0.82 | 14.45 | 0.75 | 0.79 | — | — | — | — |
| RBD, PD, PDD, DLB vs. FTD+ PSP+ CBS | 0.83 | 14.32 | 0.78 | 0.80 | 0.87 | 12.45 | 0.82 | 0.85 |
| HC vs. FTD+ PSP+ CBS | — | — | — | — | 0.86 | 12.41 | 0.81 | 0.82 |
| MSA vs. FTD+ PSP+ CBS | — | — | — | — | 0.93 | 8.99 | 0.93 | 0.90 |

| | α-Syn/Clu | | | | Composite of α-Syn and Clu | | | |
|---|---|---|---|---|---|---|---|---|
| Groups | AUC | Cut-off | Spec | Sens | AUC | Cut-off (probability) | Spec | Sens |
| RBD vs. HC | 0.78 | 2.18 | 0.74 | 0.74 | 0.81 | 0.20 | 0.72 | 0.92 |
| RBD vs MSA | 0.82 | 2.15 | 0.86 | 0.73 | 0.94 | 0.31 | 0.86 | 0.92 |
| RBD vs. FTD+ PSP+ CBS | 0.97 | 1.38 | 0.89 | 0.96 | 0.98 | 0.53 | 0.93 | 0.95 |
| PD vs. HC | 0.77 | 1.95 | 0.70 | 0.73 | 0.84 | 0.54 | 0.73 | 0.77 |
| PD vs. FTD+ PSP+ CBS | 0.98 | 1.13 | 0.92 | 0.94 | 0.98 | 0.68 | 0.96 | 0.92 |
| PD+ PDD vs. HC | 0.77 | 1.95 | 0.70 | 0.72 | 0.84 | 0.58 | 0.70 | 0.79 |

-continued

| | | | | | | | | |
|---|---|---|---|---|---|---|---|---|
| PD+ PDD vs MSA | 0.78 | 2.14 | 0.86 | 0.68 | 0.91 | 0.09 | 0.86 | 0.84 |
| PD+ PDD vs. FTD+ PSP+ CBS | 0.97 | 1.13 | 0.92 | 0.94 | 0.98 | 0.41 | 0.96 | 0.94 |
| RBD, PD, PDD vs. HC | 0.76 | 1.21 | 0.71 | 0.73 | 0.85 | 0.61 | 0.71 | 0.82 |
| RBD, PD, PDD vs. FTD+ PSP+ CBS | 0.96 | 1.39 | 0.89 | 0.89 | 0.96 | 0.79 | 0.97 | 0.92 |
| RBD, PD, PDD, DLB vs. HC | 0.81 | 2.08 | 0.76 | 0.79 | 0.83 | 0.65 | 0.77 | 0.75 |
| RBD, PD, PDD, DLB vs. FTD+ PSP+ CBS | 0.95 | 1.40 | 0.93 | 0.92 | 0.96 | 0.76 | 0.96 | 0.92 |
| HC vs. FTD+ PSP+ CBS | 0.89 | 1.41 | 0.82 | 0.84 | 0.89 | 0.59 | 0.81 | 0.86 |
| MSA vs. FTD+ PSP+ CBS | 0.94 | 1.22 | 0.94 | 0.93 | 0.97 | 0.83 | 0.94 | 0.93 |

Conclusion

It was found that mean exosomal α-synuclein was increased by 2-fold in prodromal and clinical Parkinson's disease when compared to Multiple system atrophy (MSA), controls or other neurodegenerative diseases. With 314 subjects in the training group and 105 in the validation group, exosomal α-synuclein exhibited a consistent performance (AUC=0.86) in separating clinical Parkinson's disease from controls across populations. Exosomal clusterin was elevated in subjects with non-α-synuclein proteinopathies. Combined neuron-derived exosomal α-synuclein and clusterin measurement predicted Parkinson's disease from other proteinopathies with AUC=0.98 and from MSA with AUC=0.94.

In conclusion, increased α-synuclein egress in serum neuronal exosomes precedes the diagnosis of Parkinson's disease, persists with disease progression and in combination with clusterin predicts and differentiates Parkinson's disease from atypical parkinsonism.

Example 4

This example demonstrates the excellent antifouling properties of the coated particles described herein, and the improved sensitivity of these assays compared to commercially available electrochemiluminescence kits.

Materials

All chemical reagents were used as received. Potassium ferricyanide, potassium ferrocyanide, 3-mercaptopropionic acid (3-MPA), 2-mercaptoethanol (2-MU), 1-ethyl3-(3-(dimethylamino)propyl) carbodiimide (EDC), N-hydroxysuccinimde (NHS), Triton X-100 (TX), bis(carboxymethyl) trithiocarbonate (BisCTTC) were obtained from Sigma-Aldrich (Gillingham, U.K.). Commercial electrochemiluminescence (ECL) detection plates with linkers and ruthenium tags were ordered from Meso Scale Discovery (MSD, United States). Sera-Mag Carboxylate modified magnetic beads (24152105050250) were purchased from GE Healthcare and used as controls. (Buckinghamshire, UK). Nanoparticle tracking analysis was carried out using Malvern NanoSight NS500 (Malvern, UK), configured with a 405 nm laser and a high sensitivity CMOS camera (OrcaFlash2.8, Hamamatsu C11440, NanoSight Ltd.). Videos were collected and analyzed using the NTA software (version 2.3, build 0025) with camera level and detection threshold set at 14 and 5, respectively. All analysis were carried out at a controlled temperature of 23° C.

Fetal bovine serum (FBS), C-reactive protein (CRP), bovine serum albumin (BSA) and human serum albumin (HSA) were purchased from Sigma-Aldrich. α-Synuclein (αSyn), Syntenin-1 (Synt-1) standards, anti-α-Syn, anti-Syn-1, anti-L1CAM, and antihemagglutinin (HA) antibodies were obtained from Abcam (Cambridge, UK). All protein samples were diluted in filtered PBS buffer solutions (pH 7.4).

Parkinson's disease (PD) and healthy controls (HC) were recruited and whole blood samples collected in compliance with the institutional guidelines and ethical approval. Full details of the Kiel-PD cohort are published in Reference 49.

Methods

Preparation of antifouling pCBMA-coated MBs The magnetic microbeads were prepared by a two-step approach comprising the formation of ferrihydrite/formaldehyde composite microbeads and subsequent hydrothermal reduction of the ferrihydrite to magnetite. Iron hydroxide was synthesized by hydrolysis of ferric chloride salt solution at room temperature as described in references 26 and 27. Briefly, a total of 16 g of $NaHCO_3$ was slowly added to a 100 mL of ultrapure water in which 25 g of $FeCl_3 \cdot 6H_2O$ was dissolved. The mixture was stirred for 1 h to yield a reddish brown ferrihydrite solution, prior to the addition of 1.05 g of urea then a pH adjustment to 2.0 with 2 M nitric acid. This was followed by addition of 1.57 mL of aqueous formaldehyde (37 wt %) under stirring. After the addition was complete, the mixture was left without agitation at ambient temperature. Within 10 min, a yellowish gel is formed. The microspheres generated were allowed to age overnight, prior to collection by filtration and washing with Milli-Q water (18.2 MΩ, Millipore UK Ltd). Finally, the particle samples were suspended in 130 mL of 0.1 M sodium borohydride solution (pH 9.0), and the suspension transferred to an autoclave. The reaction was carried out at 80° C. for 2 h, during which the initially yellowish microspheres turn black, and can be readily magnetically extracted prior to a thorough wash with EtOH and Milli-Q water. These are then oven dried at 40° C., and resuspended in Milli-Q water at a concentration of 50 mg/mL.

The bead surfaces were functionalized with the bifunctional RAFT agent BisCTTC as follows: 1 mL of the $Fe_3O_4$ suspension was added to a 10 mL mixture of water/ethanol (3/7, v/v) under ultrasonication for 10 min at room temperature, followed by the addition of 10 mg of BisCTTC (0.044 mmol). A water/ethanol solvent was chosen to ensure dispersion of the magnetic beads and solubilization of BisCTTC. The mixture was left under magnetic stirring and a stream of nitrogen for 24 h. The final product of $Fe_3O_4$@ BisCTTC was separated and purified by magnetic collection and washed three times with ethanol and Milli-Q water.

In a final step, BisCTTC and 4,4'-Azobis (4-cyanovaleric acid) (ACVA) were used as monomer, free chain transfer agent (in solution phase) and initiator, respectively. Synthesis of pCBMA@ $Fe_3O_4$ was performed through a standard RAFT polymerization procedure. Typically, 1 mL of the suspension containing $Fe_3O_4$@ BisCTTC beads was mixed with CBMA (360 mg, 1.568 mmol), ACVA (1.1 mg, 0.00392 mmol) and free CTA BisCTTC (3.55 mg, 0.01568 mmol) dissolved in 10 mL of ethanol/water (1:1). After the reaction mixture was purged with nitrogen for one hour, the glass flask was heated in an oil bath at 70° C., and left for 8 hours with mechanical stirring under S-5 nitrogen. The reaction was terminated by inserting the reaction flask in an ice bath followed by exposure to air (quenching). The final pCBMA@ $Fe_3O_4$ bead product was magnetically separated and washed several times with ethanol and water.

Fabrication of immunobeads The antifouling immunobeads were prepared by conjugation of anti-L1CAM Ab (ab20148, Abcam) to pCBMA@ $Fe_3O_4$. Specifically, the carboxyl acid groups of the pCBMA@ $Fe_3O_4$ beads (1 mg/mL) were activated with 50 mg/mL of EDC/NHS in IVIES buffer and then reacted with 8 μg/mL (final concentration) of anti-L1CAM or CD9 antibody at room temperature for 1.5 h. After washing with PBS using a magnet, the beads were mixed in 1 mL of PBS containing 5 mg/mL BSA (to quench any remaining activated sites and backfill any residual space), for 30 min at room temperature. The immunobeads were collected magnetically and stored at 4° C. until further use. All such immunobeads were prepared and consumed in the same day.

Fourier transform infrared-attenuated total reflectance (FTIR-ATR) An appropriate amount of the prepared pCBMA magnetic beads were washed with ethanol and Milli-Q water and dried at 50° C. prior to examination. CBMA monomer and uncoated $Fe_3O_4$ magnetic beads were used as controls. All spectra were recorded between 4000-400 cm-1 with a Bruker Vertex 80 spectrometer equipped with mercurycadmium-telluride (MCT) detector and an ATR-unit (DuraSampllR II diamond ATR) at a resolution of 2 $cm^{-1}$ and evaluated using OPUS 6.5 software.

Antifouling test for pCBMA beads To test the antifouling performance of the pCBMA beads, 1 mg of the AbpCBMA@ $Fe_3O_4$ or 1 mg of pCBMA@ $Fe_3O_4$ (uncoated $Fe_3O_4$ beads were used as control) were added separately into 10 mg/mL BSA solution and incubated for 1 h at room temperature. Supernatant containing unbound protein were collected, subject to the bicinchoninic acid (BCA) test and adsorbed protein determined from:

$$\text{Adsorbed amount} = \text{Input amount} - \text{Unbound amount in the supernatant}$$

To evaluate the nonspecific adsorption level of free α-Synuclein to the immunobeads, 1 mg pCBMA magnetic beads coated with antiL1CAM antibody (anti-HA antibody or no antibody as controls), were added to 500 μL PBS containing 20 ng/mL α-synuclein standard protein (i.e. a concentration that reflects clinically relevant levels of free α-synuclein in blood). The mixtures were gently shaking overnight at 4° C. After incubation, the supernatant fraction were collected using magnetic rack. Control beads (commercial carboxylate magnetic beads) with same experimental setting were carried out in parallel. The adsorbed amount of α-synuclein onto the beads were quantified using the ECL kit using the following equation:

$$\text{Adsorbed amount} = \text{Input amount} - \text{Unbound amount in the supernatant.}$$

Zeta potential The surface zeta potential analysis was performed with uncoated $Fe_3O_4$ beads and pCBMA-coated MBs (ca. 1 mg/mL) in PBS (10 mM, pH=7.4) on a Malvern Zetasizer Nano with a 532 nm laser as the light source.

Exosome isolation For exosome isolation a 3-step sequential spin (300 g for 10 min, 2000 g for 20 min, and 10,000 g for 30 min) was used to remove cellular debris, protein aggregates and fatty material from the serum. An appropriate amount of supernatant (0.5 mL for commercial ECL plate and 0.1 mL for EIS sensor), i.e. pre-cleared serum, was transferred to protein low-binding tubes (Eppendorf) for immunocapture using antiL1CAM antibodies pre-conjugated to pCBMA beads that were generated to reduce non-specific adsorption. The immunobeads were incubated at 4° C. overnight on a rotating mixer and bead-exosomes complexes were collected by magnetic separation and washed successively with 0.05% Tween-20 in PBS (PBST) and PBS. For exosomal protein quantification the isolated exosomes were lysed in lysis buffer containing 1% triton X-100 in PBS with 4% protease inhibitors (50 μL for commercial ECL plate and 10 μL for EIS sensor) for 15 min at room temperature for exosomal protein quantification.

Transmission electron microscopy Transmission electron microscopy (TEM) was used to examine the shape and morphology of the captured exosomes eluted from pCBMA beads. Specifically, the captured EVs on MBs were eluted by adding 20 μL of Glycine solution (pH 2.9) and the pH was adjusted back to neutral quickly with 20 μL of Tris solution (pH 9.5). 10 μl of resultant eluent samples was applied to freshly glow discharged carbon formvar 300 mesh copper grids for 2 mins, blotted with filter paper and stained with 2% uranyl acetate (aqueous) for 10 s, then blotted and air dried. Grids were imaged with a TEM operated at 120 kV using a Gatan OneView CMOS camera.

Scanning electron microscopy Immunocaptured exosomes on the pCBMA beads were fixed in 2% glutaraldehyde on clean silicon wafer and washed twice with PBS.

After natural evaporation, the samples were coated with around 5 nm platinum using a sputter coater (Cressington) and imaged with a scanning electron microscope at 5 kV (JEOL 6010LV).

Western blot Western blot was used to characterize the transmembrane and internal proteins from immunocaptured exosomes. Exosomes captured by anti-L1CAM immunobeads (or anti-CD9 as positive control targeting generic exosomes and anti-HA immunobeads as negative control) were lysed in LDS buffer (Thermo Fisher) and resolved using sodium dodecyl sulfate polyacrylamide gel electrophoresis (SDS-PAGE), transferred onto polyvinylidene fluoride membranes (PVDF, Invitrogen) and immunoblotted with antibodies against Synt-1 (ab133267, Abcam), CD9 (CBL162, Millipore), and L1 CAM (ab80832, Abcam). All antibodies were used at 1:1,000 dilution. Following incubation with a horseradish peroxidase-conjugated secondary antibody (GE Healthcare) (1:10,000 dilution), chemiluminescence was used for immunodetection (ChemiDoc, Bio-Rad).

Commercial electrochemiluminescence detection Electrochemiluminescence (ECL) detection was performed in 96-well Meso Scale Discovery (MSD) U-Plex plates following the manufacturer instruction. Two unique linkers for the selected capture antibodies (anti-Synt-1, anti-α-synuclein) were used according to the manufacturer's protocol. Immunocaptured exosome lysates or S-8 standards solution (50 μL) were loaded and incubated at room temperature for 1 h. After three washes, detection antibodies with Sulfo-TAG-labels were incubated for 1 hour. Following washes by wash buffer (from Meso Scale Discovery) and the addition of MSD Read buffer (from Meso Scale Discovery) the plates were read using the MSDECL platform (Quick-Plex SQ 120). Data were analysed with the MSD Discovery Workbench 3.0 Data Analysis Toolbox. Antibody pairs for α-synuclein (preconjugated with biotin and ruthenium tag, provided by Meso Scale Discovery) were provided by MSD. Additive-free anti-Synt-1 goat polyclonal antibody (PAB7132, Abnova) and anti-Synt-1 rabbit monoclonal antibody (ab236071, Abcam) were conjugated with biotin and ruthenium and used as capture and detection antibodies, respectively.

Exosome capture efficiency To evaluate the exosome capture efficiency using the immunobeads, anti-CD9 antibody modified pCBMA@ $Fe_3O_4$ MBs were prepared following the same procedure of "Fabrication of immunobeads" described above. Immunobeads (0.2 mg) were mixed with 100 μL pre-cleared serum to allow incubation at 4° C. overnight. After incubation, the supernatants were collected with the aid of an external magnetic rack. The exosome concentration in the input serum and supernatants were then measured using a nanoparticle tracking analysis of particle fractions spanning 40 to 140 nm (i.e. typical size of exosomes). The capture efficiency was measured using following equation, $$(\text{Input (CD9+exosomes)}-\text{Unbound amount})/\text{Input (CD9+ exosomes)}\times 100\% = (\text{Total input amount}\times 75\%^{*}-\text{Unbound amount})/\text{Total input amount}\times 75\%)\times 100\% = (2.66-0.51)/2.66\times 100\% = 80.8\%$$

(Note: CD9+ exosomes constitute about 75% of total exosome population).

Fabrication of receptor interface and EIS detection Au disk electrodes (3.0 mm in diameter, purchased from BASi®, USA) were mechanically polished with 1.0 μm, 0.3 μm and 0.05 μm alumina slurry, respectively. The electrodes were ultrasonicated in ethanol for 10 min, and immersed in piranha (v/v 3:1, $H_2SO_4$:$H_2O_2$) for 10 min. After rinsing with Milli-Q water and dried with nitrogen, the electrodes were immersed in 0.5 M KOH aqueous solution for 100 cycles of cyclic voltammetry scans (from −1.7 to −0.7 V). They were then electrochemically cycled in 0.5 M $H_2SO_4$ from −0.15V to 1.35V vs an Ag wire reference electrode at 0.1 V/s until the height and shape of anodic and cathodic peaks were constant.

Mixed SAMs of 3-MPA and 2-MU were generated by immersion of clean gold disk electrodes in 50 mM 3-MPA and 10 mM 2-MU solution overnight at room temperature in the dark. The electrodes were rinsed with ethanol to remove physically adsorbed molecules and then dried in an argon stream. The terminal carboxyl groups of 3-MPA were then activated with 0.4 M EDC/NHS solution for 30 min, and washed carefully with PBS. 10 μL of antibody solution with an optimized concentration of 100 μg/mL was then incubated on the electrode for 1 h, and the surface was then blocked with FBS solution for 30 min to deactivate any residual carboxylic groups. The stability of antibody-modified electrode was tested by repetitive incubating in PBS for 20 mins and subsequent EIS assessments in 5 mM of $K_3[Fe(CN)_6]$ and $K_4[Fe(CN)_6]$. Afterwards, 10 μL of α-Syn, Synt-1 spiked into 10% human serum or exosomes lysate (obtained by adding 1% triton X-100 in PBS with 4% protease inhibitors to the exosomes-beads composite at room temperature for 15 min) was then incubated on the electrode for an optimized incubation time of 20 mins, and washed with PBS solution. Selectivity analyses were conducted by incubating sensor electrodes with $10^{-3}$ g/mL of CRP, $10^{-3}$ g/mL of α-Syn, or $10^{-3}$ g/mL of BSA for 20 mins prior to washing with PBS solution. EIS measurements were recorded with a PalmSens electrochemical workstation with a standard three electrode configuration, and they were conducted in 5 mM of $K_3[Fe(CN)_6]$ and $K_4[Fe(CN)_6]$ in PBS solution. All measurements were carried out with setting fixed at amplitude 0.01 V and frequencies ranging from 100 kHz to 100 mHz. $R_{ct}$ upon addition of antibody ($R_{ct\text{-}antibody}$) and S-10 antigen ($R_{ct\text{-}antigen}$) were calculated from the fitting of equivalent circuit diagram.

The relative response are determined from:

$$\text{Relative response}=R_{ct\text{-}antigen}-R_{ct\text{-}antibody}.$$

Statistical analysis of patient samples were through a standard Student's t-test.

Results

Examination of Performance and Anti-Fouling Properties

As described above, magnetic beads (~2.4 μm) were coated with the zwitterionic polymer pCBMA via the RAFT process and were further modified with the anti-L1CAM antibody.

Zeta potential assessments were measured before ($Fe_3O_4$, −33.8±3.2 mV) and after (pCBMA@ $Fe_3O_4$, −2.3±1.2 mV) polymerization, indicating a near-zero overall charge as desired for optimal performance (see references 50 and 51).

The antifouling properties of the pCBMA@ $Fe_3O_4$ MBs were confirmed through a markedly reduced (~90%) non-specific adsorption of bovine serum albumin (BSA) when compared to native $Fe_3O_4$ beads (see FIG. 16). It is noteworthy that, even after antibody conjugation (i.e., anti-L1CAM modified pCBMA@ $Fe_3O_4$ MBs), antifouling performance is not significantly compromised. It was further demonstrated that pCBMA@ $Fe_3O_4$ MBs, unlike commercially available carboxylate MBs, exhibited good antifouling properties when incubated with soluble recombinant α-synuclein, irrespective of the antibody used (anti-L1CAM or anti-HA as shown in FIG. 17A). This is critically important in supporting the selective and clean isolation of exosomes from serum samples.

The anti-L1CAM antibody-coated pCMBA were then assessed for immunocapture of neuronal exosomes in serum. SEM image analysis clearly showed exosomes bound to anti-L1CAM conjugated pCBMA@ $Fe_3O_4$ MBs (FIG. 17B) but not control beads (i.e., anti-HA Ab-coated pCBMA@ $Fe_3O_4$ beads, inset in FIG. 17B).

Figure 17C:
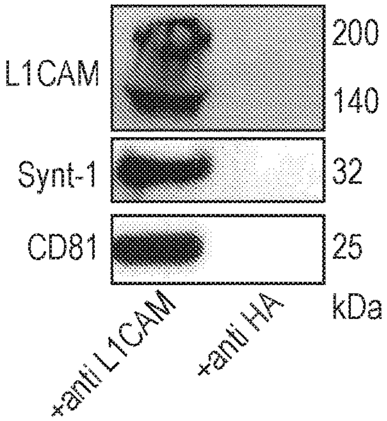
Figure 18:
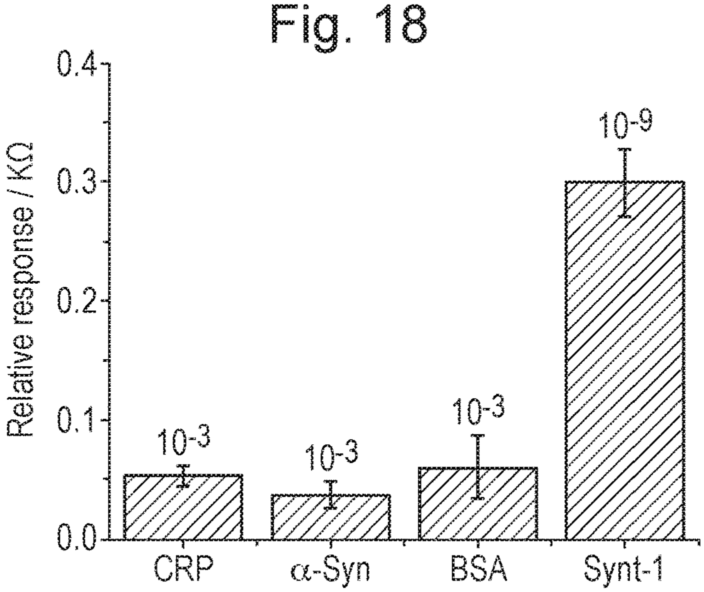

To further confirm their molecular composition, captured vesicles were lysed and processed for immunoblotting (FIG. 17C). The transmembrane markers L1 CAM and CD 81 and the internal protein marker Synt-1 were detected in lysates from anti-L 1CAM@pCBMA@$Fe_3O_4$ MBs samples but not in control lysates (samples incubated with anti-HA-coated pCBMA@$Fe_3O_4$ MBs).

Figure 17D:
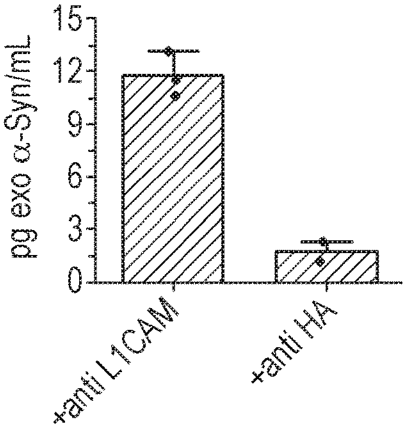

It was also confirmed that anti L1 CAM-modified pCBMA $Fe_3O_4$ MBs are effective in isolating from serum neuronal exosomes containing α-Syn (FIG. 17D).

Comparison of Selectivity to Commercially Available Electrochemiluminescence Kits The selectively captured exosomes were quantified electrochemically as described above. In particular, the reliability of biomarker quantification was tested through the repeat analysis of prepared spiked solutions for both α-Syn and Synt-1, including analyses with control proteins (e.g., C-reactive protein (CRP) and BSA) at greater than $10^6$ times excess of the expected marker levels (FIG. 18). Reliable triplicate quantifications of both markers (FIG. 19) were demonstrable within 30 min with limits of detection (LOD) and quantification (LOQ) at 0.3 and 0.8 pg/mL for α-Syn, respectively (FIG. 20). This is notably better than most prior exosomal analyses. Thus, the assays herein are significantly more sensitive than commercial electrochemiluminescence kits (by almost an order of magnitude), much cheaper, much faster, and require markedly less sample input (100 vs 500 μL).

Example 5

This example uses patients from additional cohorts to further validate the clinical utility of α-synuclein measurement, and optionally in combination with clusterin measurement, in serum neuronal exosomes as biomarkers across the spectrum of Parkinson's disease, multiple system atrophy and other proteinopathies.

Materials and Methods

A total of 288 subjects were included in this study (Table 5). Serum samples and clinical data were collected from patients with polysomnographically confirmed REM (Rapid eye movement (REM)) sleep behavior disorder (RBD) (n=26), PD (n=45), multiple system atrophy (MSA) (n=36), Progressive supranuclear palsy (PSP) (n=81) and Corticobasal Syndrome (CBS) (n=43). Healthy controls (HC) (n=57) were of similar age and sex.

L1 CAM positive neuronal exosomes were isolated as detailed in Example 2, except a lower volume of serum was used (250 μL instead of 500 μL).

The samples were analysed blindly for α-synuclein, clusterin and syntenin-1 as detailed in Example 2.

Statistical analyses were carried out as detailed in Examples 2 and 3.

TABLE 5

Disease and healthy control groups used for validation study

| | RBD | PD | MSA | HC | PSP | CBS |
|---|---|---|---|---|---|---|
| Number | 26 | 45 | 36 | 57 | 81 | 43 |

Results

The results are shown in FIGS. 21 to 25.

It can be seen that there was a significant increase in exosomal α-synuclein in RBD and PD compared to controls (FIG. 21) and higher clusterin in PSP and CBS (FIG. 23). A significant increase in the α-synuclein/clusterin ratio can also be seen in RBD and PD compared to the controls (FIG. 24).

It was further confirmed by using ROC analysis that α-synuclein or α-synuclein/clusterin ratio independently offers an accurate biomarker that predicts neuronal synucleinopathy in RBD and PD vs MSA (glial synucleinopathy) or tauopathy (PSP, CBS) (see FIGS. 22 and 25).

These observations are consistent with the observations from the Examples above.

REFERENCES

1 Berg et al. Mov Disord. 2015; 30:1600-1611.
2 Fereshtehnej ad et al. Brain. 2019; 142:2051-2067.
3 Helv et al. Mov Disord. 2008; 23:837-844.
4 Braak et al. Neurobiol Aging. 2003; 24:197-211.
5 Tofaris and Spillantini Cell Mol Life Sci. 2007; 64:2194-2201.
6 Behari et al., Ann Indian Acad Neurol. 2011 July; 14(Suppl1): S2-S6.
7 Mollenhauer et al., Lancet Neurol. 2011; 10:230-240.
8 Eusebi et al., Mov Disord. 2017; 32:1389-1400.
9 El-Agnaf et al., FASEB J. 2003; 17:1945-1947.
10 Shi et al., Neurosci Lett. 2010; 480:78-82.
11 Parnetti et al., Lancet Neurol. 2019; 18:573-586.
12 Tomlinson et al., Ann Clin Transl Neurol. 2015; 2:353-361.
13 Cerri et al., Front Cell Neurosci. 2018; 12:125.
14 Steudl et al., 2016, Brain, 139, 481-494.
15 Shi et al., Acta Neuropathol. 2014; 128:639-650.
16 Kim et al., Bioconj Chem 2012 Oct. 17; 23(10)2114-20).
17 Harold et al. Nat Genet. 2009; 41:1088-1093.
18 Gibb and Lees, 1988, J Neurol Neurosurg Psychiatry, 51:745-52.
19 Gelb et al., 1999, Arch Neurol, 56:33-39.
20 Postuma et al., 2015, Mov Disord, 30:1591-1601.
21 Manfredi et al., J Neural Transm Suppl. 1995; 45:1-9.
22 Tofaris J Parkinsons Dis. 2017; 7:569-576.
23 Lachenal et al., *Mol. Cell. Neurosci.* 46, 409-418 (2011).
24 Faure et al. *Mol. Cell. Neurosci.* 31, 642-648 (2006).
25 Li et al., Biomaterials 2014; 35(36):9731-45.
26 Deng et al., 2013, Anal Chim Acta 771: 31-36.
27 Zhang et al., 2008 Chem Mater 20: 3345-335.
28 Ratcliffe et al., Polym Chem 5: 3643-3655.
29 Dalrymple-Alford et al., Neurology. 2010; 75:1717-1725.
30 Postuma et al., Brain. 2009; 132:3298-3307.
31 Boot et al., Ann Neurol. 2012; 71:49-56.
32 Fujiwara et al., Nat Cell Biol. 2002; 4:160-164.
33 Harold et al., Nat Genet. 2009; 41:1088-1093.
34 Lambert et al., Nat Genet. 2009; 41:1094-1099.
35 Wang et al., Sci Transl Med. 2012; 4:121ra120.
36 Jiang et al., ACS Sensors. 2016; 1:1432-1438.

37 Robinson et al., Brain. 2018; 141:2181-2193.
38 Thambisetty et al., Arch Gen Psychiatry. 2010; 67:739-748.
39 Yang et al., Metabolic Brain Disease. 2019; 34:129-140.
40 Slot et al., Neurobiol Aging. 2019; 79:101-109.
41 Tofaris Mov Disord. 2012; 27:1364-1369.
42 Tofaris et al., Proc Natl Acad Sci USA. 2011; 108:17004-17009.
43 Hasegawa et al., PLoS One. 2011; 6:e29460.
44 Alexopoulou et al., Proc Natl Acad Sci USA. 2016; 113:E4688-4697.
45 Alvarez-Erviti et al., Neurobiol Dis. 2011; 42:360-367.
46 Minakaki et al., Autophagy. 2018; 14:98-119.
47 Fussi et al., Cell Death Dis. 2018; 9:757.
48 Postuma et al., Neurology. 2015; 84:1104-1113.
49 Hopfner et al., Transl Neurodegener 2019, 8, 11.
50 Visova et al., Langmuir, 2020, 36, 8485-8493.
51 Keefe et al., Nat. Chem., 2012, 4, 59-63.

The invention claimed is:

1. A method for preventing and/or treating Parkinson's Disease (PD) in a subject, comprising:

a) identifying a subject susceptible to PD or having PD by analysing a blood sample from the subject, wherein the step of analysing the blood sample comprises determining the levels of α-synuclein and clusterin in neuron-derived exosomes in the blood sample, wherein the levels of α-synuclein and clusterin provide a diagnostic indicator of a subject susceptible to Parkinson's disease (PD) or of a subject having PD; and b) treating the subject with a therapy for PD;

wherein an increase in the level of a-synuclein relative to a reference indicates that the subject is susceptible to PD or has PD; wherein the reference is: (i) a threshold value of between 10-20 pg/ml; or (ii) the α-synuclein level in a sample from a negative control; and wherein a decrease or no change in the level of clusterin relative to a reference indicates that the subject is susceptible to PD, wherein the reference is: (i) a threshold value of between 7-17 ng/ml, or (ii) the clusterin level in a sample from a negative control.

2. The method of claim 1, wherein the subject susceptible to PD is a subject having prodromal PD.

3. The method of claim 1, wherein the reference for α-synuclein is a threshold value of between 10-20 pg/ml.

4. The method of claim 1, wherein the reference for clusterin is a threshold value of between 7-17 ng/ml.

5. The method of claim 1, wherein the blood sample is from a subject having one or more signs or symptoms of parkinsonism and who has not been diagnosed with PD.

6. The method of claim 5, wherein the signs or symptoms of parkinsonism comprise:

one or more of non-motor signs: diagnosis of rapid eye movement sleep behaviour disorder (RBD), olfactory dysfunction, constipation, excessive daytime somnolence, symptomatic hypotension, erectile dysfunction, urinary dysfunction, and/or diagnosis of depression, one or more of non-motor signs: altered handwriting, turning in bed, disrupted walking, disrupted salivation, disrupted speech, reduced facial expression, rigidity, balance impairments, resting tremor, bradykinesia (slow movement), and/or postural instability; and/or abnormal tracer uptake of the presynaptic dopaminergic system.

7. The method of claim 1, wherein the neuron-derived exosomes contain L1 cell adhesion molecule (L1CAM).

8. The method of claim 7, further comprising isolating the exosomes using ligands having affinity to L1CAM.

9. The method of claim 1, wherein the level of α-synuclein and clusterin are determined in serum obtained from the blood sample of the subject.

10. The method of claim 1, wherein the method comprises discriminating a subject having PD from multiple system atrophy (MSA), progressive supranuclear palsy (PSP), corticobasal syndrome (CBS), or frontal temporal dementia (FTD) when the threshold value is determined by a negative control comprising patients having MSA, PSP, CBS, or FTD, wherein if the blood sample: (i) contains a higher α-synuclein level in the neuron-derived exosomes relative to the threshold value for α-synuclein, and (ii) has a clusterin level that is decreased or not changed compared to the threshold value, this indicates that the subject has PD and not MSA, PSP, CBS, or FTD.

11. The method of claim 10, wherein the method comprises discriminating a subject having PD from MSA, when the threshold value is determined by a negative control comprising patients having MSA, wherein if the blood sample: (i) contains a higher α-synuclein level in the neuron-derived exosomes relative to the threshold value for α-synuclein, and (ii) has a clusterin level that is decreased or not changed compared to the threshold value, this indicates that the subject has PD and not MSA.

* * * * *